United States Patent
Kagan et al.

(10) Patent No.: US 8,070,743 B2
(45) Date of Patent: Dec. 6, 2011

(54) DEVICES AND METHODS FOR ATTACHING AN ENDOLUMENAL GASTROINTESTINAL IMPLANT

(75) Inventors: Jonathan Kagan, Hopkins, MN (US); Mitchell Dann, Wilson, WY (US); Lee Guterman, Amherst, NY (US); Joshua Butters, Chandler, AZ (US); Paul Swain, London (GB); T. Wade Fallin, Hyde Park, UT (US); Thomas Baldwin, Amalga, UT (US)

(73) Assignee: ValenTx, Inc., Carpinteria, CA (US)

( * ) Notice: Subject to any disclaimer, the term of this patent is extended or adjusted under 35 U.S.C. 154(b) by 1735 days.

(21) Appl. No.: 11/124,634

(22) Filed: May 5, 2005

(65) Prior Publication Data

US 2006/0020247 A1    Jan. 26, 2006

Related U.S. Application Data

(63) Continuation-in-part of application No. 10/698,148, filed on Oct. 31, 2003, and a continuation-in-part of application No. 10/998,424, filed on Nov. 29, 2004, now abandoned, and a continuation-in-part of application No. 11/025,364, filed on Dec. 29, 2004.

(60) Provisional application No. 60/569,442, filed on May 7, 2004, provisional application No. 60/613,917, filed on Sep. 27, 2004, provisional application No. 60/480,485, filed on Jun. 21, 2003, provisional application No. 60/448,817, filed on Feb. 21, 2003, provisional application No. 60/437,513, filed on Dec. 30, 2002, provisional application No. 60/430,857, filed on Dec. 3, 2002, provisional application No. 60/428,483, filed on Nov. 22, 2002, provisional application No. 60/422,987, filed on Nov. 1, 2002.

(51) Int. Cl.
*A61M 31/00* (2006.01)
(52) U.S. Cl. .......... 604/516; 604/500; 604/264
(58) Field of Classification Search .......... 604/264, 604/275–279, 96.01, 164.01, 523, 500–522; 623/23.65, 23.6; 606/153
See application file for complete search history.

(56) References Cited

U.S. PATENT DOCUMENTS

| 3,357,432 A | 12/1967 | Sparks |
| 3,589,356 A | 6/1971 | Silverman |
| 3,982,544 A | 9/1976 | Dyck |
| 4,006,747 A | 2/1977 | Kronenthal et al. |

(Continued)

FOREIGN PATENT DOCUMENTS

EP    0817598    2/1996

(Continued)

OTHER PUBLICATIONS

*Endoscopic suturing*, C. Paul Swain MD, *Balliere's Clinical Gastroenterology*, vol. 13, No. 1. pp. 97-108, 1999.

(Continued)

*Primary Examiner* — Kevin C Sirmons
*Assistant Examiner* — Phillip Gray
(74) *Attorney, Agent, or Firm* — Knobbe, Martens, Olson & Bear LLP

(57) ABSTRACT

The present invention provides devices and methods for attachment of an endoluminal gastrointestinal device, such as an artificial stoma device, a gastrointestinal bypass sleeve device or an attachment cuff, within a patient's digestive tract for treatment of obesity.

17 Claims, 52 Drawing Sheets

U.S. PATENT DOCUMENTS

| | | | |
|---|---|---|---|
| 4,043,345 A | 8/1977 | Kramann et al. |
| 4,109,659 A | 8/1978 | Sheridan |
| 4,134,405 A | 1/1979 | Smit |
| 4,217,664 A | 8/1980 | Faso |
| 4,235,238 A | 11/1980 | Ogiu et al. |
| 4,252,131 A | 2/1981 | Hon et al. |
| 4,271,839 A | 6/1981 | Fogarty et al. |
| 4,315,509 A | 2/1982 | Smit |
| 4,329,995 A | 5/1982 | Anthracite |
| 4,501,264 A | 2/1985 | Rockey |
| 4,532,926 A | 8/1985 | O'Holla |
| 4,606,347 A | 8/1986 | Fogarty et al. |
| 4,630,609 A | 12/1986 | Chin |
| 4,641,653 A | 2/1987 | Rockey |
| 4,763,653 A | 8/1988 | Rockey |
| 4,846,836 A | 7/1989 | Reich |
| 4,863,440 A | 9/1989 | Chin |
| 4,946,440 A | 8/1990 | Hall |
| 5,085,661 A | 2/1992 | Moss |
| RE34,021 E | 8/1992 | Mueller et al. |
| 5,171,305 A | 12/1992 | Schickling et al. |
| 5,236,423 A | 8/1993 | Mix et al. |
| 5,306,300 A | 4/1994 | Berry |
| 5,314,473 A | 5/1994 | Godin |
| 5,411,508 A | 5/1995 | Bessler et al. |
| 5,431,666 A | 7/1995 | Sauer et al. |
| 5,458,573 A | 10/1995 | Summers |
| 5,470,337 A | 11/1995 | Moss |
| 5,582,616 A | 12/1996 | Bolduc et al. |
| 5,645,568 A | 7/1997 | Chervitz et al. |
| 5,785,684 A | 7/1998 | Zimmon |
| 5,820,584 A | 10/1998 | Crabb |
| 5,824,008 A | 10/1998 | Bolduc et al. |
| 5,843,164 A | 12/1998 | Frantzen et al. |
| 5,861,036 A | 1/1999 | Godin |
| 5,887,594 A | 3/1999 | LoCicero, III |
| 5,957,940 A | 9/1999 | Tanner et al. |
| 5,972,023 A | 10/1999 | Tanner et al. |
| 5,997,556 A | 12/1999 | Tanner |
| 6,113,609 A | 9/2000 | Adams |
| 6,193,733 B1 | 2/2001 | Adams |
| 6,254,642 B1 | 7/2001 | Taylor |
| 6,264,700 B1 | 7/2001 | Kilcoyne et al. |
| 6,285,897 B1 | 9/2001 | Kilcoyne et al. |
| 6,312,437 B1 | 11/2001 | Kortenbach |
| 6,338,345 B1 | 1/2002 | Johnson et al. |
| 6,387,104 B1 | 5/2002 | Pugsley, Jr. et al. |
| 6,409,656 B1 | 6/2002 | Sangouard et al. |
| 6,447,533 B1 | 9/2002 | Adams |
| 6,494,888 B1 | 12/2002 | Laufer et al. |
| 6,520,974 B2 | 2/2003 | Tanner et al. |
| 6,535,764 B2 | 3/2003 | Imran et al. |
| 6,544,291 B2 | 4/2003 | Taylor |
| 6,558,400 B2 | 5/2003 | Deem et al. |
| 6,558,429 B2 | 5/2003 | Taylor |
| 6,593,596 B1 | 7/2003 | Nanishi et al. |
| 6,595,911 B2 | 7/2003 | LoVuolo |
| 6,626,916 B1 | 9/2003 | Yeung et al. |
| 6,626,919 B1 | 9/2003 | Swanstrom |
| 6,675,809 B2 | 1/2004 | Stack et al. |
| 6,699,263 B2 | 3/2004 | Cope |
| 6,702,735 B2 | 3/2004 | Kelly |
| 6,736,828 B1 | 5/2004 | Adams et al. |
| 6,740,121 B2 | 5/2004 | Geitz |
| 6,746,489 B2 | 6/2004 | Dua et al. |
| 6,764,518 B2 | 7/2004 | Godin |
| 6,790,237 B2 | 9/2004 | Stinson |
| 6,845,776 B2 | 1/2005 | Stack et al. |
| 7,037,344 B2 | 5/2006 | Kagan et al. |
| 7,120,498 B2 | 10/2006 | Imran et al. |
| 7,121,283 B2 | 10/2006 | Stack et al. |
| 7,152,607 B2 | 12/2006 | Stack et al. |
| 7,175,669 B2 | 2/2007 | Geitz |
| RE39,533 E | 3/2007 | Ranoux |
| 7,220,284 B2 | 5/2007 | Kagan et al. |
| 7,244,270 B2 | 7/2007 | Lesh |
| 7,267,694 B2 | 9/2007 | Levine et al. |
| 7,288,099 B2 | 10/2007 | Deem et al. |
| 7,306,614 B2 | 12/2007 | Weller et al. |
| 7,309,341 B2 | 12/2007 | Ortiz et al. |
| 7,314,489 B2 | 1/2008 | McKenna et al. |
| 7,329,285 B2 | 2/2008 | Levine et al. |
| 7,347,875 B2 | 3/2008 | Levine et al. |
| 7,354,454 B2 | 4/2008 | Stack et al. |
| 7,371,215 B2 | 5/2008 | Colliou et al. |
| 7,483,754 B2 | 1/2009 | Imran et al. |
| 7,509,175 B2 | 3/2009 | Sparks et al. |
| 7,520,884 B2 | 4/2009 | Swanstrom et al. |
| 7,666,180 B2 | 2/2010 | Viola et al. |
| 7,753,870 B2 | 7/2010 | Demarais et al. |
| 7,780,592 B2 | 8/2010 | Tronnes |
| 7,794,447 B2 | 9/2010 | Dann et al. |
| 2001/0016748 A1 | 8/2001 | Tanner et al. |
| 2001/0020189 A1 | 9/2001 | Taylor |
| 2001/0020190 A1 | 9/2001 | Taylor |
| 2001/0044595 A1 | 11/2001 | Reydel et al. |
| 2001/0056282 A1 | 12/2001 | Sonnenschein et al. |
| 2002/0016607 A1 | 2/2002 | Bonadio et al. |
| 2002/0026214 A1 | 2/2002 | Tanner et al. |
| 2002/0035370 A1 | 3/2002 | Kortenbach |
| 2002/0040226 A1 | 4/2002 | Laufer et al. |
| 2002/0058960 A1 | 5/2002 | Hudson et al. |
| 2002/0082621 A1 | 6/2002 | Schurr et al. |
| 2002/0165589 A1 | 11/2002 | Imran et al. |
| 2002/0183768 A1 | 12/2002 | Deem et al. |
| 2002/0188354 A1 | 12/2002 | Peghini |
| 2003/0014064 A1 | 1/2003 | Blatter |
| 2003/0018358 A1 | 1/2003 | Saadat |
| 2003/0040804 A1* | 2/2003 | Stack et al. ................. 623/23.7 |
| 2003/0040808 A1 | 2/2003 | Stack et al. |
| 2003/0055313 A1 | 3/2003 | Anderson et al. |
| 2003/0055442 A1 | 3/2003 | Laufer et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0120285 A1 | 6/2003 | Kortenbach |
| 2003/0130560 A1 | 7/2003 | Suzuki et al. |
| 2003/0130561 A1 | 7/2003 | Suzuki et al. |
| 2003/0139752 A1 | 7/2003 | Pasricha et al. |
| 2003/0171775 A1 | 9/2003 | Belson |
| 2003/0181929 A1 | 9/2003 | Geitz |
| 2003/0191497 A1 | 10/2003 | Cope |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2004/0002734 A1 | 1/2004 | Fallin et al. |
| 2004/0024427 A1 | 2/2004 | Imran et al. |
| 2004/0039452 A1 | 2/2004 | Bessler |
| 2004/0044364 A1 | 3/2004 | DeVries et al. |
| 2004/0059349 A1 | 3/2004 | Sixto, Jr. et al. |
| 2004/0059354 A1 | 3/2004 | Smith et al. |
| 2004/0082963 A1 | 4/2004 | Gannoe et al. |
| 2004/0087976 A1 | 5/2004 | DeVries et al. |
| 2004/0087977 A1 | 5/2004 | Nolan et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0093065 A1 | 5/2004 | Yachia et al. |
| 2004/0097986 A1 | 5/2004 | Adams |
| 2004/0097987 A1 | 5/2004 | Pugsley et al. |
| 2004/0102855 A1 | 5/2004 | Shank |
| 2004/0107004 A1 | 6/2004 | Levine et al. |
| 2004/0116949 A1 | 6/2004 | Ewers et al. |
| 2004/0117031 A1 | 6/2004 | Stack et al. |
| 2004/0122453 A1 | 6/2004 | Deem et al. |
| 2004/0122456 A1 | 6/2004 | Saadat et al. |
| 2004/0122473 A1 | 6/2004 | Ewers et al. |
| 2004/0133089 A1 | 7/2004 | Kilcoyne et al. |
| 2004/0133147 A1 | 7/2004 | Woo |
| 2004/0133219 A1 | 7/2004 | Forsell |
| 2004/0133238 A1 | 7/2004 | Cerier |
| 2004/0138525 A1 | 7/2004 | Saadat et al. |
| 2004/0138529 A1 | 7/2004 | Wiltshire et al. |
| 2004/0138761 A1 | 7/2004 | Stack et al. |

| | | |
|---|---|---|
| 2004/0143342 A1 | 7/2004 | Stack et al. |
| 2004/0147958 A1 | 7/2004 | Lam et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162567 A9 | 8/2004 | Adams |
| 2004/0162568 A1 | 8/2004 | Saadat et al. |
| 2004/0167546 A1 | 8/2004 | Saadat et al. |
| 2004/0181242 A1 | 9/2004 | Stack et al. |
| 2004/0186514 A1 | 9/2004 | Swain et al. |
| 2004/0193190 A1 | 9/2004 | Liddicoat et al. |
| 2004/0199189 A1 | 10/2004 | Gifford et al. |
| 2004/0204768 A1 | 10/2004 | Geitz |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0243195 A1 | 12/2004 | Imran et al. |
| 2004/0249362 A1 | 12/2004 | Levine et al. |
| 2004/0249367 A1 | 12/2004 | Saadat et al. |
| 2005/0033240 A1 | 2/2005 | Oishi et al. |
| 2005/0033331 A1 | 2/2005 | Burnett et al. |
| 2005/0033332 A1 | 2/2005 | Burnett |
| 2005/0049718 A1 | 3/2005 | Dann et al. |
| 2005/0065401 A1 | 3/2005 | Saadat et al. |
| 2005/0075653 A1 | 4/2005 | Saadat et al. |
| 2005/0075654 A1 | 4/2005 | Kelleher |
| 2005/0080431 A1 | 4/2005 | Levine et al. |
| 2005/0080444 A1 | 4/2005 | Kraemer et al. |
| 2005/0085787 A1 | 4/2005 | Laufer |
| 2005/0085900 A1 | 4/2005 | Case et al. |
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0101977 A1 | 5/2005 | Gannoe et al. |
| 2005/0125020 A1 | 6/2005 | Meade et al. |
| 2005/0125075 A1 | 6/2005 | Meade et al. |
| 2005/0143784 A1 | 6/2005 | Imran |
| 2005/0177181 A1 | 8/2005 | Kagan et al. |
| 2005/0187567 A1 | 8/2005 | Baker et al. |
| 2005/0192629 A1 | 9/2005 | Jaadat et al. |
| 2005/0197714 A1 | 9/2005 | Sayet |
| 2005/0197715 A1 | 9/2005 | Kugler et al. |
| 2005/0203547 A1 | 9/2005 | Weller et al. |
| 2005/0222592 A1 | 10/2005 | Gannoe et al. |
| 2005/0228413 A1 | 10/2005 | Binmoeller et al. |
| 2005/0228504 A1 | 10/2005 | Demarais |
| 2005/0247320 A1 | 11/2005 | Stack et al. |
| 2005/0256587 A1 | 11/2005 | Egan |
| 2005/0261549 A1 | 11/2005 | Hewit et al. |
| 2005/0261712 A1 | 11/2005 | Balbierz et al. |
| 2005/0267499 A1 | 12/2005 | Stack et al. |
| 2005/0267595 A1 | 12/2005 | Chen et al. |
| 2006/0009858 A1 | 1/2006 | Levine et al. |
| 2006/0015125 A1 | 1/2006 | Swain |
| 2006/0020164 A1 | 1/2006 | Butler et al. |
| 2006/0020247 A1 | 1/2006 | Kagan et al. |
| 2006/0020277 A1 | 1/2006 | Gostout et al. |
| 2006/0020278 A1 | 1/2006 | Burnett et al. |
| 2006/0025819 A1 | 2/2006 | Nobis et al. |
| 2006/0047289 A1 | 3/2006 | Fogel |
| 2006/0064120 A1 | 3/2006 | Levine et al. |
| 2006/0074458 A1 | 4/2006 | Imran |
| 2006/0155312 A1 | 7/2006 | Levine et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0173422 A1 | 8/2006 | Reydel et al. |
| 2006/0206063 A1 | 9/2006 | Kagan et al. |
| 2006/0206064 A1 | 9/2006 | Kagan et al. |
| 2006/0217762 A1 | 9/2006 | Maahs et al. |
| 2006/0235446 A1 | 10/2006 | Godin |
| 2006/0253126 A1 | 11/2006 | Bjerken et al. |
| 2006/0264982 A1 | 11/2006 | Viola et al. |
| 2006/0265082 A1 | 11/2006 | Meade et al. |
| 2006/0287734 A1 | 12/2006 | Stack et al. |
| 2006/0293742 A1 | 12/2006 | Dann et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0016244 A1 | 1/2007 | Behl et al. |
| 2007/0027548 A1 | 2/2007 | Levine et al. |
| 2007/0027549 A1 | 2/2007 | Godin |
| 2007/0032879 A1 | 2/2007 | Levine et al. |
| 2007/0083271 A1 | 4/2007 | Levine et al. |
| 2007/0106233 A1 | 5/2007 | Huang et al. |
| 2007/0106313 A1 | 5/2007 | Golden et al. |
| 2007/0129719 A1 | 6/2007 | Kendale et al. |
| 2007/0156248 A1 | 7/2007 | Marco et al. |
| 2007/0208360 A1 | 9/2007 | Demarais et al. |
| 2007/0225555 A1 | 9/2007 | Stefanchik |
| 2007/0233162 A1 | 10/2007 | Gannoe et al. |
| 2007/0293885 A1 | 12/2007 | Binmoeller |
| 2008/0004606 A1 | 1/2008 | Swain et al. |
| 2008/0033574 A1 | 2/2008 | Bessler et al. |
| 2008/0058887 A1 | 3/2008 | Griffin et al. |
| 2008/0103604 A1 | 5/2008 | Levine et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0208356 A1 | 8/2008 | Stack et al. |
| 2008/0269797 A1 | 10/2008 | Stack et al. |
| 2009/0012541 A1 | 1/2009 | Dahl et al. |
| 2009/0012544 A1 | 1/2009 | Thompson et al. |
| 2009/0012553 A1 | 1/2009 | Swain et al. |
| 2009/0024143 A1 | 1/2009 | Crews et al. |

FOREIGN PATENT DOCUMENTS

| | | |
|---|---|---|
| EP | 1237501 | 9/2000 |
| WO | WO 80/00007 | 1/1980 |
| WO | WO 91/01117 A1 | 2/1991 |
| WO | WO 96/29954 A1 | 10/1996 |
| WO | WO 99/60931 A1 | 12/1999 |
| WO | WO 00/12027 A1 | 3/2000 |
| WO | WO 01/35834 A1 | 5/2001 |
| WO | WO 01/43663 A1 | 6/2001 |
| WO | WO 01/85034 A1 | 11/2001 |
| WO | WO 02/094132 A1 | 11/2002 |
| WO | WO 02/102227 A2 | 12/2002 |
| WO | WO 03/017882 A2 | 3/2003 |
| WO | WO 03/086246 A1 | 10/2003 |
| WO | WO 03/086247 A1 | 10/2003 |
| WO | WO 03/094785 A1 | 11/2003 |
| WO | WO 2004/017863 A2 | 3/2004 |
| WO | WO 2004/021894 A1 | 3/2004 |
| WO | WO2004/041119 A2 | 5/2004 |
| WO | WO 2004/047686 A1 | 6/2004 |
| WO | WO 2004/049982 A2 | 6/2004 |
| WO | WO 2004/064680 A1 | 8/2004 |
| WO | WO 2004/064685 A1 | 8/2004 |
| WO | WO 2004/080336 A2 | 9/2004 |
| WO | WO 2004/087014 A2 | 10/2004 |
| WO | WO 2004/087233 A2 | 10/2004 |
| WO | WO 2004/086984 A1 | 11/2004 |
| WO | WO 2004/103214 A1 | 12/2004 |
| WO | WO 2004/103214 A2 | 12/2004 |
| WO | WO 2004/103430 A2 | 12/2004 |
| WO | WO 2004/105643 A1 | 12/2004 |
| WO | WO 2005/011463 A2 | 2/2005 |
| WO | WO 2005/011519 | 2/2005 |
| WO | WO 2005/011519 A2 | 2/2005 |
| WO | WO 2005/032422 | 4/2005 |
| WO | WO 2005/037152 A1 | 4/2005 |
| WO | WO 2005/060869 A1 | 7/2005 |
| WO | WO 2005/060882 A1 | 7/2005 |
| WO | WO 2006/044640 A1 | 4/2006 |
| WO | WO 2006/161265 A1 | 4/2006 |

OTHER PUBLICATIONS

Endoscopic Suturing of a Novel Gastroesophageal Antireflux Device (GARD) A Prelinary Report, N. J. Godin et al., *Gastrointestinal Endoscopy*, vol. 43, No. 4, 1996.

An endoscopic stapling device: the development of new flexible endoscopically controlled device for placing multiple transmural staples in gastrointestinal tissue, C. Paul Swain, MD et al.,

*Gastrointestinal Endoscopy*, vol. 35, No. 4, 1989 pp. 338-339.
An endoscopically deliverable tissue-transfixing device for securing biosensors in the gastrointestinal tract, C. Paul Swain, MD et al. *Gastrointestinal Endoscopy*, 1994 vol. 40 No. 6 pp. 730-734.
*Development of a gastroplasty with variable diameter. Experimental study using artificial sphincters*, M. Merlini et al., 1992 Abstract.
A through-the-scope device of suturing and tissue approximation under EUS control, Annette Fritscher-Ravens, MD, et al., *Gastrointestinal Endoscopy*, vol. 56, No. 5, 2002, pp. 737-742.
Bard EndoCinch: the device, the technique and pre-clinical studies, Paul Swain, M.D. et al., *Gastrointestinal Endoscopy Clinics of North America*, 13, 2003 pp. 75-88.
Microvasive gastric stapler: the device, technique, and preclinical results, Tom R. De Meester MD, *Gastrointestinal Endoscopy Clinics of North America*, 13 (2003) pp. 117-133.
Transgastric gastropexy and hiatal hernia repair for GERD under EUS control: a porcine model, Annette Fritscher-Ravens, MD et al., *Gastrointestinal Endoscopy*, vol. 59, No. 1, 2004, pp. 89-95.
Sew-Right® SR 5™ & SR 10™, Ti-KNOT® TK 5™ Advertisement received at ASBS Conference 2002.
PCT International Search Report for PCT/US2005/15795 mailed Nov. 14, 2005.
U.S. Appl. No. 11/431,040, filed May 2006, Kagan et al.
U.S. Appl. No. 11/548,605, filed Oct. 2006, Dann et al.
Antireflux operations at flexible endoscopy using endoluminal stitching techniques: an experimental study, Sritharan S. Kadirkamanathan et al., *Gastrointestinal Endoscopy*, vol. 44, No. 2, 1995 pp. 133-143.
Progression rate of self-propelled feeding tubes in critically ill patients, Mette M. Berger et al., *Intensive Care Med* Oct. 29, 2002, pp. 1768-1774.
Iatrogenic Intussusception: a Complication of Long Intestinal Tubes, Patricia Redmond, M.D., et al., *American Jounal of Gastroenterology*, vol. 77, No. 1, 1982, pp. 39-42.
Design and Testing of a New, Small Diameter, Single Stitch Endoscopic Sewing Machine, C.P. Swain et al., *Abstracts Submitted to A/S/G/E/ 1990*, Vo. 36, No. 2, 1990, pp. 213, 214.
Synthetic Biodegradable Polymers as Medical Devices, John C. Middleton et al., *Medical Plastics and Biomaterials Magazine MPS Article Index*, Mar. 1998.
*Experimental study on in situ tissue engineering of the stomach by an acellular collagen sponge scaffold graft*, Hori Y. Nakamura et al., Abstract, May 2001.
*Repair of Full-Thickness Defects in Alimentary Tract Wall with Patches of Expanded Polytetrafluoroethylene*, Daniel S. Oh, MD et al., Annals of Surgery 2002; 235:708-712.
*Stents in the small intestine*, Singh S, Gagneja HK, Abstract, Oct. 2002.
Endoscopic vertical band gastroplasty with an endoscopic sewing machine, Amjad N. Awan MD et al., *Gastrointestinal Endoscopy*, vol. 55, No. 2, 2002, pp. 254-256.
*Evaluation of porcine-derived small intestine submucosa as a biodegradable graft for gastrointestinal healing*, SG del la Fuente et al., Abstract, J. Gastrointest Surg Jan. 2003.
Endoscopic suturing for gastrosphageal reflux disease: clinical outcome with the Bard Endocinch, Richard I. Rothstein, MD et al., *Gastrointestinal Endoscopy Clinics of North America*, 13 (2003) pp. 89-101.
Wilson-Cook sewing device: the device, technique, and preclinical studies, Michael Rosen MD, et al., *Gastrointestinal Endoscopy Clinics of North America*, 13 (2003) pp. 103-108.
Endoscopic full-thickness plication: the device, technique, pre-clinical and early clinical experience, Ram Chuttani, MD, *Gastrointestinal Endoscopy Clinics of North America*, 13 (2003) pp. 109-116.
Endoscopic Gastropexy and Crural Repair for Gastro-Esophageal Reflux: Transgastric Surgery Under Endoscopic Ultrasound Control II, Anette Fritscher-Ravens et al. *Digestive Disease Week* 2003 Abstract.

Endoscopic suturing for treatment of GERD, m. Brian Fennerty, MD, *Gastrointestinal Endoscopy*, vol. 57, No. 3, 2003 pp. 390-395.
Effect of Duodenal-Jejunal Exclusion of a Non-obese Animal Model of Type 2 Diabetes, Francesco Rubino, MD et al., *Annals of Surgery*, vol. 239, No. 1, Jan. 2004, pp.
*The LAP-BAND Solution*, BioEnterics Corporation, Brochurehttp://www.bioenterics.com/.
*Successful Uses in Approximation Ligation & Fixation using the QUIK-STITCH, Endoscopic Suturing System*, Paré Surgical, Inc. Brochure 2001.
*Obesity Treatment*, Medical Innovation Developpement, Brochure.
*The Bard EndoCinch Procedure*, Introducing Endoscopic Technology for the Treatment of GERD.
*Microvasive WALLSTENT® Colonic and Duodenal Endoprosthesis*, Boston Scientific website, www.bostonscientific.com, Sep. 20, 2002.
*COOK® Wilson-Cook Medical GI Endoscopy*, Wilson Cook: Biliary/Pancreatic Stents, www.cookgroup.com, Sep. 20, 2002.
*Bioabsorbable Polymers*, William B. Gleason, University of Minnesota, 1998.
*Cope Gastrointestinal Suture Anchor Set*, www.cookgroup.com, Cook Diagnostic and Interventional Products Advertisement 2000.
*LSI Solutions®*, SEW-RIGHT® SR 5, Advertisement received at ASBS Conference 2002.
Three-dimensional manometric imaging of the lower esophageal sphincter, Hubert J. Stein, Md. *Surgery*, 1995 vol. 117 No. 6 pp. 692-698.
A new method of enteroscopy—The double-balloon method, Yamamoto et al., *Can J. Gastroenterol*, vol. 17, No. 4 Apr. 2003, pp. 273-274.
Radiocontrolled Movement of a Robot Endoscope in the Human Gastrointestinal Tract, Paul Swain et al., Abstract—*Gastrointestinal Endoscopy*, vol. 61, No. 5 DDW Abstract Issue: Apr. 2005.
Techniques for Advancing Guide Wires and Devices in the Lumen of the Gastrointestinal Tract, Long et al., *Gastrointestial Endoscopy*, vol. 57, No. 5 Apr. 2003 Abstract, 2003 ASGE Meeting, May 18-21, Orlando Florida.
PCT International Search Report, PCT/US2003/34822 mailed Feb. 4, 2004.
PCT International Search Report, PCT/US2004/44049 mailed May 30, 2007.
Notice of Allowance, U.S. Appl. No. 11/400,724 mailed Sep. 20, 2010 in 7 pages.
Notice of Allowance, U.S. Appl. No. 11/430,677 mailed Sep. 23, 2010 in 7 pages.
Notice of Allowance, U.S. Appl. No. 11/430,274 mailed Sep. 30, 2010 in 8 pages.
Fobi, M.D., Mathais A.L. et al., "Gastric Bypass Operation for Obesity", World J. Surg., Sep. 1998, vol. 22, pp. 925-935.
Pories, M.D., Walter J. et al., "Who Would Have Thought It? An Operation Proves to be the Most Effective Therapy for Adult-Onset Diabetes Mellitus", Annals of Surgery, Sep. 1995, vol. 222, No. 3, pp. 339-352.
Sugerman, M.D., Harvey J. et al., "Weight Loss With Vertical Banded Gastroplasty and Roux-Y Gastric Bypass for Morbid Obesity With Selective Versus Random Assignment", The American Journal of Surgery, Jan. 1989, vol. 157, pp. 93-102.
Keyser, M.D., Eric J. et al., "Double Closed Loop Obstruction and Perforation in a Previous Roux-en-Y Gastric Bypass", Obesity Surgery, 1998, vol. 8, pp. 475-479.
Oh, M.D., Chung H. et al., "Weight Loss Following Transected Gastric Bypass with Proximal Roux-en-Y", Obesity Surgery, 1997, vol. 7, pp. 142-147.
Crampton, MBBS, Nicholas A., et al., "Silastic Ring Gastric Bypass: Results in 64 Patients", Obesity Surgery, 1997, vol. 7, pp. 489-493.

* cited by examiner

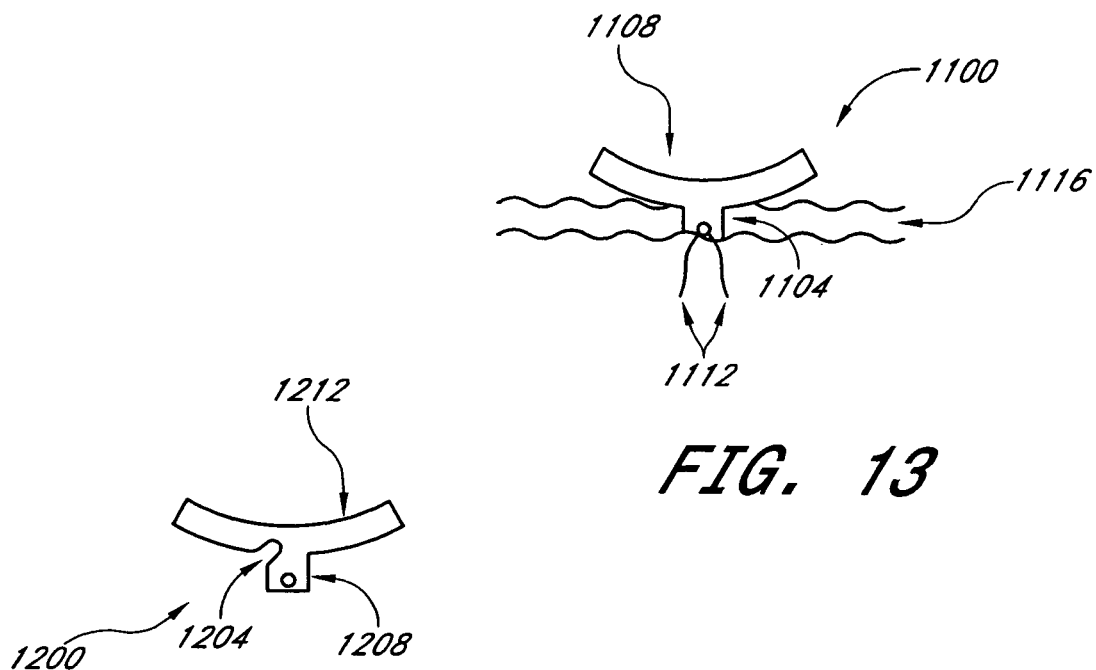
FIG. 13
FIG. 14
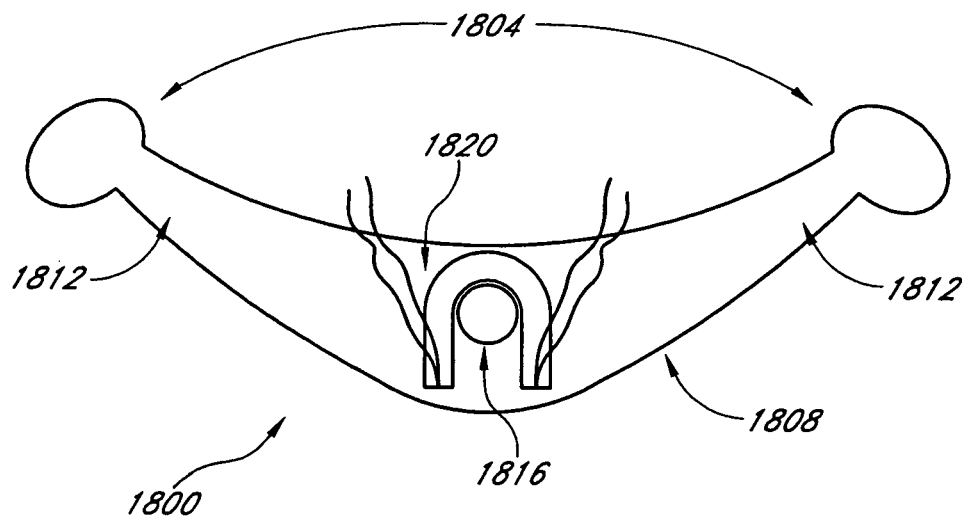
FIG. 20

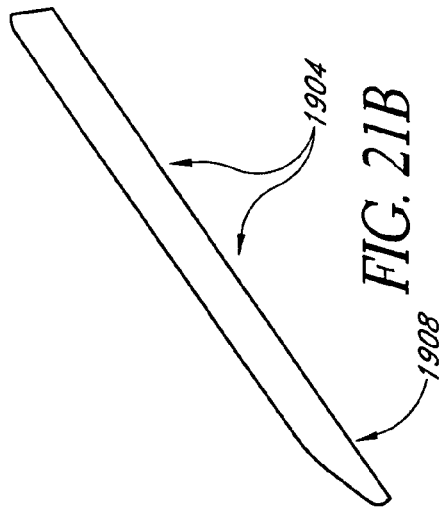
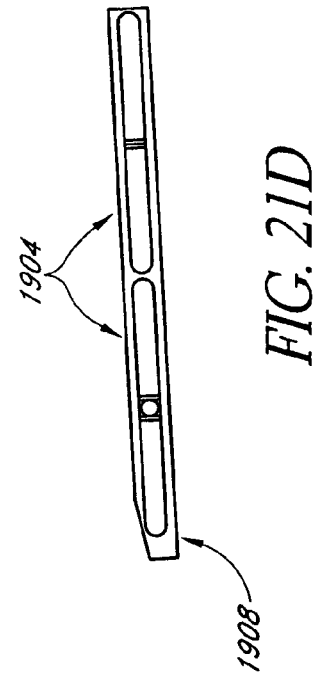
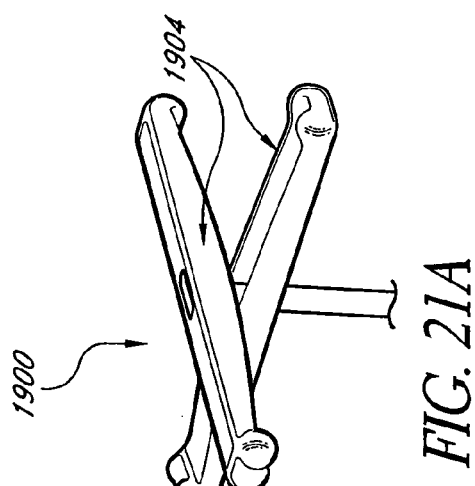
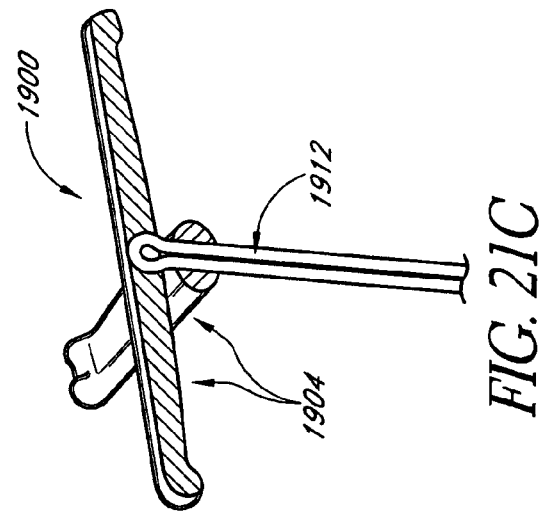

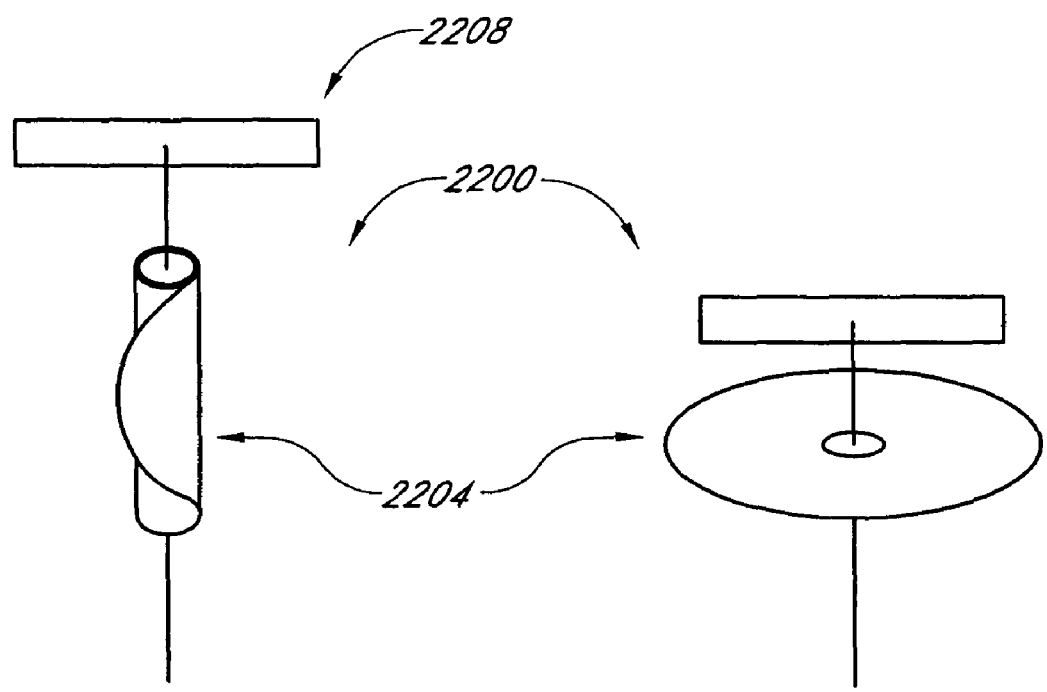
*FIG. 23A*  *FIG. 23B*
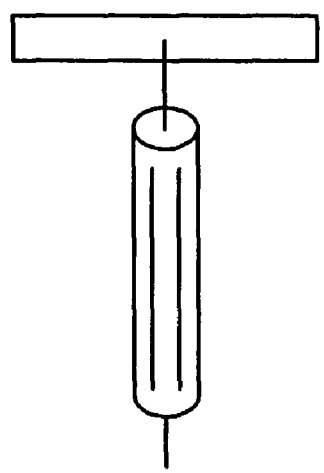   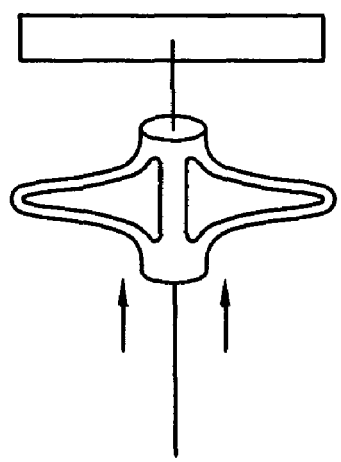
*FIG. 24A*  *FIG. 24B*

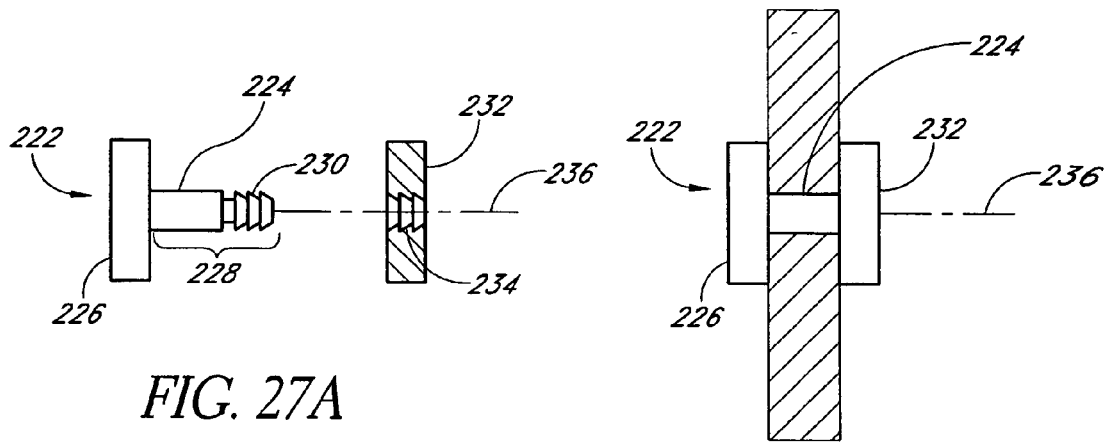
FIG. 27A
FIG. 27B
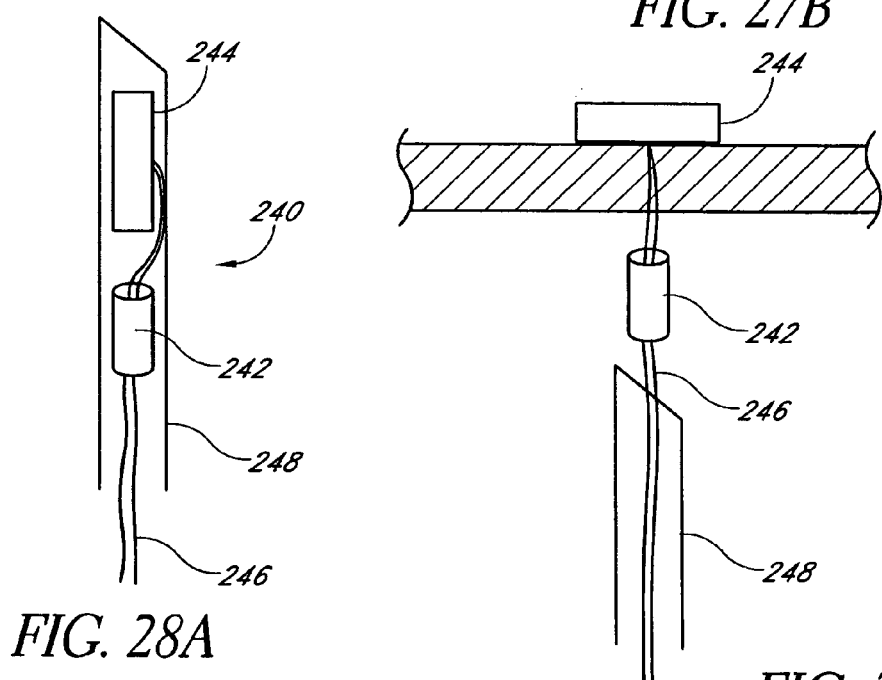
FIG. 28A
FIG. 28B
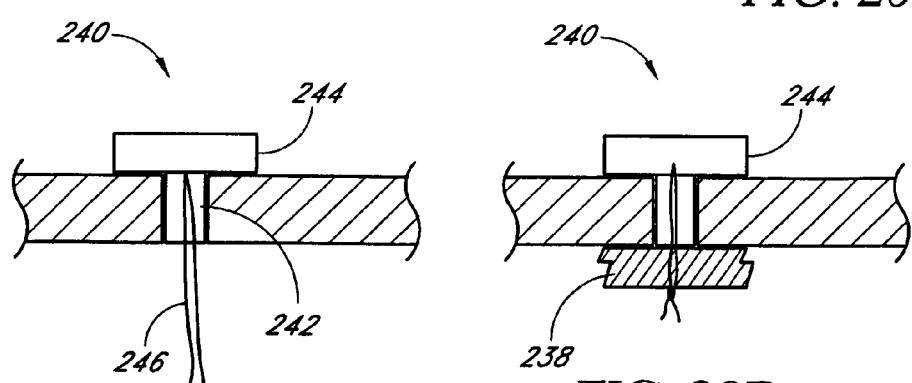
FIG. 28C
FIG. 28D

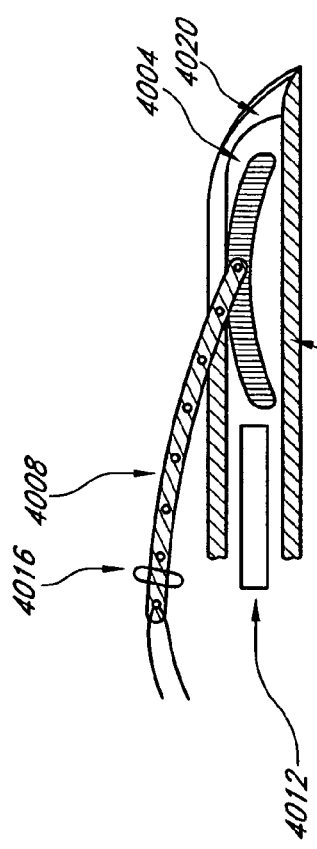
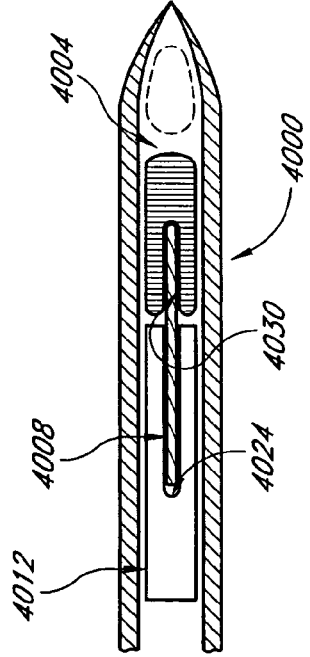
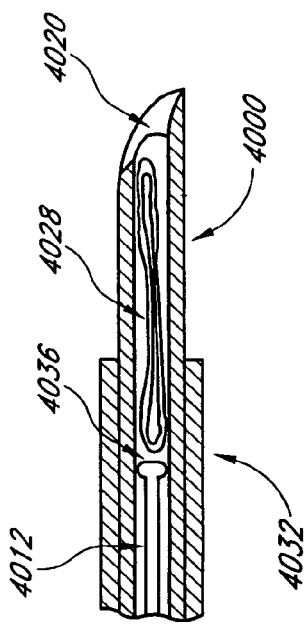
FIG. 32A
FIG. 32B
FIG. 32C

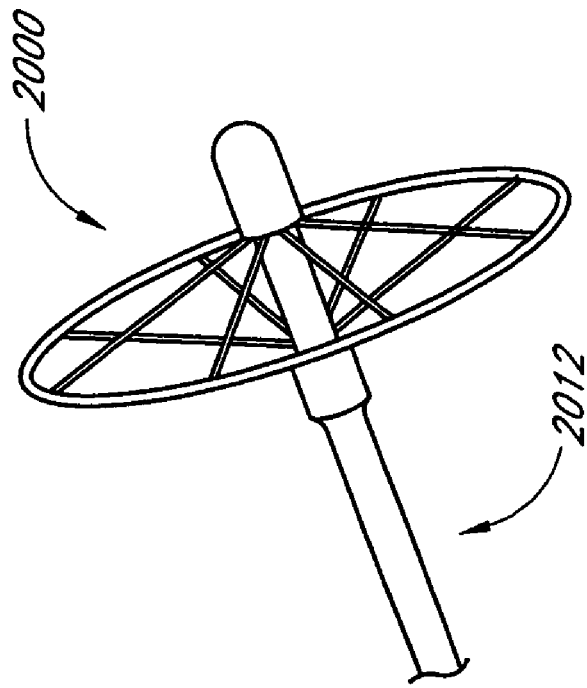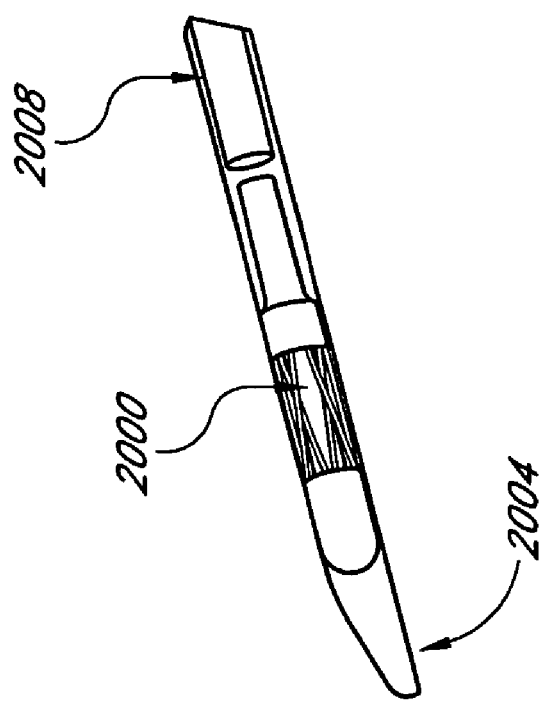
FIG. 34

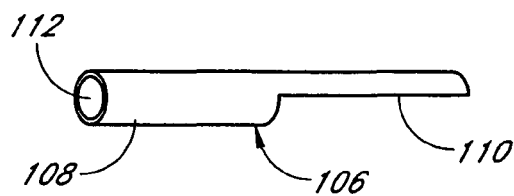
FIG. 37A
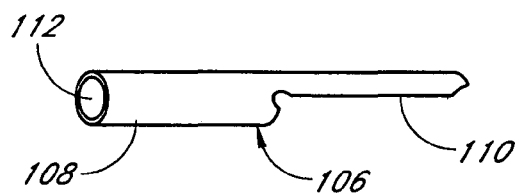
FIG. 37B
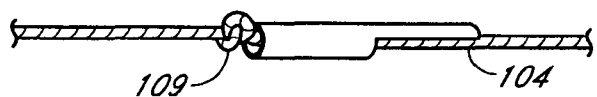
FIG. 37C
FIG. 37D
FIG. 37E
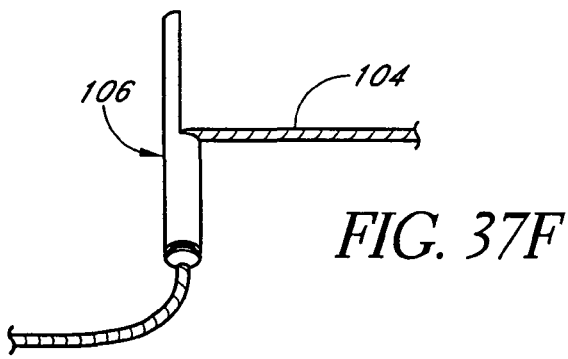
FIG. 37F
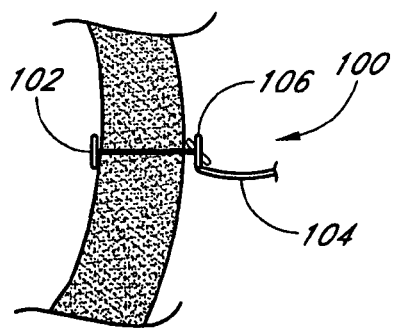
FIG. 37G

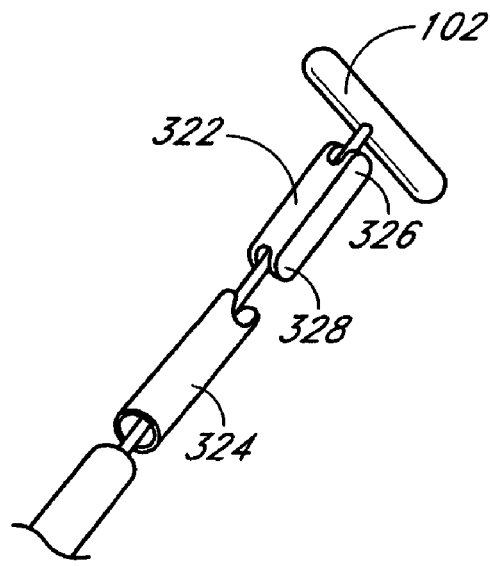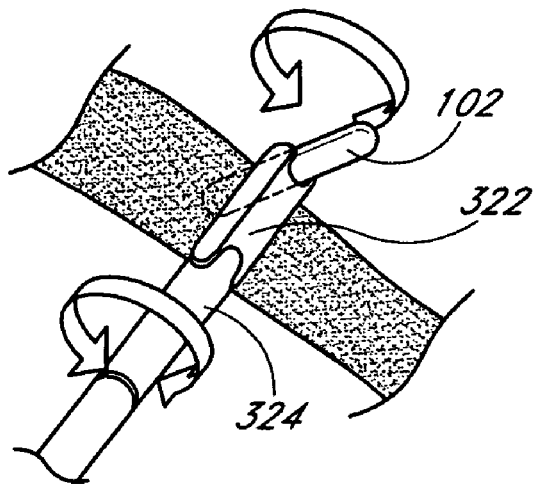
FIG. 52A  FIG. 52B
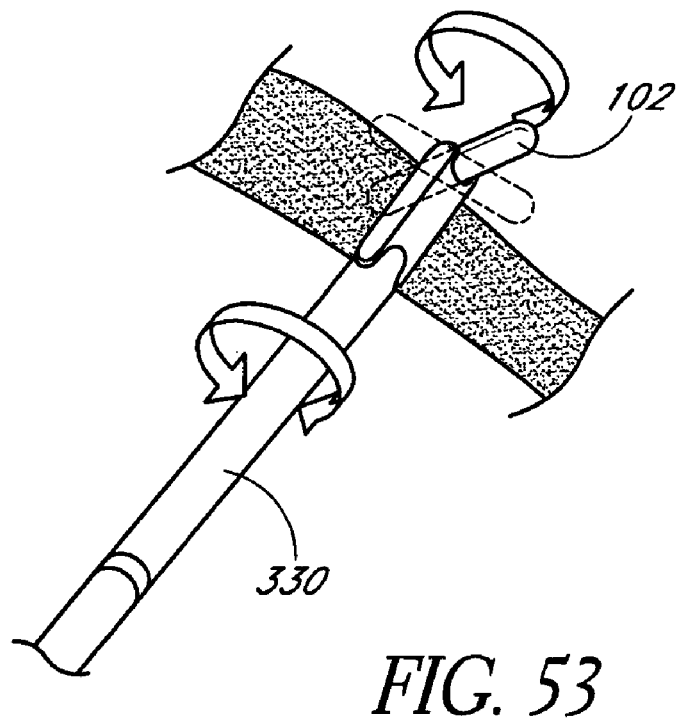
FIG. 53

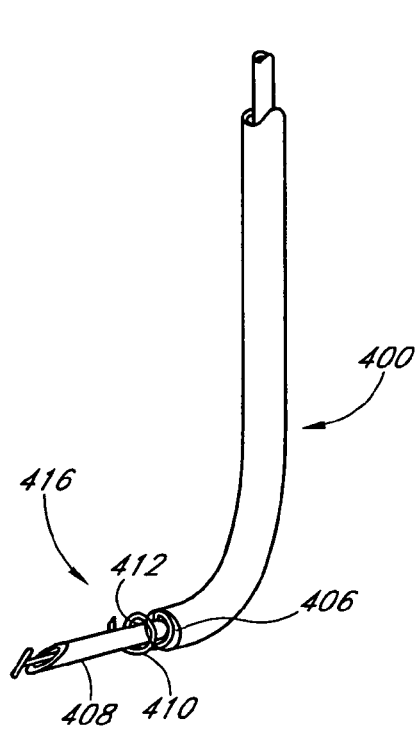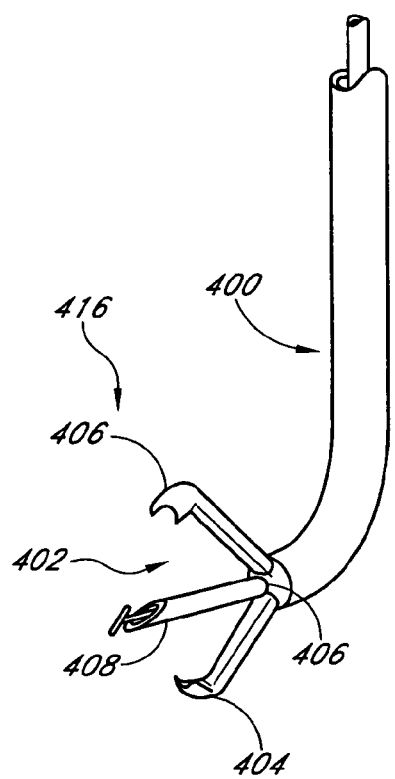
FIG. 54B    FIG. 54A
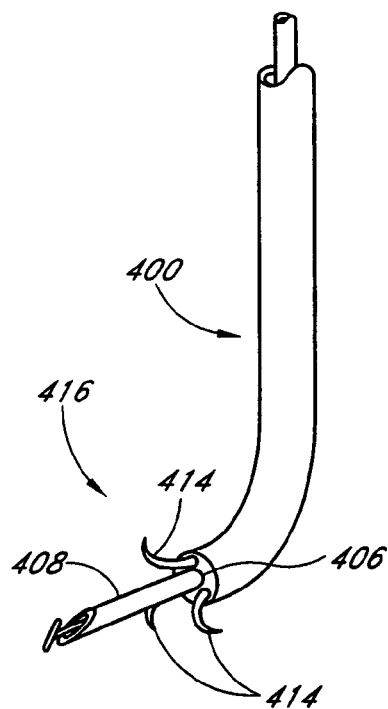
FIG. 54C

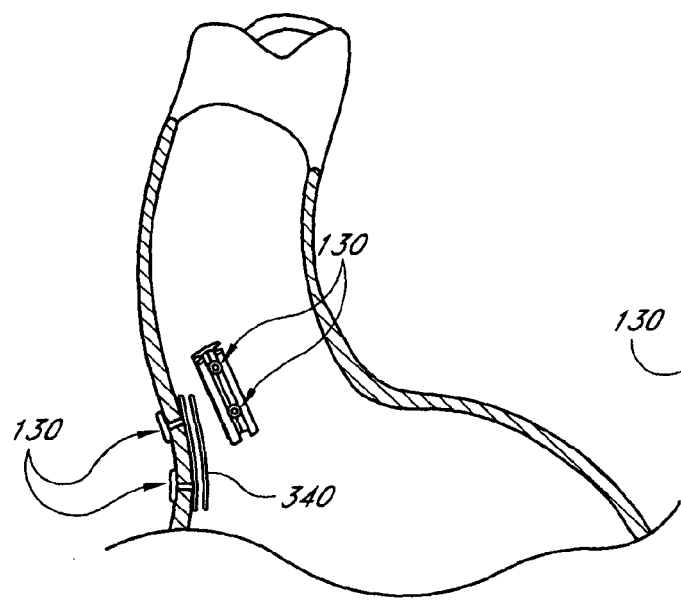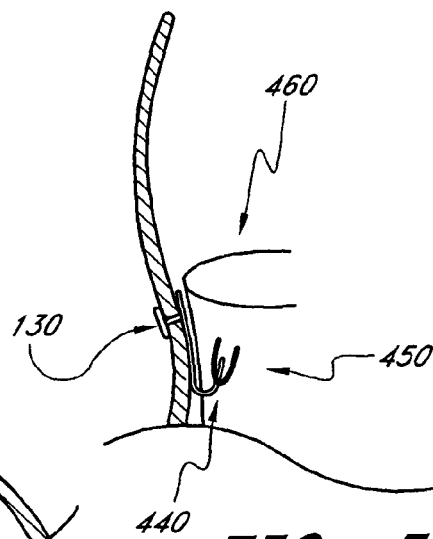
FIG. 57A
FIG. 57B
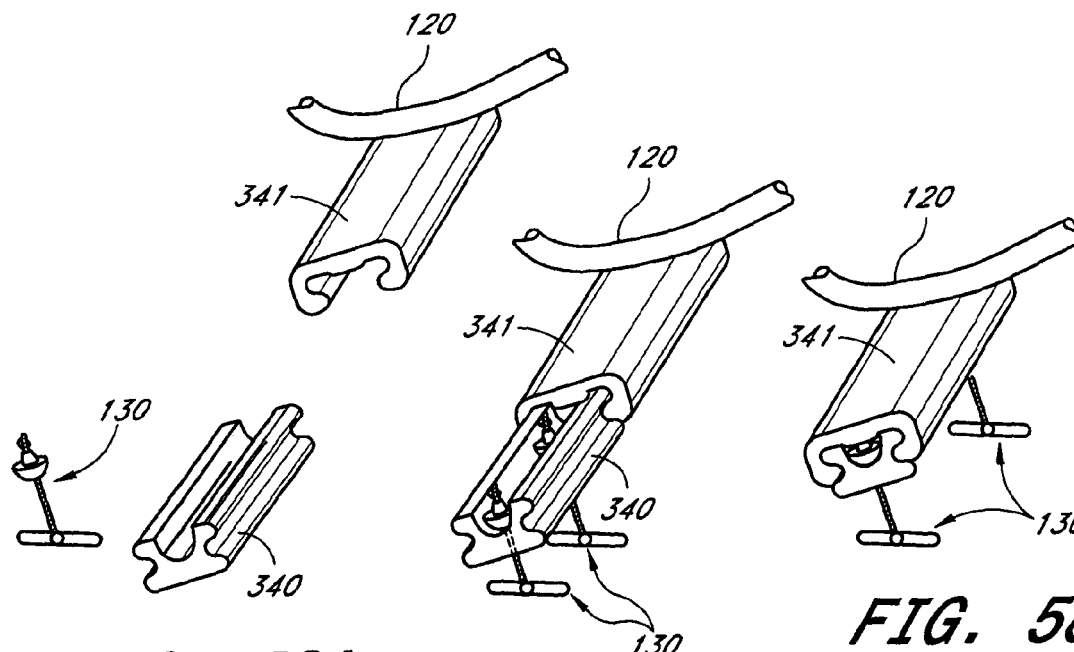
FIG. 58A
FIG. 58B
FIG. 58C

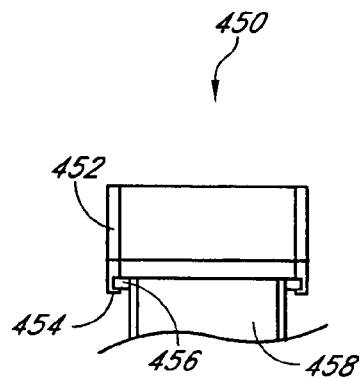
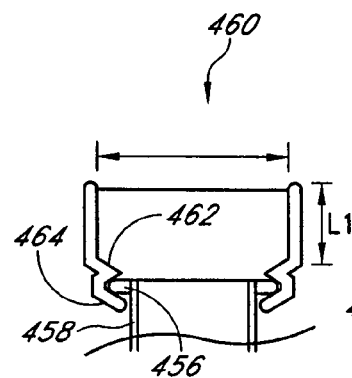
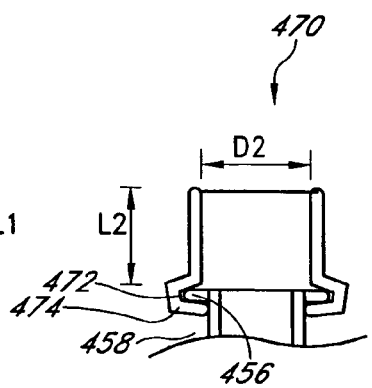
FIG. 61A    FIG. 62A    FIG. 63A
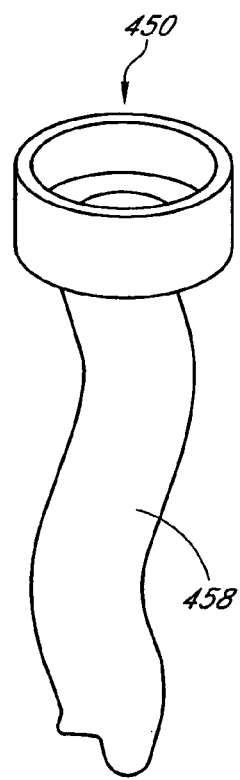
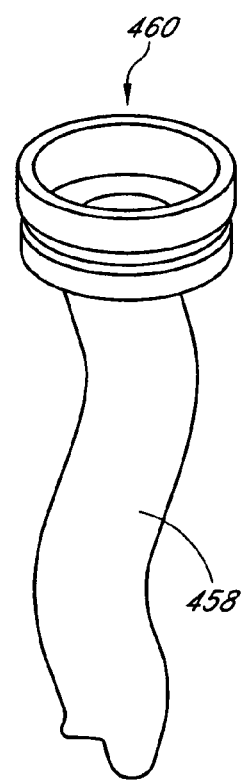
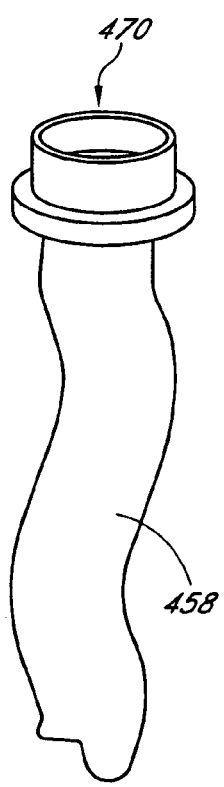
FIG. 61B    FIG. 62B    FIG. 63B

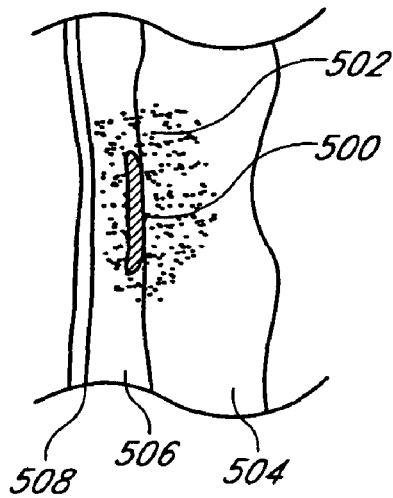
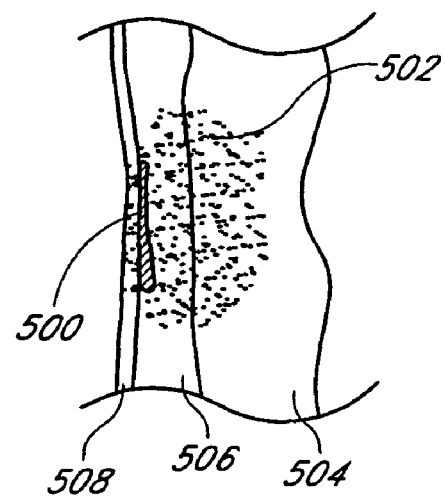
FIG. 68
FIG. 69
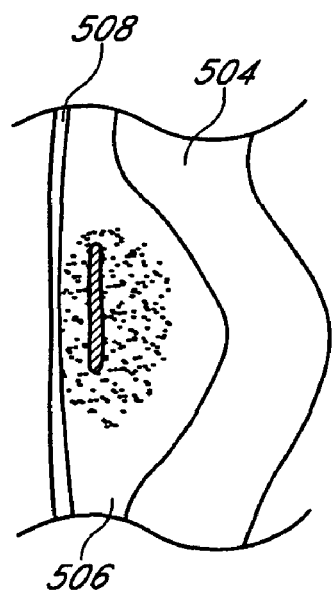
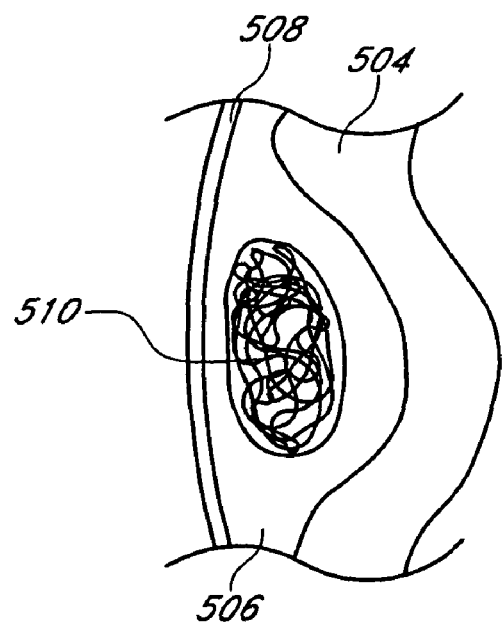
FIG. 70
FIG. 71

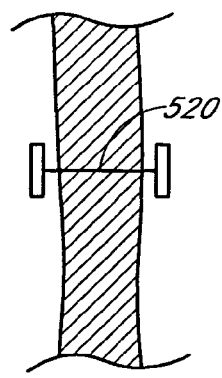 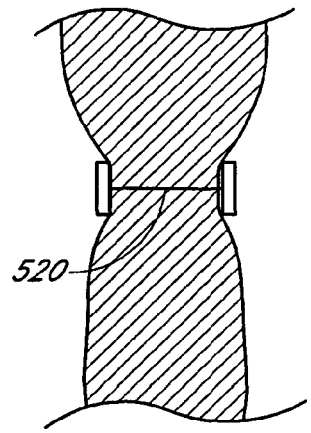 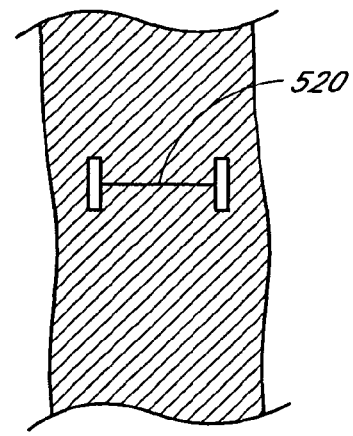
FIG. 72A          FIG. 72B          FIG. 72C
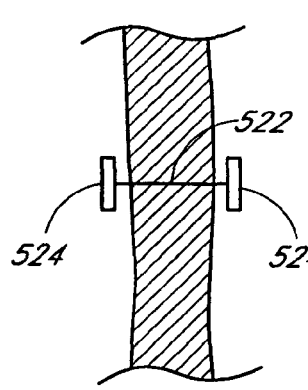 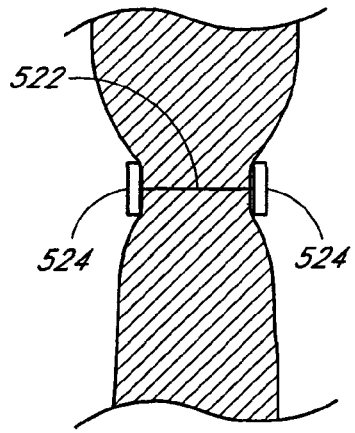 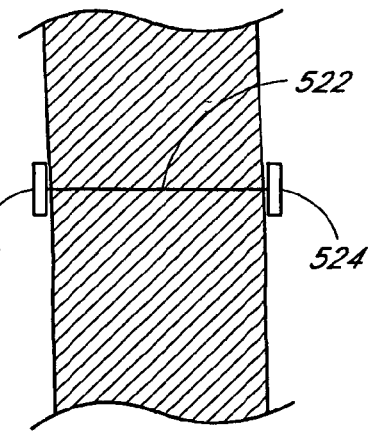
FIG. 73A          FIG. 73B          FIG. 73C

DEVICES AND METHODS FOR ATTACHING AN ENDOLUMENAL GASTROINTESTINAL IMPLANT

CROSS REFERENCE TO RELATED APPLICATIONS

This patent application claims the benefit of U.S. provisional patent application 60/569,442, filed on May 7, 2004, by Kagan et al. for Devices and Methods for Treating Morbid Obesity and U.S. provisional patent application 60/613,917, filed on Sep. 27, 2004, by Kagan et al. for Devices and Methods for Attachment of a Gastrointestinal Sleeve. This patent application is also a continuation-in-part of U.S. utility patent application Ser. No. 10/698,148, filed on Oct. 31, 2003 by Kagan et al. for Apparatus and Methods for Treatment of Morbid Obesity which claims priority to U.S. provisional patent applications 60/480,485 filed Jun. 21, 2003, 60/448,817 filed Feb. 21, 2003, 60/437,513 filed Dec. 30, 2002, 60/430,857 filed Dec. 3, 2002, 60/428,483 filed Nov. 22, 2002, and 60/422,987 filed Nov. 1, 2002. This patent application is also a continuation-in-part of U.S. utility patent application Ser. No. 10/998,424, filed on Nov. 29, 2004 now abandoned by Kagan et al. for Apparatus and Methods for Treatment of Morbid Obesity and of U.S. utility patent application Ser. No. 11/025,364, filed on Dec. 29, 2004, by Kagan et al. for Devices and Methods for Treating Morbid Obesity. The devices and methods described herein can be combined with and/or used in conjunction with the apparatus and methods described in these prior applications. These and all patents and patent applications referred to herein are hereby expressly incorporated by reference in their entireties herein.

BACKGROUND OF THE INVENTION

1. Field of the Invention

The present invention relates generally to apparatus and methods for treatment of obesity, and particularly morbid obesity. In particular, the present invention relates to devices and methods for attachment of a gastrointestinal sleeve device within a patient's digestive tract for treatment of obesity.

2. Description of the Related Art

Gastrointestinal sleeve devices for treatment of obesity have been described in the prior applications listed above, as have various devices and methods for attachment of a gastrointestinal sleeve device within a patient's digestive tract. The present invention is the result of continued investigation into devices and methods for attachment of a gastrointestinal sleeve device within a patient's digestive tract.

SUMMARY OF THE INVENTION

There is provided in accordance with one aspect of the present invention, an attachment system for attaching a device to the mucosal side of a wall of the gastrointestinal tract. The wall comprises, among other tissue layers, a muscularis layer and a serosal layer. The system comprises a gastrointestinal attachment cuff having a tubular body, a proximal end and a distal end. At least one attachment structure (sometimes referred to as a tissue anchor) is provided for transmural attachment of the cuff to the mucosal side. The anchor comprises a connecting element (sometimes referred to as a tension element) for extending through the wall and at least one transverse retention surface for positioning in contact with the serosal tissue. The cuff may be a unitary annular component or assembly, or may comprise two or three or more components spaced circumferentially apart about a longitudinal axis.

The tension element may comprise a suture. The tension element comprises a proximal end for extending through the mucosal layer and a distal end for carrying the transverse retention surface. The transverse retention surface comprises a proximal surface of a serosal anchor. The serosal anchor may comprise a T-tag, a disk, or an inflatable structure. The serosal anchor is transformable between a first, reduced profile for distal transmural advancement through the wall, and a second, enlarged profile for resisting proximal retraction through the wall.

The tension element has a length between the cuff and the transverse retention surface, and the length is generally at least about 2 mm and often no more than about 20 mm. In some implementations of the invention, the length is within the range from about 2 mm to about 10 mm and, depending on the patient, potentially within the range from about 3 mm to about 6 mm. Preferably, the connecting element is at least as long as the uncompressed wall thickness of the tissue at the attachment point.

The attachment system may additionally comprise a first engagement surface carried by a first coupler on the attachment cuff for coupling to a second, complementary engagement surface carried by a second coupler on a gastric bypass tube. The first and second couplers may be configured for removable coupling or permanent coupling between the bypass tube and the cuff. The bypass tube may have a length of at least about 50 cm, at least about 75 cm and in certain embodiments at least about 100 cm. The system may comprise at least 6 tissue anchors, and, in some applications, at least 12 tissue anchors.

The cuff may be omitted and the proximal end of the bypass tube may be attached directly to the adjacent tissue. The use of a cuff may be preferred, however, if removal or replacement of the bypass tube is contemplated, or if it is desirable to separate the steps of tissue attachment and bypass tube placement.

There is provided in accordance with another aspect of the present invention, a method of attaching a device to the mucosal side of a wall of the gastrointestinal tract, the wall comprising a muscularis layer and a serosal layer. The method comprises the steps of providing a tension element, having a retention element thereon. The retention element is advanced through the wall from the mucosal side and the retention element is placed such that it is spaced apart from the muscularis by serosal tissue. Changes are caused to the serosal tissue in between the retention element and the muscularis. The device is attached to the tension element, such that the device is positioned adjacent the mucosal surface. As used herein, mucosal surface is a term of directional orientation and refers to the tissue surface facing the interior of the body lumen such as the lower esophagus or stomach, which may be covered by an endothelial layer.

The changes may be caused to the serosal tissue following the attaching step. The changes may be caused to the serosal tissue prior to the attaching step. The changes may be caused to the serosal tissue in response to tension on the tension element, biasing the retention element against the serosal surface. Alternatively, the changes may be caused to the serosal tissue in response to the application of an active agent. The active agent may comprise a growth factor, a sclerosing agent, or other agent or process for increasing the tissue density (e.g. initiating a fibrotic response) of the serosal tissue residing between the retention element and the muscularis.

In accordance with a further aspect of the present invention, there is provided a method of treating a patient. The method comprises the steps of providing a gastrointestinal attachment cuff having a tubular body, a proximal end and a distal end. The gastrointestinal cuff is positioned in the patient's digestive tract adjacent a mucosal surface in the vicinity of the gastroesophageal junction, the mucosal surface separated from a serosal surface by a wall thickness. The gastroesophageal cuff is secured adjacent the mucosal surface by advancing at least three tissue anchors through the mucosal surface, across the wall thickness and through the serosal surface to position a transverse retention surface of each tissue anchor in contact with the serosal surface. Preferably, the foregoing steps are accomplished endoscopically.

The securing step may comprise advancing at least 6 tissue anchors through the mucosal surface, and, in certain applications, at least 12 tissue anchors.

The tissue anchor comprises a tension element such as a suture for connecting the transverse retention surface to the cuff. The transverse retention surface may be a surface on a T-tag, a disk, or other retention structure. The length of the tension element may be at least about 75% of the wall thickness between the mucosal surface and the serosal surface. Preferably, the length of the tension element is at least about 95% of the wall thickness, and, optimally, the length of the tension element is greater than the wall thickness. In one embodiment the length of the tension element is at least about 120% of the wall thickness.

The method may additionally comprise the step of providing an elongate flexible gastric bypass tube having a proximal end and a distal end, and attaching the proximal end to the cuff. The proximal end of the bypass tube may be attached to the cuff endoscopically. The attaching the proximal end of the bypass tube to the cuff step may comprise removably attaching the proximal end of the bypass tube to the cuff. The distal end of the bypass tube may be positioned in the patient's jejunum, or in the patient's ileum.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIGS. 13 and 14 show a T-tag embodiment with a living hinge.

FIG. 20 shows a high-strength polymer T-tag embodiment.

FIGS. 21A-21D show an X-tag anchor embodiment and deployment of such an embodiment.

FIGS. 22A-22B, 23A-23B, 24A-24B, 25A-25B, 26A-26B illustrate alternate T-tag embodiments.

FIGS. 27A-27B show a T-tag fastener with a spacer to avoid excessive pressure on the tissue.

FIGS. 28A-28D show deployment of another T-tag fastener with a spacer to avoid excessive pressure on the tissue.

FIGS. 32A-32C illustrate methods and apparatus for delivering inflatable silicone and mechanical anchors.

FIG. 34 illustrates a radially expandable anchor embodiment.

FIGS. 37A-37G illustrate a dual-headed T-tag fastener.

FIGS. 52A-52B show a method of rotationally orienting a-T member of a fastener after insertion.

FIG. 53 shows another method of rotationally orienting a T member of a fastener after insertion.

FIGS. 54A-54C show embodiments of a grasping device combined with an attachment device.

FIGS. 57A and 58A-58C show an example of vertically mounted isolated sliding attachment members in a patient's stomach. FIG. 57B shows an example of a vertically mounted isolated hook and loop attachment structure in a patient's stomach.

FIGS. 61A-61B, 62A-62B and 63A-63B show embodiments of a flexible attachment device with a removable bypass tube.

FIGS. 68-69 show examples of tissue prestrengthening in the gastrointestinal system.

FIGS. 70-71 show examples of tissue thickening in the gastrointestinal system.

FIGS. 72A-72C show the effect of tissue thickening on a fixed length suture or fastener.

FIGS. 73A-73C show controlled suture lengthening to compensate for tissue thickening.

DETAILED DESCRIPTION OF THE PREFERRED EMBODIMENT

Figure 1A:
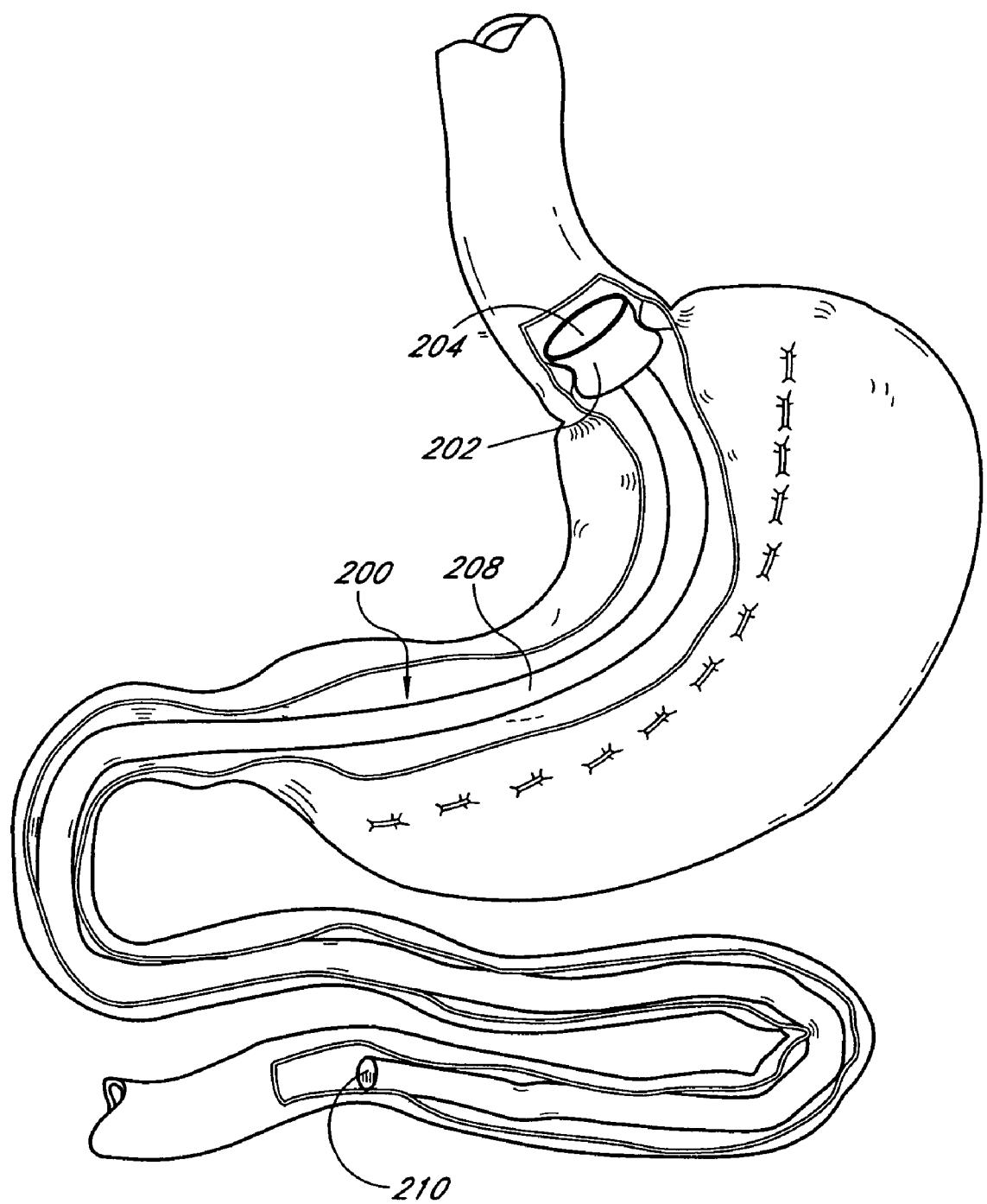
FIG. 1A shows a gastrointestinal sleeve device attached to an artificial stoma device implanted within a patient's stomach.
Figure 1B:
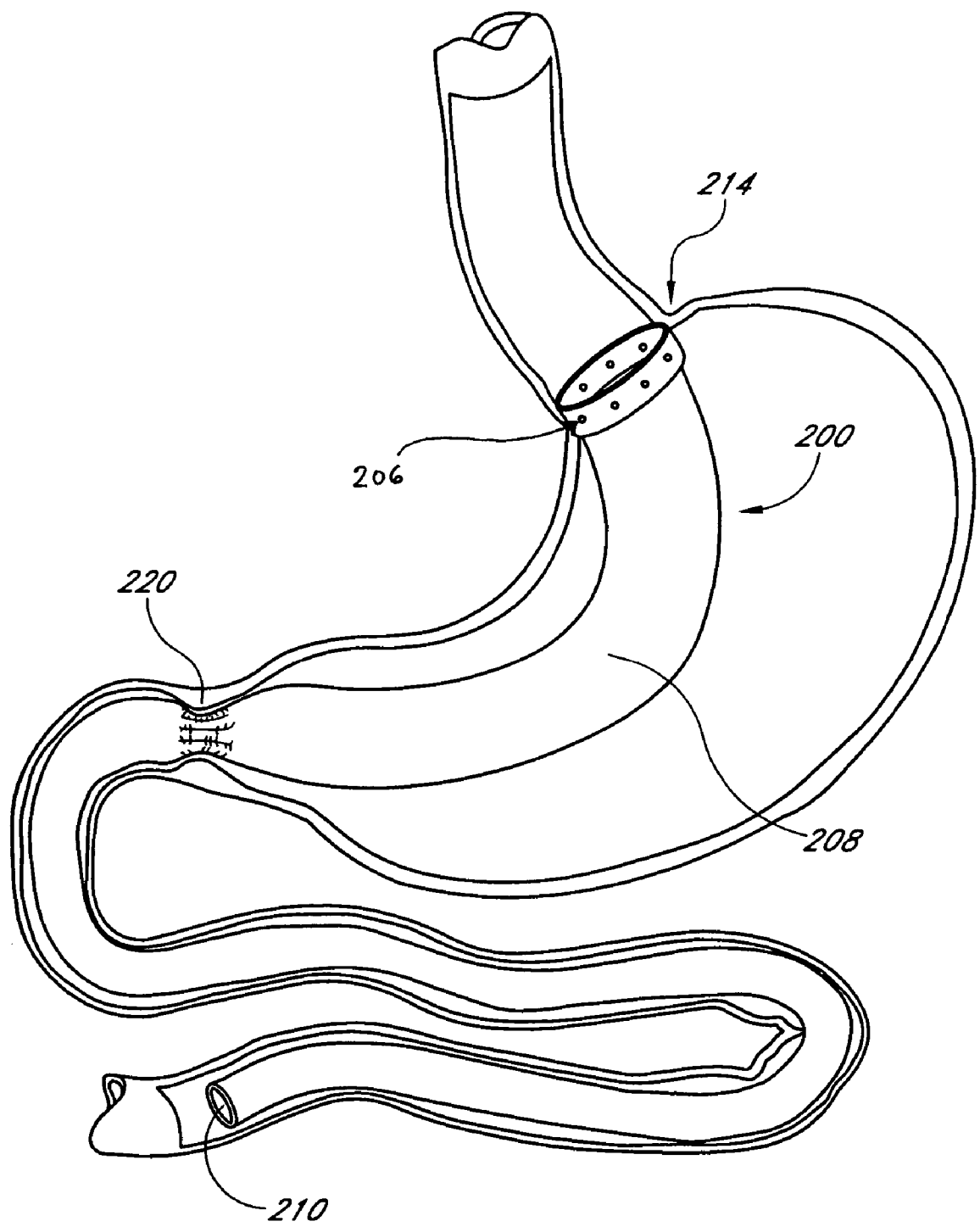
FIG. 1B shows a gastrointestinal sleeve device attached at the GEJ with an attachment cuff.

U.S. patent application Ser. No. 10/698,148, previously incorporated by reference, describes gastrointestinal sleeve devices that can mimic a Roux-en-Y gastric bypass by effectively reducing stomach volume, bypassing a portion of the stomach and/or small intestines, reducing nutrient absorption in the stomach and/or small intestines and depositing minimally or undigested food farther than normal into the intestines, thereby stimulating intestinal responses. The gastrointestinal sleeve devices described therein are all adaptable for use with the apparatus and methods of the present invention. FIGS. 1A-1B show representative examples of such gastrointestinal sleeve devices.

FIG. 1A shows a gastrointestinal sleeve device 200 attached to an artificial stoma device 202 implanted within a patient's stomach. The artificial stoma device 202 can be implanted in the vicinity of the gastroesophageal junction, or at the outlet of a surgically created gastric pouch to create a restriction that limits the volume of food that can be ingested at one time. The artificial stoma device 202 can have a fixed diameter stoma opening 204 or it can have an adjustable stoma opening or it can be a "smart" stoma that adjusts the size of the stoma opening in response to various conditions. The artificial stoma device 202 is preferably configured for peroral delivery and attachment using endoscopic techniques. Alternatively, the artificial stoma device 202 can be implanted using laparoscopic or open surgical techniques. The gastrointestinal sleeve device 200 is an elongated flexible tubular structure that is attached to the artificial stoma device 202 such that food and liquids pass through the stoma opening 204 and enter the internal lumen 208 of the sleeve device 200. The artificial stoma device 202 and the gastrointestinal sleeve device 200 can be implanted simultaneously, or the artificial stoma device 202 can be implanted by itself and then the gastrointestinal sleeve device 200 can be attached to the artificial stoma device 202 in the same or a subsequent procedure. The stomach may tend to shrink around the sleeve device over time due to disuse, reducing the stomach volume and increasing peristaltic coupling between the stomach wall and the sleeve device. Optionally, a line of staples or other fasteners 206 may be used with any of the devices to create a gastroplasty to reduce the volume of the stomach.

In conjunction with the stoma and/or gastric sleeve, the volume of the stomach can be reduced by suturing, stapling using open, transesophageal or laparoscopic techniques. Alternatively or in addition, a gastric balloon or other volume displacement device may be used in conjunction with the gastric sleeve to provide a feeling of satiety. These adjunctive techniques may have the effect of further reducing nutrient intake (in the case of a stomach reduction and pouch formation upstream of a stoma) and enhancing the effect of peristaltic motions of the stomach for moving food through the gastric sleeve intake (in the case of a stomach reduction downstream of a stoma where there is a gastric sleeve).

FIG. 1B shows a gastrointestinal sleeve device 200 attached at the GEJ with an attachment cuff 214. Tissue anchors, described below, have been omitted for simplicity. The cuff 214 may include a plurality of preformed apertures 215 for attachment of tissue anchors as is discussed below. The attachment cuff 214 and the gastrointestinal sleeve device 200 can be implanted simultaneously, or the attachment cuff 214 can be implanted by itself and then the gastrointestinal sleeve device 200 can be attached to the attachment cuff 214 in the same or a subsequent procedure. The attachment cuff 214 and/or gastrointestinal sleeve device 200 may, in one embodiment and as shown in FIG. 1B, be provided with preformed holes 206 for attachment of tension elements as described herein. Optionally, the attachment cuff 214 can be allowed to heal for a period of time before attaching the gastrointestinal sleeve device 200. Additionally, the gastrointestinal sleeve device 200 can be later removed or replaced without removing the attachment cuff 214. In this example, the volume of food ingested is limited by the portion of the sleeve device 200 upstream of the pylorus 220 rather than by a restrictive stoma. Furthermore, attachment at the gastroesophageal junction excludes all gastric secretions from the interior of the gastrointestinal sleeve device 200.

In each of these examples, the gastrointestinal sleeve device 200 preferably has a length such that ingested food and liquids bypass most of the stomach and at least a portion of the small intestine. Undigested food and liquids exit the distal end 210 of the sleeve device 200 into the small intestine reducing caloric absorption and eliciting physiological responses within the intestines. The gastrointestinal sleeve device 200 can have a constant diameter throughout its length or the diameter may vary along the length. The gastrointestinal sleeve device 200 can be impermeable along the entire length or some or all of the device may be porous or semipermeable. Preferably, the wall of the gastrointestinal sleeve device 200 is thin and flexible so that peristalsis is coupled to the internal lumen 208 of the device. A gastric sleeve that extends beyond the pylorus 220, with or without an intestinal sleeve, can allow use of the pylorus as a natural stoma by configuring the sleeve to close by the pylorus and then open to allow passage of food when the muscles of the pylorus relax. The section of the sleeve device 200 that passes through the pylorus 220 will preferably have enough wall flexibility or compliance to allow normal opening and closing of the pylorus to release and retain stomach contents and to allow drainage of stomach secretions around the outside of the sleeve. This can optionally be accomplished by the inclusion of pleats, channels or other structures to facilitate the collapse and sealing of the sleeve as well as passage of gastric secretions along the outside of the sleeve as shown in FIG. 1B.

Structures, features and methods illustrated in FIGS. 1A-1B can be combined or interchanged based upon clinical requirements. Similarly, dimensions, materials and other specifications described in U.S. patent application Ser. No. 10/698,148 can be adjusted based upon the clinical situation. For example, the gastrointestinal sleeve 200 is preferably approximately 60-180 cm in length whereby partially digested or undigested nutrients exit from the sleeve into the jejunum where they can elicit a hormonal, neural and/or osmotic reaction in the jejunum and/or ileum. Increasing the length of the sleeve can reduce the absorption of nutrients in a manner similar to that of a Roux-en-Y or bypass device, as will be understood by those skilled in the art. The sleeve may extend sufficiently far into the intestine, such as past the ligament of Treitz, so that it is retained in the intestine and not pushed back into the stomach. Lengths of at least about 50 cm, at least about 75 cm, at least about 100 cm and at least about 120 cm are contemplated, although different lengths may be appropriate depending upon the requirements of a particular patient. Thus, lengths of no greater than about 5 cm or no greater than about 10 cm or no greater than about 20 cm may be desirable for certain patients.

The releasable attachment of the sleeve to the cuff as disclosed herein facilitates removal and replacement of the sleeve. Thus, the response of a particular patient to a first sleeve having a first length can be observed. If more or less intestinal absorption is desired, the first sleeve can be endoscopically removed such as by cutting the tension elements discussed below, and replaced by a second sleeve having a second shorter or longer length. Therapy is thus adjustable, which may be desirable if either the initial sleeve length was suboptimal or if it becomes suboptional due to post implantation changes such as stomach remodeling or behavioral changes.

Optionally, the sleeve can include coatings on its interior and/or exterior to enhance the surface properties of the sleeve in clinically relevant manners. Coating examples include: 1) parylene coatings to increase the chemical resistance of a sleeve material, 2) coating with an antimicrobial agent to resist infection and/or 3) coating with an anti-inflammatory agent to reduce tissue inflammatory response, as described herein. Similarly, the interior and exterior of the sleeve can optionally be coated with a low friction material (e.g. a hydrogel) to reduce friction of food passage (interior) and reduce gastric irritation (exterior). One example of such a low friction material is a lubricious coating such as the PHOTOLINK LUBRICIOUS COATING manufactured by Surmodics Inc. and disclosed on pg. 5, paragraph 58, in U.S. utility patent publication 2005-0049718, the disclosure of which is herein incorporated in its entirety by reference.

U.S. patent application Ser. No. 10/698,148 describes the use of biodegradable or bioresorbable materials for construction of a gastrointestinal sleeve device to obviate the need for removal of the sleeve device at the end of the treatment period. The entire gastrointestinal sleeve device or a portion of it may be made of biodegradable material. The gastrointestinal sleeve device may be made of biodegradable materials with different rates of degradation or resorption. The gastrointestinal sleeve device may be configured with a series of segments that biodegrade sequentially. For example, a first portion on the distal end of the sleeve may degrade first, followed some time later by a second intermediate portion and a third proximal portion. Next the attachment would degrade and, finally, the T-tags or other fasteners would degrade. Alternatively, the gastrointestinal sleeve device may be configured with a series of short segments of non-biodegradable material that are attached to one another with biodegradable material. The biodegradable attachment portions may be made of biodegradable materials with different rates of degradation or resorption so that they biodegrade sequentially. In either case, the biodegradable material would allow a gradual change of therapy over time, without having to revise or replace the implant. The patient could get used to the gradual change in therapy more readily than a sudden change and may be better able to avoid a rebound in weight gain. It may also allow for a safe mode of degradation and elimination. The device would degrade into pieces small enough that they could be eliminated without any danger of bowel obstruction.

Alternatively, selected portions of the gastrointestinal sleeve device may be made of biodegradable material. For example, openings in the sleeve can be covered with biodegradable material that will gradually degrade over time, eventually allowing food to mix with digestive secretions. The biodegradable material would allow a gradual change of therapy over time, without having to revise or replace the implant. The gastrointestinal sleeve device with the openings in it could be left in place for long-term maintenance of weight loss or it could eventually be removed.

In some embodiments the rate of degradation of the biodegradable material forming the sleeve could be coordinated with the natural pH of the anatomical environment and/or to properties of the material forming the sleeve, to achieve a predetermined sequential degradation of the implant. In accordance with one degradation sequence, a distal (intestinal) portion of the sleeve dissolves before the proximal (gastric) portion. For example, the sleeve could be constructed of a material that degrades at a faster rate in a relatively basic environment than in a relatively acidic environment such that the distal portion of the sleeve in the intestine would dissolve before the proximal portion of the sleeve in the stomach. The pH of the sleeve environment could also be altered by an external source, for example by ingestion of a substance that would change the pH of the stomach and/or intestine and thus hasten degradation of the gastric component. Alternatively, the distal and proximal portions of the sleeve could be constructed of two different materials with the material comprising the distal portion dissolving faster than the material comprising the proximal portion. Alternatively, the material forming the sleeve could be thinner at the distal portion than at the proximal portion such that the distal portion would dissolve in less time than the proximal portion. All or any combination of the above alternatives could be used to set the time frames of degradation of the distal and/or proximal portions of the sleeve depending on the desired performance.

Biodegradable material suitable for construction of a gastrointestinal sleeve device is sold under the name Plastifilm by OsteoBiologics, Inc., located in San Antonio, Tex. This biodegradable polymeric film material is described in U.S. Pat. No. 6,514,286, which is hereby incorporated by reference. Additional information from the supplier about this material is available at: http://www.obi.com/.

Another aspect of the present invention involves devices and methods for delivery and deployment of a gastrointestinal sleeve device into a patient's gastrointestinal tract. One method to facilitate delivery of the device into and through the patient's small intestine is to place a guidewire and/or catheter into the intestine to the depth desired and then push the gastrointestinal sleeve device over the guidewire. Successful techniques for placing a guidewire into the small intestines have been described by G. Long, T. Mills and C. P. Swain in an article entitled *Techniques for advancing guide wires and devices in the lumen of the gastrointestinal tract*. Another technique that could be adapted for placing a device such as a gastrointestinal sleeve device into the small intestine was described by H. Yamamoto and K. Sugano in an article entitled *A new method of enteroscopy—the double-balloon method*, Can J Gastroenterol. April 2003; 17(4):273-4. These techniques can be used in combination with many of the delivery and deployment methods described herein and in the prior application.

Methods of insertion and retrieval of a gastrointestinal sleeve device are also described in the parent application. In addition to the methods described therein, a GI sleeve can be inserted and/or retrieved using a flexible endoscope. A skilled GI endoscopist can "drive" a special endoscope (an enteroscope) through the duodenum and deep into the jejunum. Because of its small size, a pediatric colonoscope can be used to access an area further down the intestine. With proper interfacing structure on a GI sleeve, the sleeve can piggyback on the endoscope as it is driven into the jejunum and then released with its distal end left in the jejunum when the endoscope is retracted and removed from the body. This can be accomplished perorally either before or after attachment of the proximal end of the sleeve to tissue or to a cuff at the GEJ or some other clinically desirable location.

Various structures can be used as an interface between the endoscope and the distal end of the GI sleeve device. If the sleeve device has a solid distal end or other graspable portion, such as a tab or loop near the distal end, a standard or custom endoscopic snare or grasper can be extended through the endoscope working channel to grasp the sleeve device. Alternatively, the distal end of the sleeve device can be configured with a socket or pocket to engage a flexible pusher, which may be configured as a rod, tube or guidewire. As another alternative, the sleeve device can be configured with a distal end that can be cut off to release the device. The distal end of the sleeve device is grasped with a snare or the like extended through the endoscope working channel. Once the sleeve device is delivered far enough distally in the GI tract, the distal end of the sleeve device is cut off to release the device.

In one embodiment, delivery of the sleeve device to an area sufficiently far down the intestine is facilitated by attaching a traction structure, such as a mercury ball, that increases the likelihood that the sleeve will be pulled down the intestine, to the distal end of the sleeve. During peristalsis the intestinal wall grabs hold of the traction structure and pulls it along with the distal end of the sleeve down the intestine.

Location of Attachment of the Sleeve Device

Figure 2A:
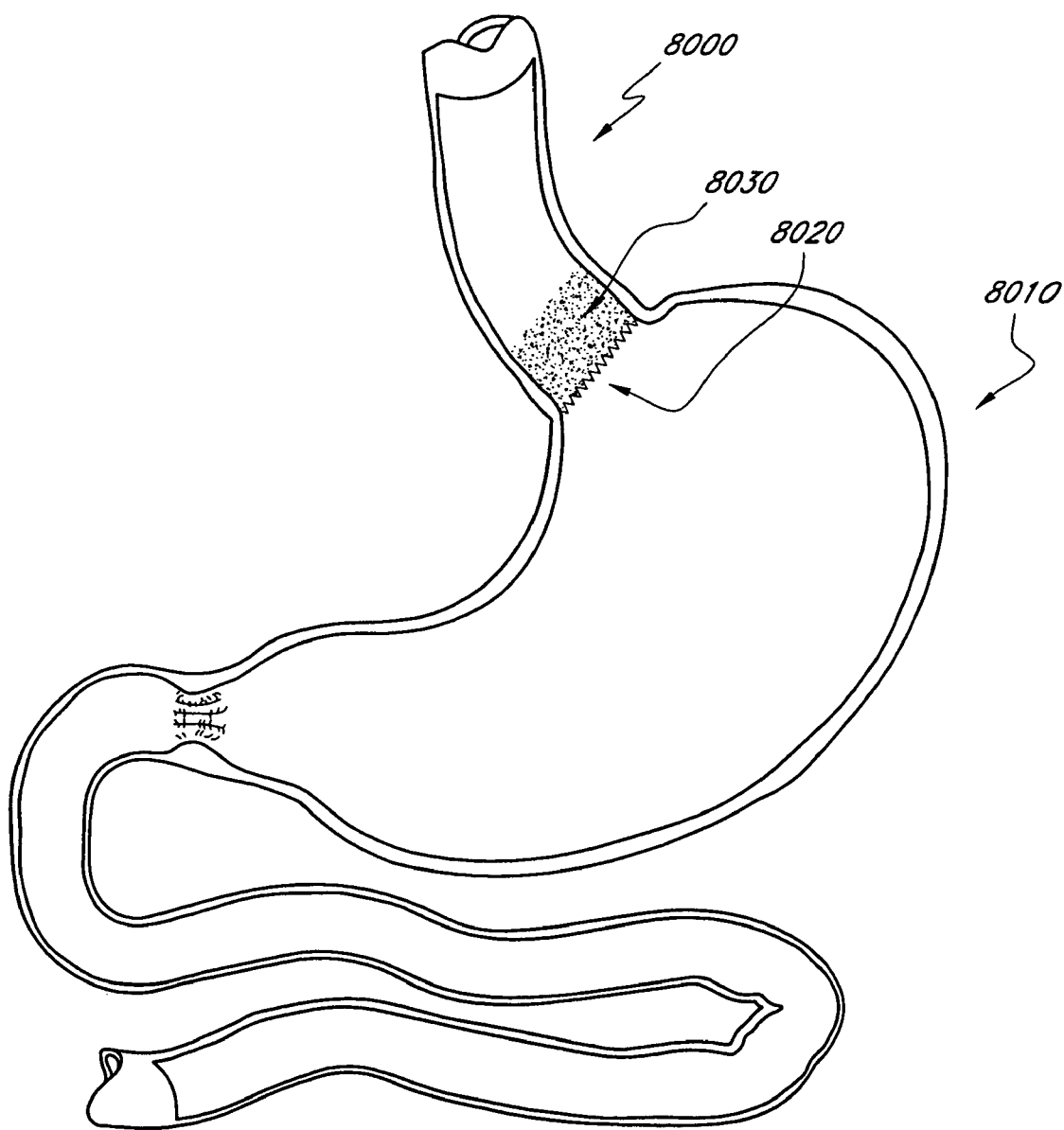
FIG. 2A shows a schematic illustration of the GEJ and the SCJ or Z-line and the target tissue zone identified by the present inventors.

The present inventors believe that some areas of the esophageal or gastric wall exhibit physical properties more conducive to retaining attachment structures than other areas. For example, an attachment zone 8030, shown in FIG. 2A, directly above the squamocolumnar junction (SCJ) 8020, also known as the Z-line, ora serrata, and mucosal GEJ, may be such an area. The SCJ marks the junction of the squamous mucosa of the esophagus and the columnar or glandular mucosa of the stomach. The SCJ may be located at or below the lower esophageal sphincter (LES).

The device may, in one preferred embodiment, be attached in an attachment zone 8030 no more than about 2 cm and preferably no more than about 1 cm above the SCJ 8020 and below the esophagus 8000 where the squamous mucosa is thicker than the squamous mucosa of the esophagus 8000 and where there exists a serosal outer surface not exhibited at the esophagus 8000. The thicker layer of squamous mucosa in the attachment zone 8030 terminates distally at the endoscopically visible transition to the glandular mucosa of the stomach 8010 which occurs at the SCJ 8020. The device is also preferably attached at a location in the attachment zone 8030 so as to minimize the risk of reflux. The SCJ 8020 can be located relative to other anatomical regions. It normally may be found at the gastroesophageal junction (GEJ). The GEJ is the region at which the tubular esophagus joins the saccular stomach. The GEJ can be considered the first part of the stomach 8010 or the cardia and is located at the proximal margin of the longitudinal gastric mucosal folds or in the distal 2 cm of the esophagus 8000 and proximal stomach 8010. Endoscopically, the location of the GEJ can be approximated by identifying the proximal margin of the gastric folds.

Thus, a first aspect to the location of attachment of the devices disclosed herein relates to the position of the attachment structures along the axis of the hollow lumen or organ. As described above, the attachment location in the axial direction is preferably in the vicinity of the gastroesophageal junction, and particularly just above the SCJ. This attachment site can be located endoscopically by observing the color change which occurs at the SCJ, and retracting or positioning the attachment structures of the endoscope slightly above that line.

A second aspect to the location of the attachment structure relates to the depth within the adjacent tissue wall (i.e., in a transverse direction to the longitudinal axis described above) within which the various anchors or retention structures disclosed herein reside. Applicants believe that the location in the transverse direction is subject to migration or other change post-implantation, as described in connection with FIGS. 2B through 2D.

Figure 2B:
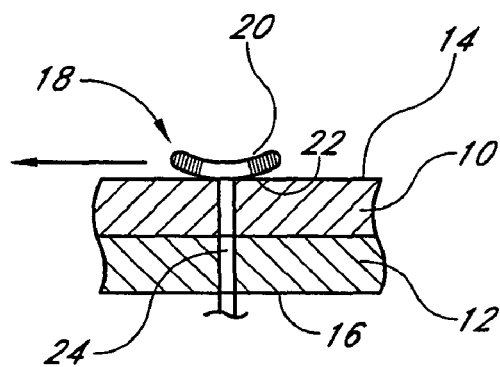
FIG. 2B shows a schematic illustration of a tissue anchor placed adjacent the serosa at the time of implantation.

Referring to FIG. 2B, there is disclosed a highly simplified schematic view of a tissue wall such as the wall of a hollow organ or lumen in the body, including the wall at the vicinity of the gastroesophageal junction. The tissue wall comprises a serosa 10 and a muscularis 12. Additional tissue layers have been omitted for simplicity. In general, as is appreciated by those of skill in the art, the serosa 10 is on the outside of or faces away from the stomach, and the muscularis is on the inside, or faces towards the interior of the stomach. The serosa 10 thus includes a serosal surface 14 which faces away from the interior of the stomach, and the muscularis 12 includes a muscularis surface 16 which faces towards the interior of the stomach.

Figure 2C:
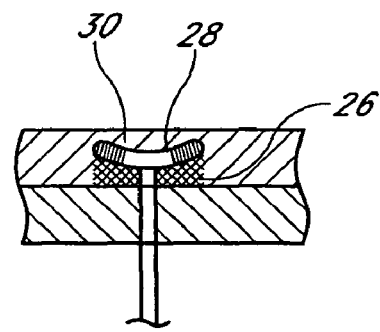
FIG. 2C shows a schematic illustration as in FIG. 2B, at a post implantation stage when the anchor has relocated into the serosa, and a layer of increased tissue density has formed on a proximal side of the tissue anchor.
Figure 2D:
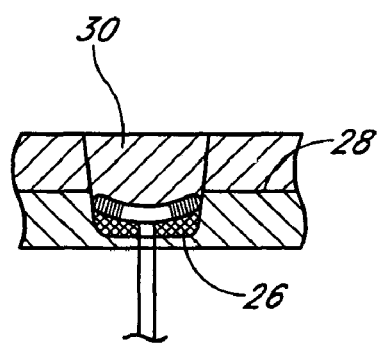
FIG. 2D is a schematic illustration as in FIG. 2C, with the anchor relocated proximally into the plane of the muscularis.

An attachment device or anchor 18 is illustrated in part in FIGS. 2B through 2D. The attachment device 18 can take any of a variety of forms, described elsewhere herein. In general, the attachment device 18 includes a retention element 20 having at least one retention surface 22 thereon. The retention element 20 may be integrally formed with or attached to a tension element 24, which extends through the tissue wall and is secured to the device implanted within the gastrointestinal tract. Although the attachment mechanisms disclosed herein will be defined primarily in the context of an obesity device, which is attached in the vicinity of the GEJ, those of skill in the art will appreciate that the attachment system disclosed herein may be utilized in any of a wide variety of other anatomical locations, such as in the bronchial tubes, urethra, ureters, fallopian tubes, throughout the GI tract, and others which share a serosa or serosa like layer, such as in the kidney, bladder, and other organs, as would be recognized by those skilled in the art.

Referring to FIG. 2B, the retention element 20 is illustrated with the retention surface 22 residing against the serosal surface 14. Retention surface 22 may comprise any of a variety of forms, such as a proximal surface on a T-tag, proximal surface on a disc, or any other surface which extends in a generally lateral direction with respect to a longitudinal axis of the tension element 24. The transverse retention surface 22 may be radially enlargeable or expandable from a first, reduced cross-sectional configuration to provide a low crossing profile such as for deployment through a deployment cannula, and a second, radially expanded or enlarged cross-sectional profile as illustrated in FIG. 2B, to provide a retention surface 22 which will engage or interfere with tissue of the serosa 10 or muscularis 12 to resist proximal retraction of the attachment device 18 through the tissue. Transformation between the first configuration and second configuration can be accomplished in any of a variety of ways as is discussed further herein, such as by pivoting the retention element 20 about the attachment point to tension element 24, by radial expansion, by inflation, or other technique.

Tension element 24 may comprise any of a variety of connectors or elements adapted to extend through the tissue wall, such as a suture, or other single stand or multi-strand filament or material. In some embodiments the tension element 24 is formed of a polymer such as PEEK or silicone. The tension element 24 may also, in some embodiments, have elastic properties. In other embodiments the tension element 24 does not have elastic properties. By use of the term tension element, no specific mechanism is suggested, and the element is not required to be under mechanical tension.

The attachment device, otherwise sometimes referred to herein as a tissue anchor, T-tag or other label, it is illustrated in FIG. 2B in a schematic fashion as it may appear at the time of implantation. Since in certain implementations of the invention the length of the tension element 24 will exceed the uncompressed thickness of the adjacent tissue wall, the retention surface 22 may even be spaced slightly apart from the serosal surface 14 depending upon the transient motion or configuration of the stomach at any given time.

Without being limited to any particular structure or mechanism, Applicants believe that the presence of the attachment device may cause or accelerate the formation of a layer 26 of serosal tissue having increased tissue density relative to unaffected or normal serosal tissue. The layer of increased density 26 may result from a process in which the transverse retention surface 22 places pressure against the serosa 10, causing a localized necrosis due to the restriction of capillary blood flow. The necrosed tissue thereafter fibroses, as a part of a normal healing response. The layer of increased density 26 or fibrosis may also result from a foreign body reaction triggered by the presence of the transverse retention surface 22. Appli- cants have observed a greater degree of fibrosis or denser tissue on the side of the T-tag facing the lumen of the stomach, for example on the retention surface 22.

In certain animal trials conducted by Applicants in which the animals were sacrificed five weeks following implantation of the attachment device 18, successful anchors appeared similar to the simplified schematic illustration of FIG. 2C. In this illustration, the location of the retention element 20 has changed relative to the serosa 10 and muscularis 12, and the distal surface 28 of the retention element 20 has been covered with an overgrowth of serosal tissue 30. A fibrotic layer 26 is positioned in between the retention surface 22 and the muscularis 12. Although illustrated only on the proximal side of the retention element 20 where the greatest degree of fibrosis has been found to occur, the fibrotic response appears to some extent to surround and wall off the entire retention element 20.

It appears to the present inventors that formation of a sufficient fibrotic response on the proximal side of the retention surface 22 decreases the likelihood that the attachment device 18 will relocate to the inside of the stomach under normal agitation of the stomach, changes in the thickness of the stomach wall, and other conditions normally occurring in the stomach. A similar response is schematically illustrated in FIG. 2D, in which the layer 26 of high density serosal tissue remains on the proximal side of the retention element 20, however one or both of the layer 26 and retention element 20 have relocated to below the normal plane 28 separating the serosa 10 from the muscularis 12 and will remain there.

It appears to the present inventors that if the device design and/or retention element 20 design are such that in normal use the retention element 20 relocates to a position in the muscularis 12 and past the serosa 10 before a sufficient fibrotic response, the retention element 20 may relatively easily pass through the muscularis 12 and failure will result. Thus, it may be desirable in certain implementation of the invention to facilitate or accelerate the formation of the fibrotic layer 26. This may be accomplished in any of a variety of ways which will be appreciated by those of skill in the art in view of the present disclosure, such as by the introduction of an active agent which will trigger a fibrotic response. Suitable active agents may include any of a variety of growth factors, and/or chemical sclerosing agents which are well known for other medical applications. Active agents may be applied as a coating to the retention surface 22 or retention element 20, or may be impregnated into the material of retention element 20, such as to permit a timed release into adjacent tissue. Incorporation may be accomplished by loading the active agent into tortuous pathways or pores exposed to the surface of the retention element 20, or by inclusion in a bioabsorbable or bioerodable carrier attached to or positioned in the vicinity of the retention'surface 22. Energy sources may also be utilized, such as to generate heat or otherwise stimulate formation of a fibrotic response, as is discussed further below. Formation of the fibrotic layer 26 may also be facilitated by mechanical means, for example, in one embodiment, by roughening the retention surface 22 with the addition of fibrotic layer enhancement structures such as a plurality of bumps or etched lines.

Figures 2E, 2F:
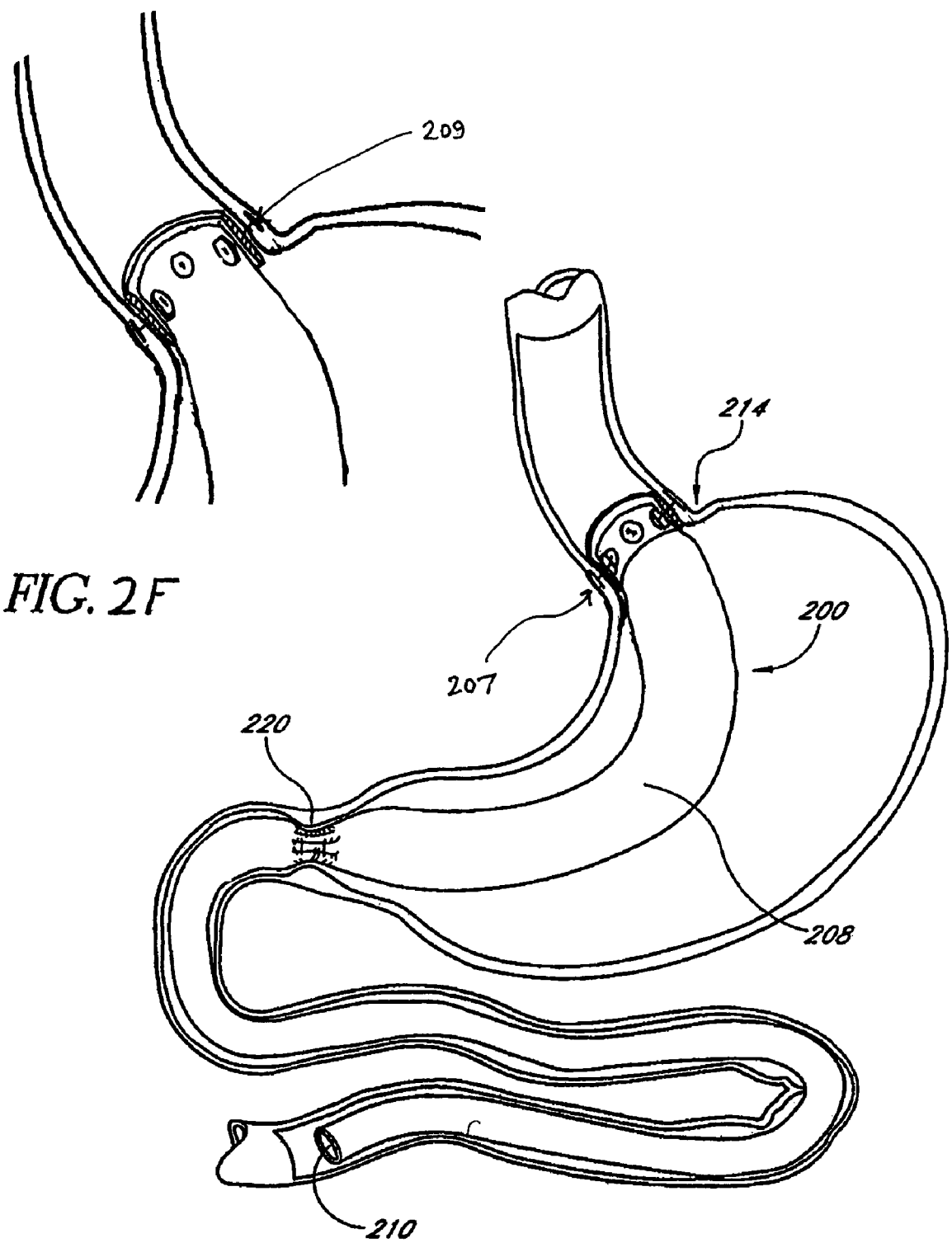
FIGS. 2E-2F show an attachment cuff attaching a gastrointestinal sleeve device using T-tags secured with a button.

FIG. 2E shows an implanted gastrointestinal sleeve device 200 attached by an attachment cuff 214 with the use of T-tags 207. FIG. 2F is an enlarged view of the attachment cuff 214 attached with T-tags 207 showing the tension elements 209 of the T-tags 207 embedded in the stomach wall.

T-Tag Attachment Embodiments

T-tag fasteners can be used to attach many of the structures described herein. A T-tag is basically a retention element 20 in the form of a cross member or "T" that is attached to a tension element 24 in the form of an elongated member or tail at or near the mid-point of the T. A "stem" may be a structure at the joining point of the T and tail. From the perspective of a peroral attachment technique, in which the attachment devices are preferably advanced through muscularis 12 in the direction of the serosa 10, the stem or tension element will be referred to herein as relatively proximal to the cross member on the T-tag. The T-tag is a member of a more general family of tissue anchors, in which a proximally facing surface 22 (such as the proximal surface of the cross member) is adapted to be bent, folded, or otherwise reduced in crossing profile to a first configuration in which it can be advanced distally through a relatively small tissue opening, to a second configuration in which it presents a proximal serosal surface contacting area for resisting proximal retraction through the access pathway. Thus, although described primarily in the context of a T-tag and variations thereof, the present invention relates more broadly to tissue anchors of the type for presenting a retention surface which may have any of a wide variety of configurations. Some are described in additional detail below. The stem may also be referred to herein as a tension member, and may comprise a suture, or other single strand or multi-strand element for drawing the tissue anchor against the serosal tissue and/or connecting the tissue anchor to the implantable cuff or other endolumenal implant.

T-tag fasteners are generally configured to flex or pivot at the juncture of the T and tail to allow delivery along the axis of the T through a minimal puncture diameter. T-tag fasteners can be configured with an extended tail that may extend out the mouth and optionally be used to parachute devices for attachment into position in vivo. Other T-tag configurations can include, crimp, snap, screw or other means of securing the T-tag tail when appropriate. One embodiment of a T-tag fastener could include a dual tail. Such a dual tail could be combined with extended tails that could then be tied out side the body with the ensuing knots then tightened within the body. Such a dual tail could be constructed of one of a number of non-biodegradable suture materials known in the art including polypropylene, nylon, braided Dacron or silk. In some clinical situations biodegradable tails could be indicated and could be constructed using materials described herein. In a preferred embodiment the tails could be constructed of a monofilament material.

In certain implementations of the present invention, it may be desirable to increase the effective surface area of the retention surface 22. This may be accomplished using any of a variety of disc or button shaped attachment devices 18 disclosed herein, or by introducing a buttressing component or element in the nature of a washer or other structure for enlarging the effective surface area. This buttressing structure may sometimes be referred to herein as a pledget. The buttressing material is generally configured perpendicular to the axis of the attachment means (e.g. suture, rivet or staple) and therefore best distributes forces along the axis of the attachment means. When a device is attached to the intragastric wall such forces can be directed inward from the gastric wall. Therefore, if the buttress is attached to the intragastric wall, the buttress may not be along the axis best suited to resist the applied force.

An alternate method of delivering these buttresses such as Fastener (T-tag) buttress (T-pledget) would be using a T-fastener (T-tag) where the "T" portion was constructed of a material with properties that would be useful as a buttressing material. This would be a T-tag buttress or a T-tag pledget. Some embodiments of T-tag pledgets, 920, are shown in FIGS. 3A-3D. These T-tags could be delivered through a hollow needle type delivery system (e.g. T-ANCHOR INTRODUCER GUN (Moss, Moss Tubes)) that has been redesigned/modified so it can be passed through the working channel of an endoscope. One advantage of the use of T-pledgets is that a T-tag can be designed with an elongated tail that can extent out through the mouth and be used to parachute structures into place in-vivo. T-pledget tails could include preloaded needles. Needles could be curved or straight.

In a preferred embodiment the cuff would be attached as the T-tags are placed such that the sutures of the T-tags could be knotted outside of the body and the knots could be pushed down the working channel or outside of the working channel of the scope until positioned to retain the cuff. The suture tails could subsequently be removed. To facilitate management of all the suture tails, two T-tags could first be placed to secure the cuff followed by placement of the rest of the T-tags. In a preferred embodiment the T-tag tension elements, such as tails, sutures, or other structures as described herein, would terminate in the stomach, such as by tied knots, sliding buttons, or preexisting terminated ends, such that they would not need to be brought outside of the body.

In one embodiment deployment of the sleeve device and/or T-tags is achieved with the use of a remote controlled robotic endoscope. Generally, a remote controlled robotic endoscope comprises a user interface, a control device, and an operating unit. Commands can be inputted by an operator into the user interface to activate the control device which in turn guides the operating unit in three dimensions. The operating unit, in one embodiment, can be a fastener deployment head carried by a catheter which is positionable within the gastrointestinal tract and capable of attaching various fastener structures such as sutures and T-tags in response to commands received by the user interface. Monitors that display physical data and images of the anatomy to aid in navigation of the operating unit may also be used with a remote controlled robotic endoscope. Such an endoscope could scale the operator's movements such that large movements of the operator would translate into the smaller movements that may be required to maneuver the endoscope within the gastrointestinal tract. One embodiment of a remote controlled robotic endoscope is described in "Radiocontrolled Movement of a Robot Endoscope in the Human Gastrointestinal Tract," by P. Swain, T. Mills, B. Kelleher, L. Schmitz, S. Mosse, P. Burke, K. Ikeda, and A. Fritscher-Ravens.

T-pledgets can be structured using a variety of means. A portion of standard Teflon pledget material can have a suture tied or otherwise attached, at or near its mid point. This can be structured or otherwise prepared for delivery by means such as rolling and/or compressing to facilitate passage through tissue with a minimum disruption of the tissue layer. Ideally the T-pledget would have a minimum diameter when passing through tissue. Depending upon the clinical situation varying deployed diameters/areas could be preferred. A hollow needle or other hollow tube can be used to facilitate passage through tissue. Structure and/or material selection to enhance axial rigidity along the axis of delivery will be beneficial in some clinical situations. A piercing point on the leading edge of the "T" may be useful with some delivery mechanisms.

Many of the features described herein can be achieved with construction using a single piece of Polypropylene, Nylon, PEEK, silicone, or other polymeric material well known in the art for use in construction sutures, which forms the "T" and tail as a single unit. Alternately two different materials can be combined, for example by insert molding, to achieve different properties of the "T" and tail. In another embodiment this could be combined with a "T" portion that is coated with a material selected for specific clinical properties such as encouraging or discouraging either in-growth or adhesion. The "T" portion may also be surrounded by another material such as Teflon pledget material or Dacron graft material. "T" diameter will vary according to the material used for example ranging from 0.5 mm to 3.0 mm in diameter for nylon or polypropylene with the typical "T" having a diameter of 1-2 mm. A tail could be the dimension of a standard suture and could generally vary from 5-0 to 0 (USP standard classification) though smaller or larger sizes may be appropriate in certain clinical situations.

In one configuration that could have advantages in certain clinical situations the "T" and/or tail portions of the T-pledget could be constructed in part or wholly of a biodegradable material as described herein. In one such configuration the "T" portion would be constructed of a flexible buttress material that is not biodegradable. In some embodiments this could have a tubular configuration. This would include a core of a more rigid material that is biodegradable. The tail in this situation could be optionally biodegradable. This combination T-pledget can have advantages in that its "T" portion will 1) have increased rigidity for insertion; 2) maintain its rigidity during the time period while the tissue goes through its healing period and ideally until it regains its strength; and 3) become softer and more flexible to minimize the potential for erosion over the length of time the pledget is in position. Various buttress materials, both biodegradable and not, are described herein.

In an alternative embodiment a porous buttress material could be impregnated with a biodegradable material to achieve a similar result. Similarly a biodegradable material could coat a buttress material. The rigidity of both the permanent buttress material and the biodegradable material may be selected and modified to suit specific clinical situations. In some situations the biodegradable material may be of a lesser rigidity compared to the buttress material. Embodiments that include a biodegradable tail portion could have an advantage in certain clinical situations, as this would eliminate the tail as a focus for a leak after it has degraded. Bioresorbable materials such as polyglecaprone (Monocryl, Ethicon), polyglactin (Vicryl, Ethicon) or other as well know in the art can be appropriate for use in these applications.

Bio-stable, solvent dissolvable pledget material—In other situations the pledget material could be made from a material that is stable in the body but could dissolve in the presence of a biocompatible solvent, or a biocompatible solution including a chemical or catalyst that will initiate the pledget's dissolution. This would allow simplified removal of the pledget material via lavage of the peritoneum if the stomach attachment means were to be released through an endoscopic procedure or were otherwise desirable based upon the clinical circumstances.

Referring to FIGS. 3A-3D, Retention elements 920 are designed for expandability. A T-tag or T-fastener can be used to provide knot free means to retain a suture against pull through of an associated anatomic structure. A further advantage of a T-tag is that the forces applied to the suture tail of the "T" are distributed over a larger area than a single stitch. This is accomplished by using a "T" dimensioned with a width wider than the diameter of the suture and a length longer than a typical bite or stitch. A disadvantage of a T-tag is that insertion of a T-tag through tissue potentially requires a hole many times, for example 5-15 times, the diameter of the suture tail.

Figure 3A:
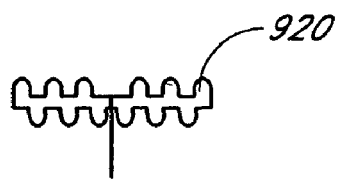
FIGS. 3A-3D illustrate examples of expanding T-tag fasteners.
Figure 3B:
Figure 3C:
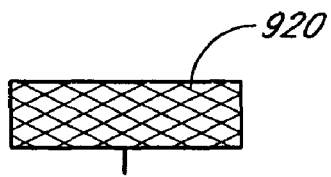
Figure 3D:
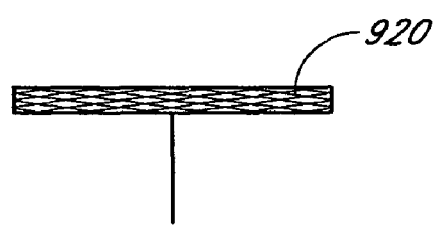

To deliver an improved buttressing capability in a T-tag fastener or T-pledget with a minimum delivery hole it is beneficial to use a "T" or pledget designed to expand after delivery. This can be beneficial in many clinical situations. In addition to rolling or compressing, alternate structures can include materials that expand when exposed to water such as hydrogels. FIGS. 3C and 3D show how a T-pledget 920 or T-tag 918 of woven cylindrical meshes that may be compressed or elongated to achieve a reduced diameter and expanded or shortened to become wider. Compared to a rectangular sheet, alternate configurations of a rolled and unrolled sheet can achieve a T-pledget 920 or T-tag 918 with increased projected width relative to its rolled diameter through the use of matching cutouts, as shown in FIGS. 3A and 3B. Though not as efficient in diameter-to-projected width ratio, is some cases it may be clinically desirable to have a "T" that is in a circular shape.

To resist bending perpendicular to the axis of the suture, it may be beneficial to use metals, for example Ti, SS or NiTi. In some clinical situations, encapsulating or coating the metal with a fluoropolymer or other coatings as described herein may also be beneficial.

T-tag with inflammatory reaction or other additives—The pledget material could be optionally coated or impregnated with materials and/or medicaments as described herein. For example the pledget can be coated with a material that would enhance inflammation and scar formation. Alternatively, a coating or medicament that would either encourage or discourage in-growth can be applied.

In some clinical situations it may be beneficial to use both these types of coatings. For example, though inflammation can lead to scarring fibrosis and ultimately strengthen tissue, the inflammatory process initially results in tissue weakening that can include tissue liquefaction. Therefore, it can be desirable that a fastener that induces an inflammatory response for long term strength also include means to support the tissue during the weakened stage.

Inflammatory reaction materials would be limited to a portion of the T-tag or T-pledget as the inflammatory response weakens tissue before the scarring fibrosis occurs. Therefore, for example, having the area at the center of the T or pledget with this inflammatory material and the ends of the "T" without this material could have an optimized balance of short term and long term strength.

Drug-eluting coatings may be used to encourage or discourage tissue ingrowth into the fasteners or other device attachment mechanisms described herein. A low inflammatory response is generally desirable for encouraging tissue ingrowth. Anti-inflammatory drugs that may be used include steroidal anti-inflammatory drugs, e.g. prednisone, and non-steroidal anti-inflammatory drugs (NSAID), e.g. chromalin. Conversely, drugs that may be used to control or reduce tissue ingrowth include Taxol (paclitaxel) (Bristol-Myers Squibb) and Sirolimus (rapamycin) (Wyeth-Ayerst Laboratories).

Embodiments designed for improved erosion resistance—The purpose of the "T" or other retention element is to distribute and resist the forces that could act to pull it through tissue, in this case the gastric wall. To better achieve this result the "T" should resist excessive bending. Though a T-fastener is generally held parallel to the surface of the extragastric wall, at the ends of the "T" the gastric wall extends outward from the plane of the surface and the axis of the "T". In this case, the gastric wall could be at a 90-degree angle, or greater, to the ends of the "T". To reduce the potential for erosion at the end of the "T" in some clinical situations it could be beneficial for the ends of the "T" to have increased flexibility which will result in a reduction of the angle between the gastric wall and the ends of the "T". This would reduce the forces between the "T" and the gastric wall and therefore reduce the potential for erosion at the ends. Structures that could accomplish this could include tapered thickness or cross section to reduce the bending moment. Alternatively or in addition, changes in material properties such as hardness, bending modulus and/or elongation can accomplish the same result. For example the "T" near the stem could be of a material of a durometer such as Shore 65D or higher and the material may change as one moves out along the arms of the "T" transitioning through 55D/100 A to 90 A durometer or lower. Rounding, smoothing and structures that otherwise distribute forces over a larger area will also serve to reduce erosion at the ends of the "T". A circular shaped "T" may be particularly desirable to reduce erosion.

Figure 4A:
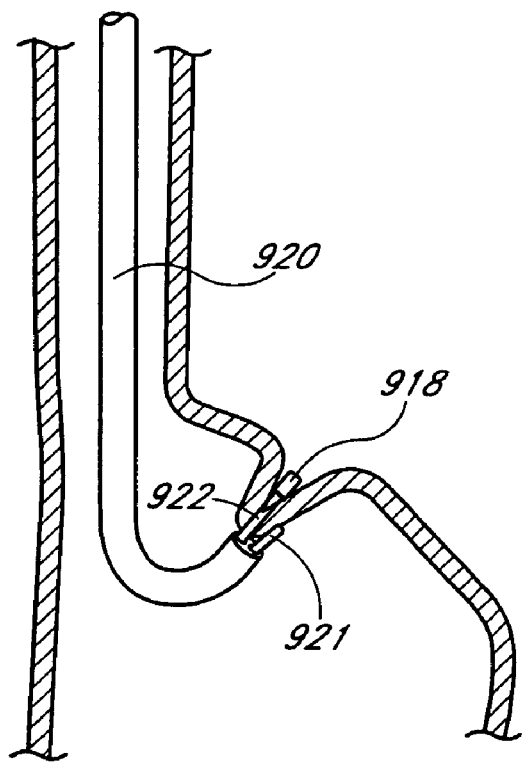
FIGS. 4A-4B illustrate placement of fasteners.
Figure 4B:
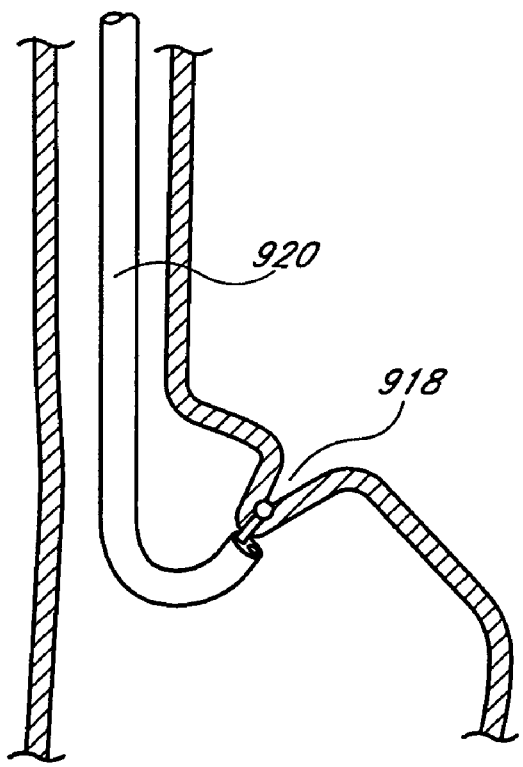

FIGS. 4A-4B illustrate a method of placing T-tag fasteners 918 through the gastric wall that prevents accidental damage to other structures. One method of accomplishing this end could involve the use of an endoscope 920 with two (2) working channels. One channel could be used to deliver a grasping means 921 that would grasp the gastric wall to stabilize the wall and optionally invaginate it to displace the area grasped away from adjoining structures (e.g. spleen and aorta). The second working channel can then be used to deliver a T-tag fastener 918 through, for example, a hollow needle type delivery system 922 (e.g. T-ANCHOR INTRODUCER GUN (Moss Tubes)) that has been redesigned so it can be passed through the working channel of an endoscope and then rotate 90 degrees into position (as illustrated in FIGS. 5B and 5C). Laparoscopic or other extragastric means could also be applied to the end of preventing damage to adjoining structures. The grasping means 921 may be omitted from the procedure if desired.

For each subsequent T-tag fastener 918, the previously placed fastener(s) may be used to stabilize the gastric wall. The fasteners may be used to assist in forming of a plication or in retracting and positioning the gastric wall for fastening another component, such as a stoma, sleeve or attachment ring. Similarly, other gripping means, such as vacuum, transmural hooks and the like, may be used to facilitate placement of retention elements 20 for fastening another component (e.g. cuff or bypass tube) of the system.

Figure 5:
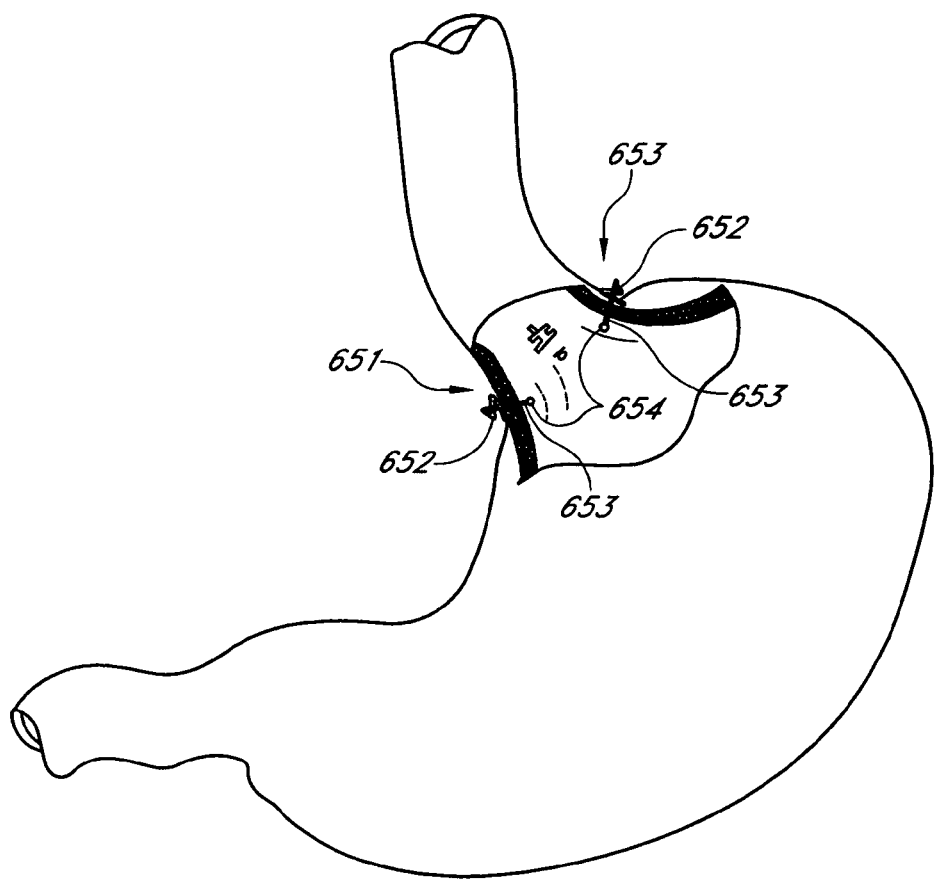
FIG. 5 shows a fastener device being driven through a single tissue layer, with the attachment means positioned adjacent a mucosal surface and the cone shaped spring positioned on the serosal surface.

FIG. 5 shows the attachment or fastener device 651 being driven through a single tissue layer, with the attachment means 654 on the end of the post 653 positioned within the passageway, and the cone shaped spring positioned 652 on the serosal side. The embodiment shown in FIG. 5 is preferably configured so that its installation does not narrow the passageway of the organ. Delivery of fastener embodiments communicating with the exterior of a hollow organ as shown in FIG. 5 may incorporate means to control capture of other structures. Though it may be clinically desirable to capture other structures as in the case of capturing the diaphragm by fasteners placed in the cardia of the stomach it is more likely that this would be undesirable. Fastening means could incorporate shielding means and/or means to invaginate the organ wall as the fastener is advanced through the organ wall.

Figure 6:
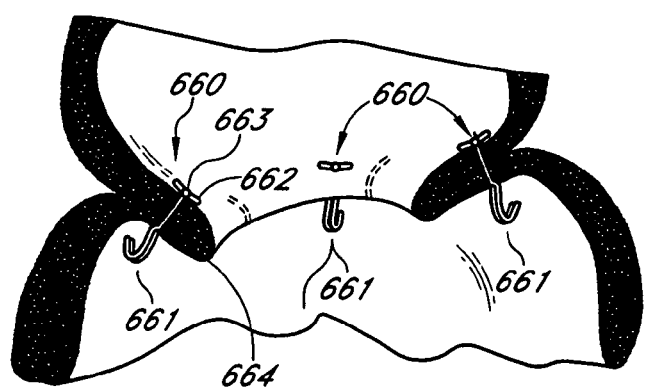
FIG. 6 shows another embodiment of a fastener system comprising a hanger that as shown, may also function to hold two layers of folded tissue together (a plication). This fastener has a toggle that pivots on a hinge so that is can be aligned with the post as it is passed through tissue layers, and can then be pivoted to hold the tissue layers together.

FIG. 6 shows another embodiment of a fastener 660 comprising a hanger 661 that also functions to hold two layers of folded tissue together. This fastener has a toggle 662 that pivots on a hinge 663 so that is can be aligned with the post 664 as it is passed through tissue layers, and can then be pivoted to hold the tissue layers together.

The toggle 662 helps to distribute forces that hold the fastener 660 in place over the length of the toggle 662, and also prevents the fastener 660 from being pulled through the hole. Alternative to the toggle 662, a similar functioning apparatus such as a disc or a multi-arm umbrella could also be used to distribute forces on the adjacent tissues while preventing the fastener 660 from passing through the hole. This fastener functions similarly to the T-tag fasteners described herein. Some of the attachment structures described herein such as that of FIG. 6 are illustrated in connection with tissue plications; however, these attachment structures may also be used transmurally, i.e., through one tissue layer.

Figures 7, 8:
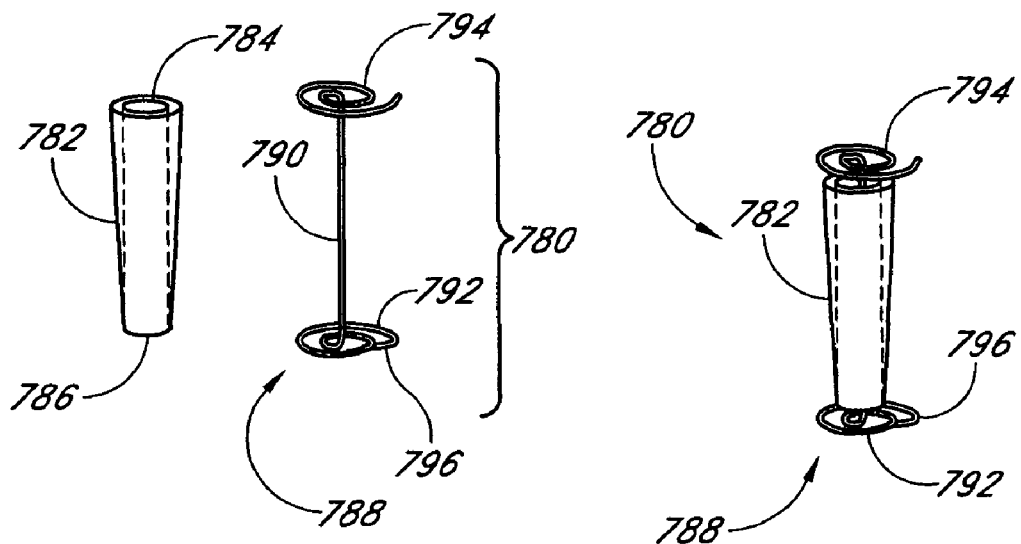
FIG. 7 is an exploded view of a transmural tissue anchor and spacer.
FIG. 8 shows the tissue anchor of FIG. 7 in a deployed condition.

FIG. 7 is an exploded view of a rivet-like surgical fastener 780. The surgical fastener 780 has two components, a spacer or rivet tube 782 and a rivet cap wire 788. The rivet tube 782 can be made of a biocompatible polymer or metal. The rivet tube 782 has a tapered distal end 786 an internal lumen 784 sized to allow passage of the rivet cap wire 788 in a straightened condition. In its deployed condition, the rivet cap wire 788 has a straight piercing section 796 on its distal end, followed by the distal button 792, which is a section of the wire formed into a circle or spiral. Next, is a straight central section 790 that connects the distal button 792 to the proximal button 794, which is another section of the wire formed into a circle or spiral. In certain embodiments, the rivet cap wire 788 is made of a highly resilient material, for example a superelastic NiTi alloy, which can be preformed into this geometry by cold working and/or heat treatment, and which will return to this geometry after being straightened out for insertion through the internal lumen 784 of the rivet tube 782. Rivet tube 782 can be constructed of a relatively bioinert material such as 304 or 316 SS or Ti unless the clinical situation suggests that a material that encourages a scar forming healing response as discussed earlier is desirable. Rivet tube 782 will typically have an outer diameter of approximately 0.25-1.5 mm with the inner diameter large enough to provide for passage of a pre-formed NiTi wire of approximately 2×-6× the diameter of the wire. The tapered tip will preferably have a minimum clearance to allow free passage between its inner diameter and the outer diameter of the NiTi wire. Wall thickness of tube 782 will typically be on the order of 0.002-0.005".

FIG. 8 shows the surgical fastener 780 of FIG. 7 in a deployed condition. The straight central section 790 of the rivet cap wire 788 extends through the internal lumen 784 of the rivet tube 782, and the distal button 792 and proximal button 794 are formed into a substantially planar tissue-retaining geometry approximately perpendicular to the rivet tube 782 at the proximal and distal ends of the rivet tube 782. The straight piercing section 796 may be bent inward slightly so that the distal button 792 protects it from inadvertently piercing any adjacent tissue structures when in the deployed condition.

Figure 9:
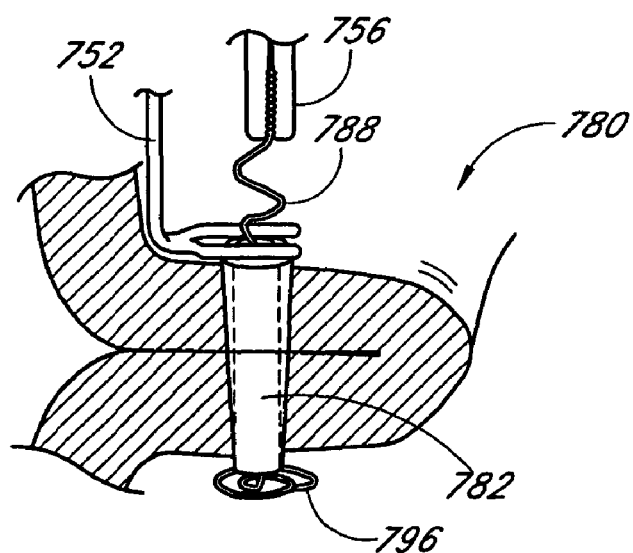
FIG. 9 shows the tissue anchor of FIG. 7 being removed.

The construction of the surgical fastener 780 allows it to be removed if it is desired to reverse or revise the surgical procedure. FIG. 9 shows the surgical fastener 780 of FIG. 7 being removed. A grasping tool or other rivet tube retaining tool 752 engages the proximal end of the rivet tube 782 and a grasper 756 grasps the rivet cap wire 788 near its proximal and withdraws it from the rivet tube 782 to release the fastened tissue.

The attachment fasteners described in FIGS. 7-9, although shown passing through two tissue layers of a plication, can be used to pass through one tissue layer as well.

Figure 10A:
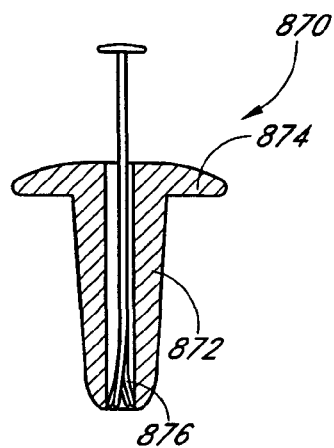
FIGS. 10A-10D illustrate an alternate tissue anchor design.
Figure 10B:
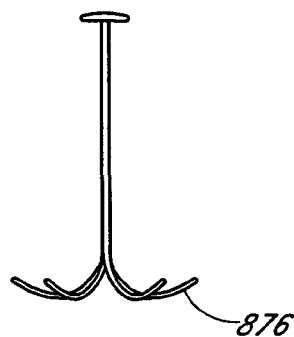
Figure 10C:
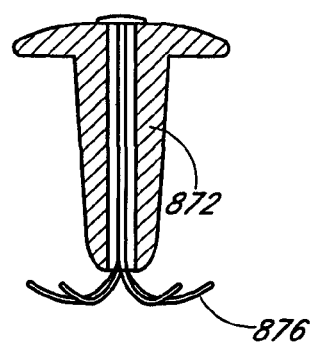
Figure 10D:
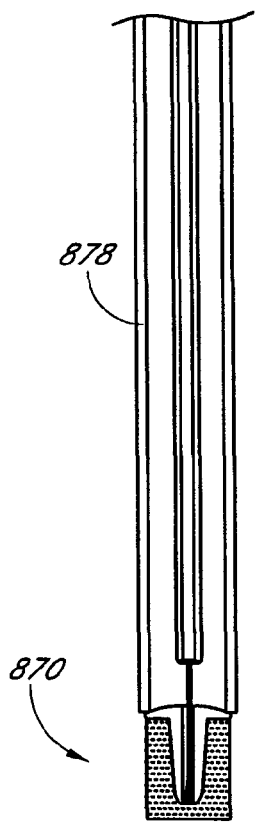

FIGS. 10A-10D shows an alternate rivet design 870 in which the rivet tube 872 is provided with an attached or formed in place proximal rivet cap 874. The proximal rivet cap 874 can be formed as described earlier or formed as shown in FIG. 10A. FIG. 10B shows a multi fingered distal cap 876 that can be deployed by an axial advancement of the fingers, as shown in FIG. 10C. With a design that includes a proximal eye or other means of coupling, the fingers could also be retracted back into the rivet body 872 if so desired. The fingers 876 of this rivet do not require the degree of superelasticity of the rivets described in FIGS. 7-9 and could optionally be made from 304, 316 or other stainless steels in addition to NiTi alloys, as well as other metals. FIG. 10D shows an exemplary apparatus 878 for deploying this type of rivet.

Figure 11A:
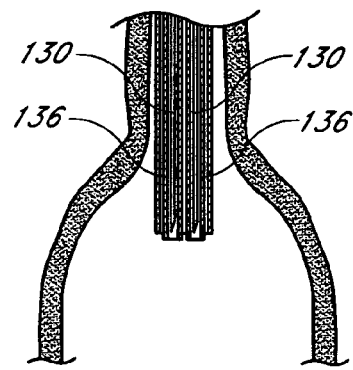
FIGS. 11A-11D show wire fasteners useful for placing a transmural tissue anchor.
Figure 11B:
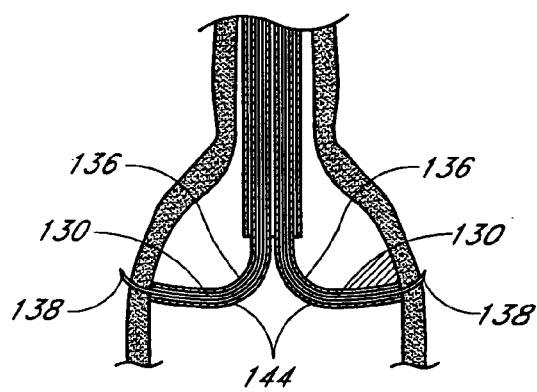
Figure 11C:
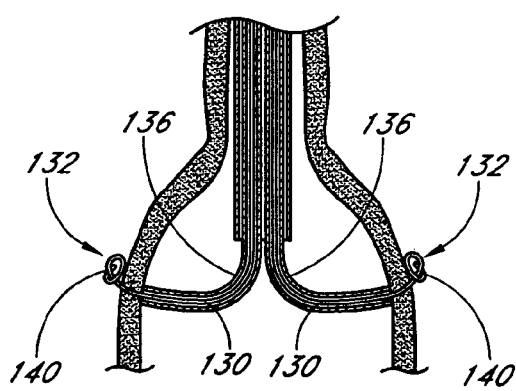
Figure 11D:
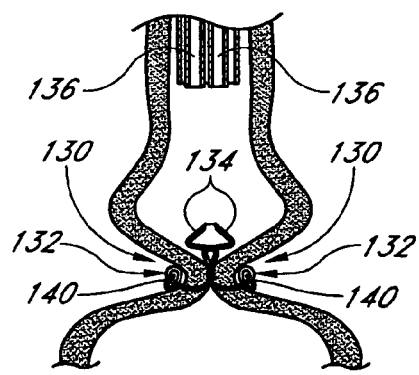

Stapling, suturing or other attachment of the implant is preferably accomplished transesophageally with the use of a flexible endoscope. Sutures may be placed into the muscularis, through the muscularis and/or full thickness through the muscularis and serosa based upon the clinical situation. One method for accomplishing this involves the use of wire fasteners 130 that are formed with a "button" retention element end 132 and a "twist tie" or other device attachment end 134, which are shown in FIGS. 11A-11D. In certain embodiments, the wire fasteners 130 are formed from a superelastic NiTi alloy so that the fasteners can be straightened out and passed through a delivery cannula 136, as shown in FIG. 11A. The distal tip 138 of the wire can be sharpened so that it will penetrate tissue. A portion of the distal end of the wire is formed so that it will assume a circular or spirally curled "button" shape 132 after it has passed through the tissue, as shown in FIG. 11B. The "button" shape 132 attaches the fastener to the stomach wall and prevents it from being pulled out through the tissue. The curl of the "button" 132 can be shaped so that it protects the sharpened distal tip 138 of the wire and prevents it from damaging the stomach wall or surrounding tissues after the fastener is deployed. There is an approximately 90 degree bend 140 in the wire just proximal to the "button" portion 132. A portion of the proximal end of the wire is formed to create the "twist tie" 134, which reforms when the wire fastener 130 is pushed out of the delivery cannula 136, as shown in FIG. 11C. The "twist tie" 134 can be a helical curl or other shape that will entangle and interlock with a mating fastener when the two are approximated to one another, as shown in FIG. 11D. Alternately, the proximal end 134 of the wire fastener 130 can form a loop for attachment of standard suture materials.

The delivery cannula 136, which may be configured with a torquable shaft with a fixed or variable curve 144 at the distal end, is used to deliver the wire fasteners 130 to the desired location. The distal end of the delivery cannula 136 is advanced until it contacts the stomach wall, then a pusher wire or the like is used to advance the wire fastener 130 through the delivery cannula 136, as shown in FIG. 11A. As the wire fastener 130 exits the delivery cannula 136, the sharpened distal tip 138 penetrates the stomach wall. The "button" portion 132 of the wire assumes its curved configuration distal to the stomach wall as the fastener 130 is advanced farther out of the delivery cannula 136, as shown in FIG. 11B. These steps are repeated to place a second wire fastener 130 in the opposite wall of the stomach. Then, the two delivery cannulas 136 are withdrawn while continuing to advance the wires out of the delivery cannulas to allow the "twist tie" portions to assume their helical curled shape proximal to the stomach wall and the two fasteners are approximated to one another so that the two "twist tie" portions intertwist with one another as they exit the delivery cannulas to attach the two walls of the stomach together, as shown in FIG. 11D. Alternatively, the wire fasteners 130 can employ a loop, rather than a "twist tie" to enable approximation using a secondary means such as sutures. A line of fasteners 130 can be thus deployed to create a gastroplasty pouch or band, or used to attach an attachment cuff or bypass tube to the stomach wall.

In an alternate embodiment, the wire fasteners may be configured to have a "button" portion 132 on both ends of the wire. These fasteners can be deployed laparoscopically to penetrate both walls of the stomach with a "button" 132 placed on each side of the stomach to attach the walls together. Such fasteners can be combined with buttressing reinforcements such as pledgets made from Teflon, bovine or porcine tissue or other know materials. "T-tag" type fasteners could be applied to this use and type of application.

Figure 12A:
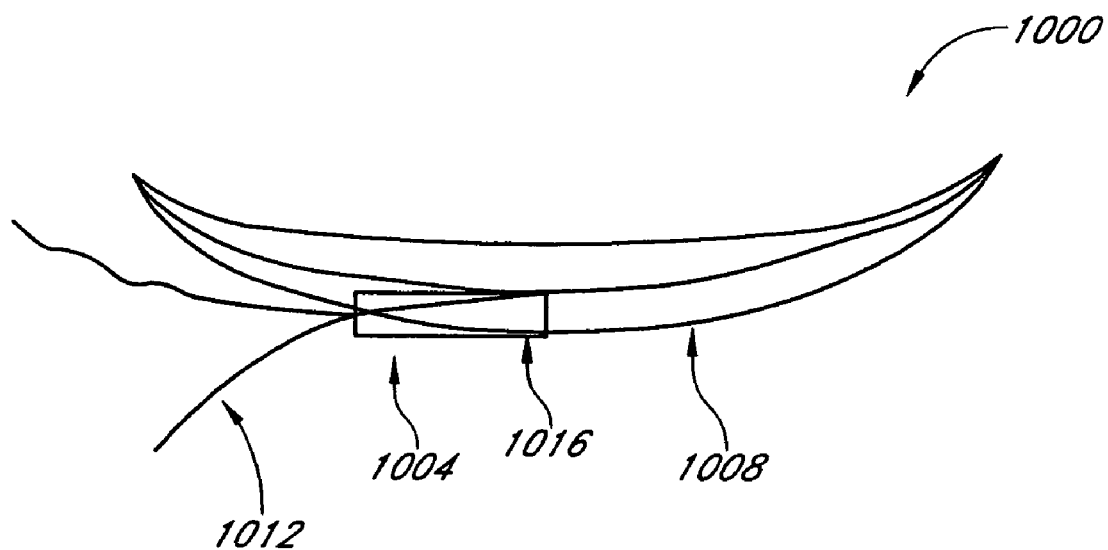
FIGS. 12A-12B show two views of a T-tag embodiment of a tissue anchor.
Figure 12B:
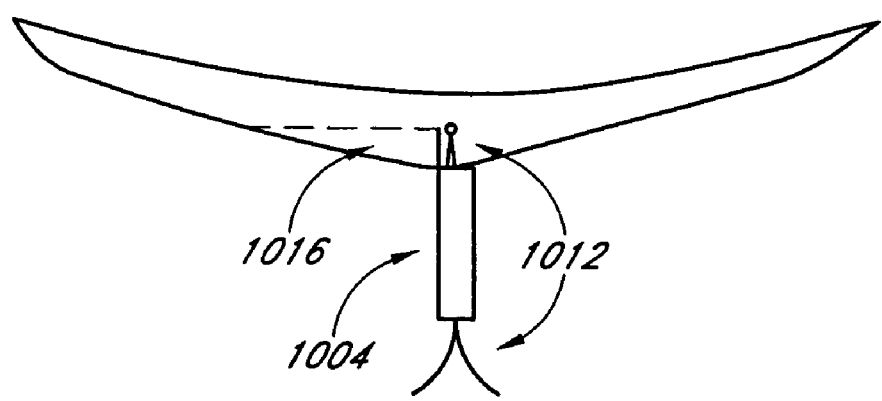

FIGS. 12A-12B illustrate a T-tag fastener 1000 with a tubular standoff stem 1004 that is recessed inside of the T-member 1008 during insertion of the fastener. The T-member 1008 of the fastener can be straight, curved or another geometry, such as those described herein. Two strands of suture thread 1012 are attached at approximately the center of the T-member 1000 and pass through the lumen of the tubular standoff 1004. The tubular standoff 1004 has a length corresponding approximately equal to or greater than the thickness of the tissue at the intended attachment point. There is a groove or recess 1016 found in the T-member 1008 of the fastener adjacent to where the suture threads 1012 are attached. The recess 1016 in the T member 1008 is sized to receive the tubular standoff 1004 when the T-tag fastener 1000 is in the undeployed position for insertion of the fastener, as shown in FIG. 12A. FIG. 12B shows a side view of the T-tag fastener 1000 in the deployed position after insertion through the tissue. The suture threads 1012 can be used to attach a gastrointestinal sleeve device, an attachment cuff or other implantable device to the tissue and the tubular standoff 1004 prevents the application of excess pressure that might lead to tissue necrosis and erosion at the attachment point.

One of the difficulties encountered with the use of fine filaments, such as suture threads, for attachment of implants within the gastrointestinal system is that the filaments can cut through the tissue in the same way that a wire cheese cutter cuts through a block of cheese. When the force on the filaments is perpendicular to the tissue wall, the force can be distributed over the tissue with a pledget and/or with a T-tag fastener. However, when there is a large enough component of force transverse to the tissue wall, the filaments can cut sideways through the tissue. The use of a stem, for example the tubular standoff as described above can distribute the force sufficiently to avoid this cheese cutter effect.

In a preferred embodiment the attachment structure, for example a non-plicating transmural attachment structure, would maintain the natural anatomical shape of the stomach and move with the stomach rather than constrain its movements. An attachment structure that does not interfere with the natural movements and shape of the stomach may reduce the cheese cutter effect and/or other failure modes that may increase the risk of relocation of the T-tags into the stomach.

FIG. 13 illustrates a T-tag fastener 1100 with a stem 1104 attached to the T-member 1108 to reduce the cheese cutter effect. In the example shown, the T-member 1108 of the fastener is curved to distribute the forces that are perpendicular to the tissue wall 1116. The stem 1104 extends approximately perpendicular the T-member 1108 and has sufficient thickness to distribute the forces transverse to the tissue wall 1116 to avoid the cheese cutter effect. One or more suture threads 1112 are attached to the end of stem 1104 for attachment of an implanted device. Preferably, the stem 1104 has a length corresponding approximately equal to or greater than the thickness of the tissue at the intended attachment point to act as a standoff to prevent excess pressure on the tissue at the attachment point.

FIG. 14 illustrates a T-tag fastener 1200 similar to the embodiment shown in FIG. 13 with the addition of a living hinge 1204 molded into the fastener 1200 at the point where the stem 1208 attaches to the T-member 1212. This living hinge 1204 allows the stem 1208 to fold against the T-member 1212 for a low profile during insertion of the fastener 1200.

Figure 15A:
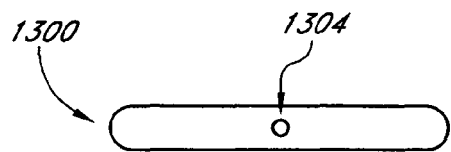
FIGS. 15A-15B, 16A-16B, 17A-17B, 18A-18B, 19A-19B illustrate various T-tag embodiments.
Figure 15B:
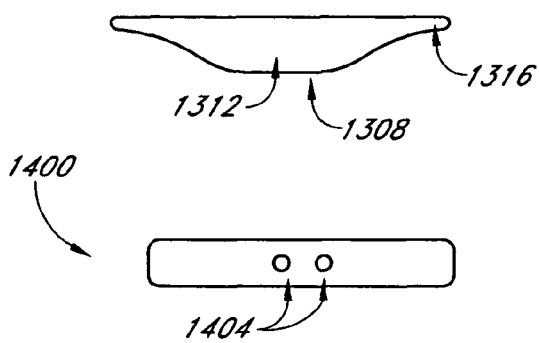

FIGS. 15A & 15B illustrate a tapered T-member 1300 for a T-tag fastener with a single eyelet 1304 for attachment of a suture or other filament. The contoured tissue-contacting surface 1308 of the tapered T-member 1300 serves to distribute the attachment force for an implanted device smoothly across the tissue to eliminate any stress concentrations or pressure spots that could cause tissue necrosis and erosion. The tapered thickness of the T-member provides a gradual stiffness transition from the stiffer middle section 1312 to the more flexible outer edges 1316 of the T-member 1300, which allows the T member 1300 to flex and thereby further serves to minimize stress concentrations and higher pressure spots in the tissue at the attachment site.

Figure 16A:
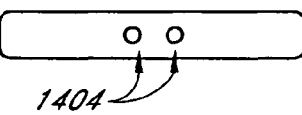
Figure 16B:
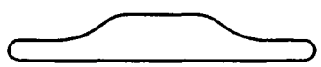

FIGS. 16A & 16B illustrate a tapered T-member 1400 for a T-tag fastener similar to FIGS. 15A & 15B, but having a double eyelet 1404 for attachment of one or more sutures or other filaments.

Figure 17B:
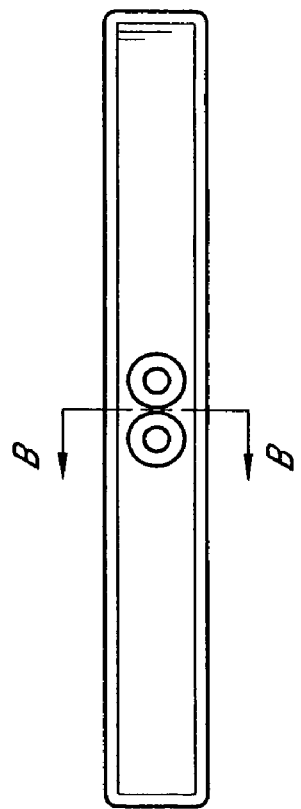
Figure 17A:
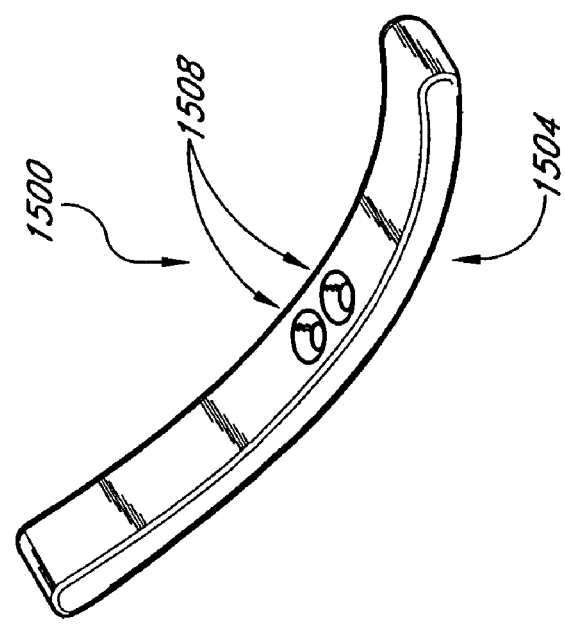

FIGS. 17A & 17B illustrate a curved T-member 1500 for a T-tag fastener. The convex curved tissue-contacting surface 1504 of the curved T-member 1500 serves to distribute the attachment force for an implanted device smoothly across the tissue to minimize any stress concentrations or higher pressure spots that could cause tissue necrosis arid erosion. The T member 1500 has a double eyelet 1508 for attachment of a suture or other filament. The T-member is preferably molded of a fairly rigid, high strength biocompatible polymer such as PEEK.

Figure 18A:
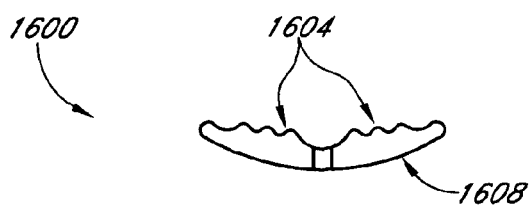
Figure 18B:
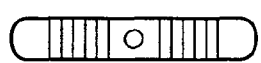

FIGS. 18A & 18B illustrate a curved T-member 1600 for a T-tag fastener with a pattern of alternating grooves and ridges 1604 for controlled flexibility. The convex curved tissue-contacting surface 1608 of the T-member 1600 serves to distribute the attachment force for an implanted device smoothly across the tissue to minimize any stress concentrations or pressure spots that could cause tissue necrosis and erosion. The pattern of alternating grooves and ridges 1604 formed on the opposite surface of the T-member 1600 increases the flexibility of the T-member 1600, which further serves to minimize stress concentrations and higher pressure spots in the tissue at the attachment site.

Figure 19A:
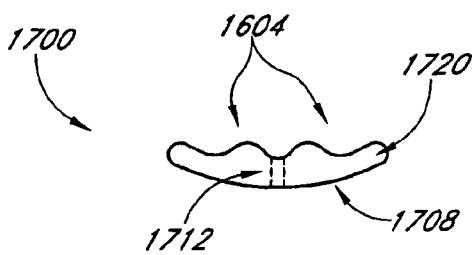
Figure 19B:
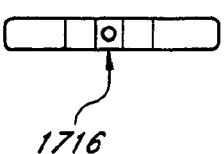

FIGS. 19A & 19B illustrate a curved T-member 1700 for a T-tag fastener with a pair of ridges 1704 for controlled flexibility. The convex curved tissue-contacting surface 1708 of the T-member 1700 serves to distribute the attachment force for an implanted device smoothly across the tissue to eliminate any stress concentrations or pressure spots that could cause tissue necrosis and erosion. The pair of ridges 1704 near the center of the T-member 1700 create a stiffer middle section 1712 adjacent to the suture eyelet 1716 and a gradual stiffness transition to the more flexible outer edges 1720 of the T-member 1700, which further serves to minimize stress concentrations and higher pressure spots in the tissue at the attachment site.

FIG. 20 illustrates a tapered, curved T-member 1800 for a T-tag fastener with enlarged barbell shaped areas 1804 on the ends of the T-member 1800. The convex curved tissue-contacting surface 1808 and the tapered arms 1812 of the T-member 1800 serve to distribute the attachment force for an implanted device smoothly across the tissue to minimize any stress concentrations or higher pressure spots that could cause tissue necrosis and erosion, while the barbell shaped ends 1804 on the arms 1812 of the T-member 1800 serve to minimize any stress concentration in the tissue at the ends of the arms 1812 of the T-member 1800. The bulbous barbell ends 1804 can be optionally combined with other materials or configurations described herein to provide flexibility to further reduce pressure concentrations. Optionally, the bulbous barbell ends 1804 can be formed in a hollowed out or spoon-shaped configuration to increase flexibility and further reduce the stress on the tissue. Optionally, a stainless steel pin 1816 or the like may be inserted into the molded polymer T-member 1800 to support the stress of the suture attachment.

FIGS. 21A-21D illustrate an X-tag anchor embodiment 1900 and deployment of an X-tag anchor embodiment 1900. FIG. 21A shows two T-members 1904 placed one on top of the other in a cross configuration. FIG. 21B shows two T-members 1904 in series within a delivery needle 1908. FIG. 21D shows another view of the two T-members 1904 inside the needle 1908. FIG. 21C shows a cross-section of the X-tag anchor embodiment 1900 illustrating the looped suture 1912 extending from the T-members 1904.

Figure 22B:
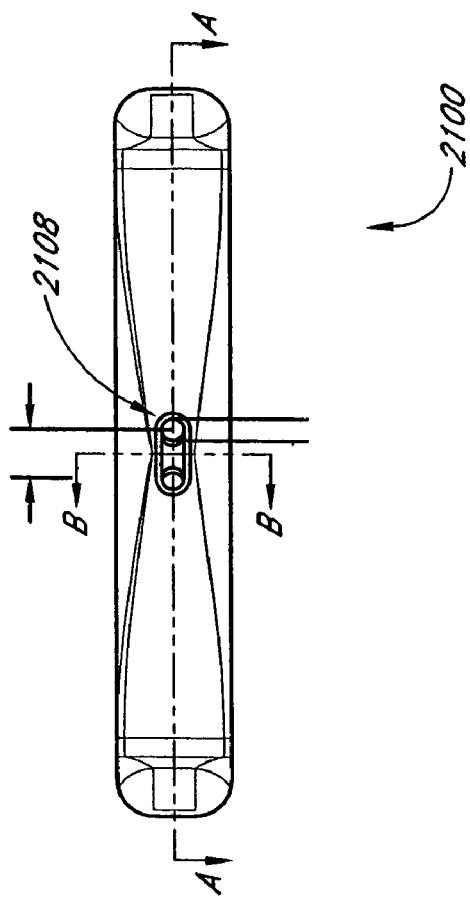
Figure 22A:
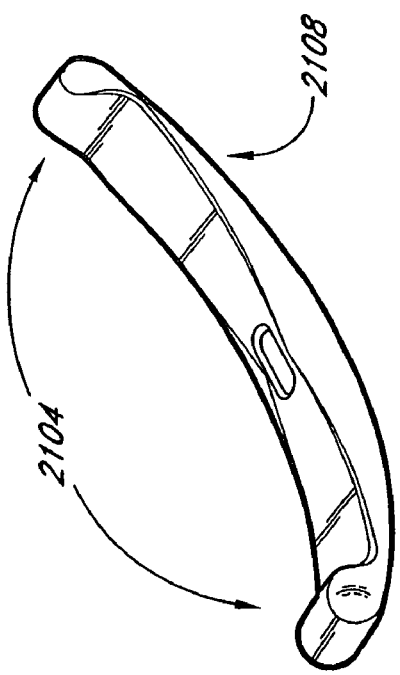
Figure 25A:
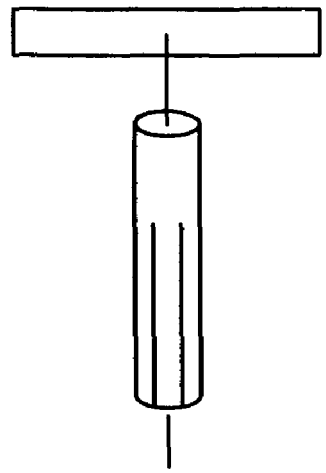
Figure 25B:
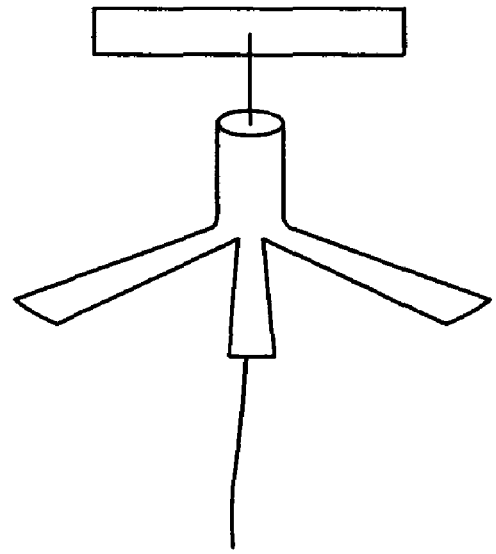
Figure 26A:
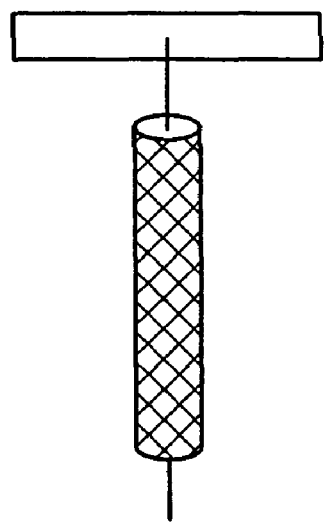
Figure 26B:
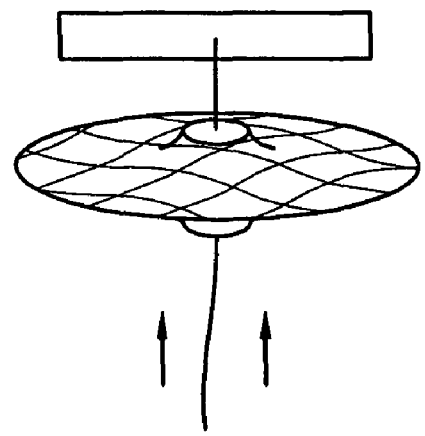

FIGS. 22A-22B illustrate an injection moldable tapered, curved T-member 2100 for a T-tag fastener with an elliptical cross section as shown in FIG. 22B and rounded ends 2104 on the arms of the T-member 2100. The upturned, canoe-shaped ends 2104 of the T-member 2100 are a variation on the barbell-shaped ends 1804 shown in FIG. 20.

This and other alternate configurations can be used to optimize pressure distribution and flexibility of the T-member. The T-member 2100 has a double eyelet 2108 for attachment of a suture or other filament and a groove between the eyelets so that the bight in the suture will be recessed into the body of the T-member 2100. The T-member 2100 is preferably molded of a fairly rigid, high strength biocompatible polymer such as PEEK.

FIGS. 23A-23B illustrate a T-tag fastener 2200 with a hydrogel disc 2204 that can be placed between the deployed T-member 2208 and the extragastric surface. The disc 2204 could be delivered through the T-tag delivery needle. It could unroll after passage through the needle. The hydrogel disc 2204 acts as a buttress or pledget to distribute the forces transmitted between the T-member 2208 and the extragastric surface and thereby it strengthens the attachment of the T-tag fastener 2200. The hydrogel used in FIGS. 23A-23B can optionally be replaced with alternate materials described herein for example NiTi and fluoropolymers. A Hydrogel or other buttress or Teflon pledget for a T-tag could also deploy in some other manner. The disc configuration shown can be replaced with for example, braided or woven wires or filaments that would expand/deploy after passage through the needle (FIGS. 24A-24B), a Malecot-style deployable tubular structure (FIGS. 25A-25B) or other expandable or deployable configuration (e.g. FIGS. 26A-26B). Although FIGS. 23A-23B, 24A-24B, 25A-25B, and 26A-26B illustrate T-tag fasteners, such as 2200 in FIGS. 23A-23B used with T-members 2208, uses of the T-tag fasteners without T-members and just with the hydrogel disc 2204 of FIGS. 23A-23B or the woven filaments, Malecot-style tubular structure, or the expandable structure of FIGS. 24A-24B, 25A-25B, and 26A-26B, respectively, are also contemplated.

It may be beneficial to limit the pressure applied to the tissue in order to avoid tissue necrosis and erosion at the attachment points. A T-tag fastener can be configured with two suture threads going to the midpoint of the T-member, as shown for example in the anchor embodiment of FIGS. 12A-12B (or a single suture thread that passes through center of the T-member). As an alternative to the stem described above, the two suture threads are fused together or otherwise attached to one another over a selected distance from the T-member corresponding to the thickness of the tissue at the attachment point (for example about 10-15 mm). Alternatively, a single suture thread could be connected to the T-member, which divides into two suture threads at a selected distance from the T-member. The T-member can be passed through the tissue wall using an insertion cannula or the like and ends of the suture threads can be used to tie the fastener to an anchor ring, gastrointestinal sleeve or other device. In this example a gap of 2-3 mm, or more, between the T-member on the serosal surface and the device on the mucosal surface is assured. Thus, the suture threads can be tied very securely without creating excessive pressure on the tissue at the attachment points. This would simplify the procedure because the surgeon or endoscopist would not have to judge the knot tension to get the device snug against the mucosa without compressing the tissue.

Alternatively, the two suture threads can be tied together to create a stop at a selected distance from the T-member. This is less preferred because the knot would likely have to be pushed through the tissue to allow the T-member to pivot to the deployed position, then pulled back through the tissue. This would require more force as there would be drag on the knot and the hole through the tissue would be a bit bigger. Other alternatives to create a stop or common length of 2 sutures include use of a tightly fitting tube, for example heat shrink tubing, an adhesive (e.g. epoxy), a biodegradable adhesive (e.g. cyanoacrylate) or fusing the 2 filaments over the desired length. Use of a slidable tube for this purpose is described herein. Such tubes can be polymers (e.g. PE or Teflon) or metals (e.g. SS, NiTi or Ti) PB and Teflon tubes can be either heat shrinkable or of fixed diameter depending upon the desired performance.

In the above examples where it has been suggested that a fixed distance between the T-member and the device it is being used to attach is desirable it has been suggested that in some cases a distance greater than the thickness of the captured gastric wall may be clinically indicated. This is due to the ability/tendency/possibility that the gastric wall could react to the presence of a foreign body (the attachment structures) by thickening. In this event, in some cases, it can be clinically preferable that the preset distance accommodate some or all of this increase in wall thickness.

Figure 30A:
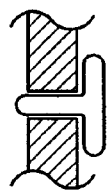
FIGS. 30A-30K illustrate inflatable balloon anchor adaptations.
Figure 30B:
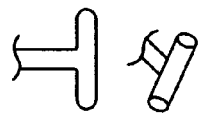
Figure 30C:
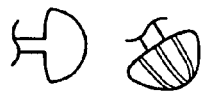
Figure 30D:
Figure 30E:
Figure 30F:
Figure 30G:
Figure 30H:
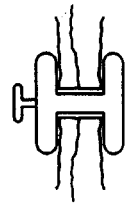
Figure 30I:
Figure 30J:
Figure 30K:
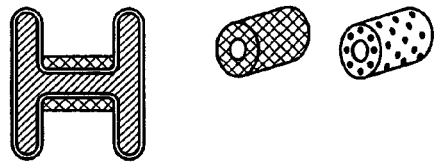

The previous applications discussed mucosal ingrowth as a means to stabilize and seal an implant device, and to assure long-term attachment in the stomach. Alternatively or in addition, the T-member of a T-tag fastener can be configured to encourage serosal ingrowth or fibrosis for stabilization at the serosal surface, as shown in FIG. 30K. Furthermore, the material passing through the tissue wall (e.g. suture, spacer tube) can be selected to form an optimal suture track by encouraging a desirable tissue reaction, for example fibrosis.) . Similarly the T-member could be coated or treated to achieve these properties. Materials and coatings for these purposes have been described in the prior applications.

A dissolvable sheath (e.g. sugar, gelatin or other rapidly dissolving material) or stem can be used to control the position of a knot in the suture as it can be used to prevent the knot being tied where the sheath is over the sutures. Furthermore, structures and methods that encourage tissue motion relative to the suture and the suture track can have an impact on tissue healing that can be beneficial or detrimental depending upon the clinical situation.

The T-member of a T-tag fastener can be configured with a sharpened distal tip to pierce the tissue without the need for a separate insertion cannula. The T-member can be detachably mounted on a pusher shaft with a female socket on the proximal end of the T-member into which the pusher shaft is inserted. The sharpened distal tip of the T-member can be made from a material that dissolves or is bioabsorbable to provide a less traumatic long term implants. T-tags can be configured with other T-member or cross bar shapes, with a single suture, with or without needles on the ends of the sutures, and with a variety of cross member materials. These materials can include polymers such as fluoroplymers, PU, PET, PEEK or silicone. They can also be made from metals such as 55, NiTi or Ti or polymers reinforced with metals or other materials well known in the art (e.g. glass or aramid fibers. Furthermore, is some clinical situations materials that are biodegradeable, as described in the prior applications, could be beneficial.

FIGS. 27A-27B show a T-tag fastener 222 with a spacer 224 to avoid excessive pressure on the tissue. The fastener 222 has a cross member or "T" 226 that is attached to a "stem" 228 at or near the mid-point of the T. For "blind" deployment of the fastener, the attachment point between the T 226 and the stem 228 can be configured with a flexible hinge to facilitate insertion through a needle or cannula. The stem 228 is constructed with a spacer 224 that may be configured as a cylindrical shoulder on the stem as shown or, alternatively, a ring or bump on the stem of the fastener may also serve as a spacer. An attachment means 230 is provided at the proximal end of the stem for attachment of a proximal cap 232. The attachment means 230 may include barbs, detents, crimp connections, screw threads, or the like, with corresponding structures or attachment means 234 on the proximal cap 232 for an easy and reliable attachment. Optionally, an elongated tail member 236 may be attached to the proximal end of the stem 228 to aid in guiding the proximal cap 232 into place on the attachment means 230 of the T-tag fastener 222. The tail 236 may be configured as a pair of elongated sutures. The tail 236 may be detachable or it may be made so that it can be cut off of the fastener after it has been placed.

Generally, the spacer 224 should be configured to limit the amount of compression applied to the gastric or esophageal wall upon deployment of the fastener 222. Where some compression is desired, the spacer distance, that is the distance along the stem from the T 226 to the proximal cap 232 after deployment, should be slightly less than the total thickness of the tissue and other structures to be attached. The spacer distance should take into account whether a single-wall transmural attachment or a double-wall plicated attachment is intended, as well as the thickness of any device structures that will be held by the fastener. In cases where it is not necessary to apply compression, the spacer distance may be greater than the total thickness of the tissue and other structures to be attached.

In an alternate embodiment of the T-tag fastener 222 of FIGS. 27A-27B, rather than using a fixed-length spacer, the attachment means 230 may be configured to allow the proximal cap 232 to be attached at different distances from the T cross member 226. This would allow the operator to select the correct spacer distance at the point of use and even to vary the spacer distance from one fastener to the next depending on tissue and device thickness at the attachment point. The correct spacer distance may be determined by imaging techniques such as fluoroscopy or ultrasound or it may be determined by using a force limiting or measuring mechanism in the fastener delivery and deployment device.

The T-tag fastener 222 of FIGS. 27A-27B can be deployed directly, for example through a plication of the gastric wall, with a needle attached to the proximal end of the tail member 236. Once the tail 236 has passed through the tissue, the proximal cap 232 is threaded onto the tail. The proximal cap 232 is then attached to the stem 228 of the fastener by holding tension on the tail 236 and pushing the proximal cap 232 until the attachment means 234 of the proximal cap engages the attachment means 230 on the stem 228. The tail 236 can then be removed from the fastener 222. Alternatively, the tail 236 can be used to attach another device to the T-tag fastener 222. The T-tag fastener 222 of FIGS. 27A-27B can also be deployed blindly, for example for transmural attachment through the gastric wall. The fastener 222 is inserted through a needle or cannula by pivoting the T 226 so that it is approximately parallel to the stem 228. The needle or cannula is used to pierce through the tissue to be attached; then the T 226 is pushed out of the cannula on the far side of the tissue using a pusher rod or tube that extends through the cannula. The needle or cannula is withdrawn and the T 226, which is now approximately perpendicular to the stem 228, is snugged up to the back surface of the tissue with a little tension on the tail member 236. After the needle is withdrawn, the proximal cap 232 is threaded onto the tail 236. The proximal cap 232 is then attached to the stem 228 of the fastener by holding tension on the tail 236 and pushing the proximal cap 232 until the attachment means 234 of the proximal cap engages the attachment means 230 on the stem 228. The tail 236 can then be removed from the fastener 222. The diameter of the spacer 224 and/or the stem 228 between the T 226 and the proximal cap 232 can be minimized to reduce compression on the surrounding tissue or, alternatively, the spacer 224 and/or stem 228 can be configured to seal the puncture through the tissue. FIG. 27B shows the T-tag fastener 222 of FIG. 27A deployed through the gastric wall.

A gastrointestinal sleeve, a mounting cuff or ring or other device may be attached directly to the gastric wall using several of the T-tag fasteners or other attachment devices as rivets. Alternatively, the stem and/or the proximal cap may be configured with a nubbin (FIG. 30H), a ring (FIG. 30J), a hook, a loop (FIG. 30I), or the like, for attaching another device to. As another alternative, the suture tails may be used for tying a device to the fasteners.

FIGS. 28A-28D show another T-tag fastener 240 with a spacer 242 to avoid excessive pressure on the tissue. In this case the T-tag fastener 240 is specially configured for low-profile blind deployment through a needle or cannula 248. The cross member or T 244 is attached at or near its mid-point to a flexible stem 246, which in the example shown is configured as a pair of elongated sutures. A sliding spacer 242 or standoff with a tubular configuration is threaded onto the sutures 246. The T-tag fastener 240 is prepared for insertion as shown in FIG. 28A by inserting it into the delivery cannula 248 with the T 244 at the distal end, followed by the spacer 242 in a tandem configuration. The sutures 246 extend proximally through the delivery cannula 248. The tandem configuration provides a low profile for delivery through the cannula 248. The fastener 240 may be loaded into the delivery cannula 248 in either an antegrade or retrograde direction, depending on what is most convenient and economical.

The low profile provided by the tandem configuration of the T member 244 and spacer 242 is desirable to minimize the size of the needle or cannula 248 needed to deliver the fastener 240. This is important not only for minimizing the size of the tissue puncture, but also to reduce the amount of force needed to deliver and deploy the fastener 240 through an endoscope. The delivery needle or cannula 248 will preferably be 17 gauge or smaller, more preferably 19 gauge or smaller.

The T-tag fastener 240 is typically deployed as a blind fastener, for example for transmural attachment through the gastric wall. The delivery cannula 248 is used to pierce through the tissue to be attached; then the T member 244 is pushed out of the cannula 248 on the far (serosal) side of the tissue using a pusher rod or tube that extends through the cannula 248. The needle or cannula 248 is withdrawn and the T member 244, which is now approximately perpendicular to the sutures 246, is snugged up to the back surface of the tissue with a little tension on the sutures 246, as shown in FIG. 28B.

The sliding spacer 242 is pushed out of the delivery cannula 248 with the pusher rod or tube and slid distally along the sutures until it contacts the T member 244, as shown in FIG. 28C. Several T-tag fasteners 240 can be inserted transmurally in this manner around the gastroesophageal junction or elsewhere in the gastrointestinal system using a flexible gastroscope or the like. The sutures 246 can then be used to attach a gastrointestinal sleeve, a mounting ring or cuff or other device 238 to the mucosal surface of the gastric wall, as shown in FIG. 28D. The spacers 242 prevent excessive pressure on the gastric wall that could lead to undesirably high ischemia and eventually to tissue necrosis.

Inflatable/Injectable Soft-Tissue Anchor Attachment Structures

Many suitable soft-tissue anchors include monolithic anchors, multi-component anchors, flip-style anchors, expanding anchors, rivet-style anchors, zip-tie style anchors, and sliding knot-style anchors. Expanding balloon anchors may also be used for transmural, suture-less attachment that may be easily deployed through a small delivery needle and flexible endoscope and that have large surface areas that interact with surfaces of soft-tissue, such as the outer surfaces of the esophageal or gastric wall, for increased attachment strength.

Figure 29C:
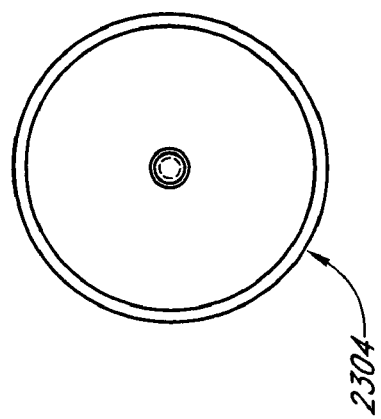
FIGS. 29A-29C show an inflatable balloon cuff-link anchor.
Figure 29B:
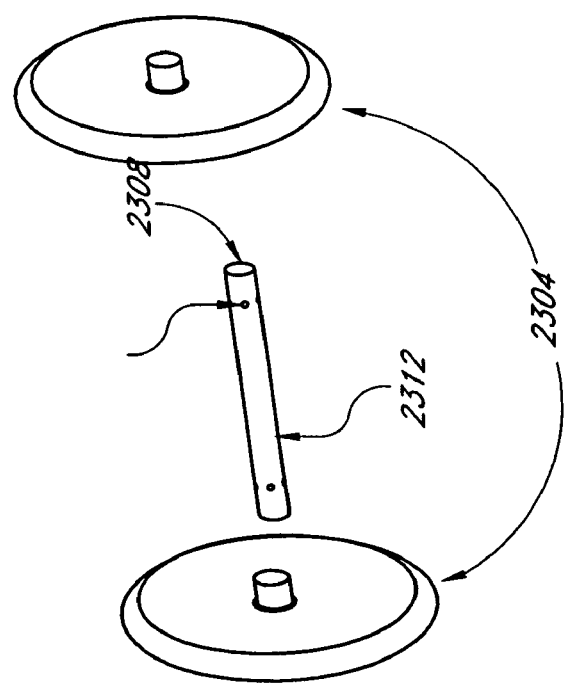
Figure 29A:
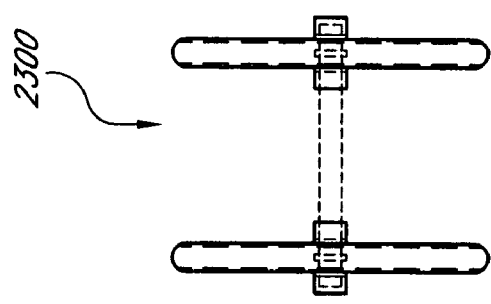

FIGS. 29A-29C show an inflatable attachment structure 2300 comprising balloon anchors 2304 that interface with the outer surface of the esophageal or gastric wall. Such inflatable anchor attachment structures 2300 have large surface areas, as shown in the balloon anchor 2304 cross-section of FIG. 29C, that interact with the esophageal or gastric wall which gives them increased attachment strength. The large surface area, flexible nature, rounded edges, and curved profiles of these structures 2300 decrease stress concentrations which can lead to pressure necrosis and ischemia and subsequent anchor detachment. Furthermore, these anchor structures 2300 are easy to deliver, particularly when only the inner surface of the esophageal or gastric wall is accessible. The small size of the anchors 2304 permits delivery via a small delivery needle through a flexible endoscope. Because the anchors 2304 do not require the use of sutures, the long-term embrittlement or fracture issues associated with sutures are avoided. The balloons 2304 may be inflated in-situ after delivery with, for example silicone; the silicone subsequently cures resulting in an anchor 2304 with very large surface area.

In some aspects of the invention the balloon anchor 2304 is preferably an inflatable or injectable dual-ended balloon anchor for soft-tissue which when expanded has a barbell-style profile. When unexpanded this anchor 2304 folds up and fits into a small delivery needle. The anchor 2304 is formed of thin-wall silicone or polyurethane that is expandable. After the anchor 2304 is delivered to the desired soft-tissue location via a delivery needle and flexible endoscope it is expanded, preferably with silicone, while in place. After the silicone cures the anchor 2304 attains its barbell-style profile with very large surface area interfacing with the outer surface of the soft-tissue. This large surface area helps prevent pull-out of the anchor 2304. The ratio of expanded surface area to unexpanded size is unmatched by other systems and provides maximum pullout strength with minimal tissue defects or trauma. Furthermore, after the silicone has solidified, concerns about leakage, deflation, and toxicity are eliminated, and the result is a reliable, long-term, implantable anchor 2304. The curvature, soft corners, and flexibility of the anchor balloons 2304 reduce stress concentrations thereby preventing pressure necrosis and ischemia and resulting in long-term attachment strength. The barbell ends also preferably comprise a self-sealing membrane or self-sealing end caps 2308 that seal upon removal of the inflation needle. In one embodiment, shown in FIG. 29B, the balloon anchors 2304 are connected by a hollow connection tube 2312 in which there are holes 2316 for inflating the balloon anchors 2304. The anchor 2304 is a fixed length anchor to prevent over-tensioning on the soft-tissue which leads to pressure necrosis. Because the anchor 2304 does not utilize any sutures, long-term embrittlement and fracture issues associated with sutures are avoided. Thus, this embodiment can be used to transmurally attach a gastric sleeve device with the anchor 2304 passing in its unexpanded state through the inner surface of the esophageal or gastric wall and being inflated at its final location at the outer surface of the esophageal or gastric wall.

Alternate anchor embodiments, as depicted in FIGS. 30A-30G, include:
- one-ended inflatable anchors (FIG. 30A),
- inflatable anchors with different end geometries including discs, convex or concave bowls, mushroom-heads, and "L" or "T"-profiles (FIGS. 30B-30G),
- inflatable anchors filled with polyurethane, saline, air, nitrogen, other low-to-high durometer silicones, PMMA (polymethyl methacrylate), bone cement, or any other inert gas, liquid, or semi-solid,
- multiple-component anchors with two end balloons connected via a connection tube or channel, the assembly being adhesively or otherwise bonded together,
- anchors comprised of osmotic membrane that expands and swells when immersed in a fluid environment, such that it would not have to be inflated by the user,
- anchors with connection channels of adjustable lengths adjusted based on tissue thickness measurements taken intra-operatively using concentric shafts with threads, ratchets, detents and other features.

All of the above anchor embodiments can be of various sizes. Mounting features, as shown in FIGS. 30H-30J, can also be added to the anchors to facilitate attachment. Tissue ingrowth surfaces can be incorporated into the anchor structures to improve the duration and stability of attachment.

Sleeve Assemblies

Figure 31A:
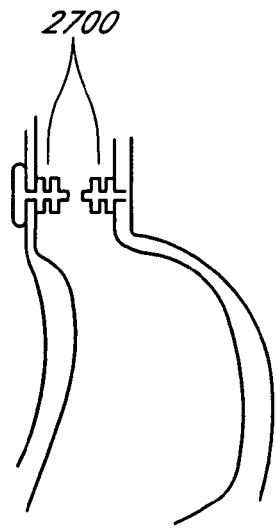
FIGS. 31A-31C illustrate a method for placing inflatable anchors.
Figure 31H:
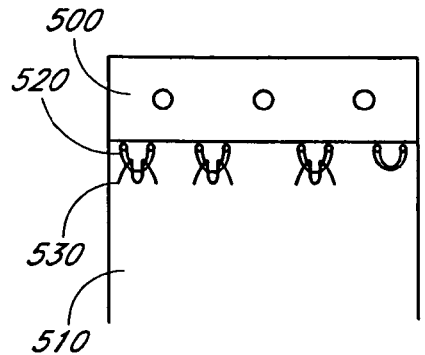
FIGS. 31D-31H illustrate various sleeve embodiments.
Figure 31B:
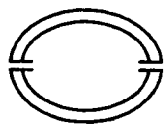
Figure 31C:
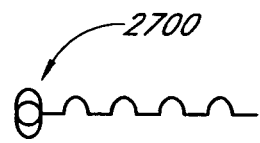
Figure 31D:
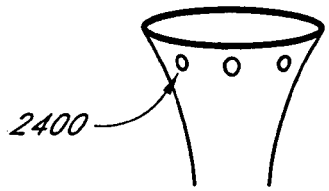
Figure 31E:
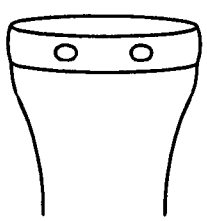
Figure 31F:
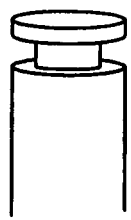

FIGS. 31D-31E show a bypass sleeve embodiment in accordance with the present invention. Aspects of the present invention provide for sleeve assembly features and an anchor mount feature for quick, easy, and secure attachment using a flexible endoscope. A sleeve safety ring feature of the sleeve assembly increases patient safety by preventing passage of the sleeve through the pylorus in the event of sleeve detachment. The sleeve and ring can be delivered via a flexible endoscope.

Preferably the sleeve embodiment 31D comprises a polyurethane sleeve with holes 2400 at the proximal end to quickly and securely attach over and engage with the internal anchor mount feature. The proximal end of this sleeve embodiment is very compliant and can accommodate the stretch and collapsing nature of the gastro-esophageal junction. This sleeve embodiment also incorporates a silicone ring safety device which can be inflated after sleeve delivery and prevents sleeve passage through the pylorus in case of detachment.

Figure 31G:
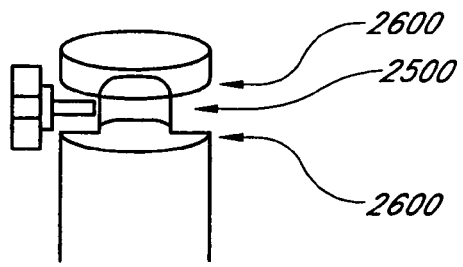

Alternate sleeve assembly embodiments include:
- a sleeve that incorporates a restriction or stoma 2500 at the proximal end of the sleeve to encourage early satiety (FIG. 31G),
- a sleeve mount feature which includes two compliant rings 2600 that allows the sleeve to float over the anchor mount features to accommodate the contraction and expansion of the GEJ while still providing for secure sleeve attachment to the soft-tissue (FIG. 31G),
- a sleeve mount feature which comprises j-hooks or loops to engage with and mount on the anchor mount ring feature.

In one aspect of the invention, a stem-frame positioning system that facilitates circumferential placement and spacing of the anchors inside a tubular soft-tissue structure, such as the gastro-esophageal junction, is provided, as shown in FIGS. 31A-31C. This method consists of the following steps:
- Place two anchors 2700 at the GEJ at opposing positions (FIG. 31A).
- Place the stem frame (FIGS. 31B-31C) over two tissue anchors 2700 to allow proper positioning of the other tissue anchors 2700.
- Insert remaining tissue anchors 2700.
- Remove the stem frame (FIG. 31B).
- Place a sleeve 2900 around the anchors 2700 (FIG. 31E).

In one embodiment of the invention, the deflated balloon anchor 4028 is placed within a slotted needle 4000 as shown in FIG. 32C. A pushrod 4012, with a tip 4036 larger in diameter than the shaft of the pushrod 4012, is also placed within the needle 4000 behind the balloon anchor 4028 and the needle 4000 is then retracted until the deflated balloon 4028 is delivered through the tip of the needle 4000 and subsequently inflated. The needle 4000 also includes a step 4032 at its proximal end for depth control.

Mechanical Cuff-Link Soft Tissue Anchors

Aspects of the present invention disclose a mechanical cuff-link anchor which is a dual-ended flip-style anchor attachment structure which can be transmurally deployed to soft-tissue via a small orifice, such as a delivery needle. The anchor is banana-shaped with an elliptical cross-section. The large surface area of the anchor interfacing with soft-tissue surfaces results in decreased stress concentrations. The rounded edges and curved profiles of the anchor also decrease stress concentrations. Decreasing stress concentrations prevents pressure necrosis and ischemia which result in anchor pull-out and failure. Thus, the anchor embodiments of the present invention provide strong, long-term attachment. In one embodiment, the anchor is a fixed length anchor such that over-tensioning that leads to pressure necrosis is prevented. The anchor length may be adjusted, in other embodiments, to accommodate tissue thicknesses up to 25 mm. The small size of the anchor permits delivery through a flexible endoscope. The anchor also includes a pinned connection between the strut and external anchor which allows the anchor and strut to be delivered via a needle and then deployed on the external soft-tissue surface. Because no sutures are required in deployment the long-term embrittlement and fracture issues associated with sutures are avoided.

Figure 33:
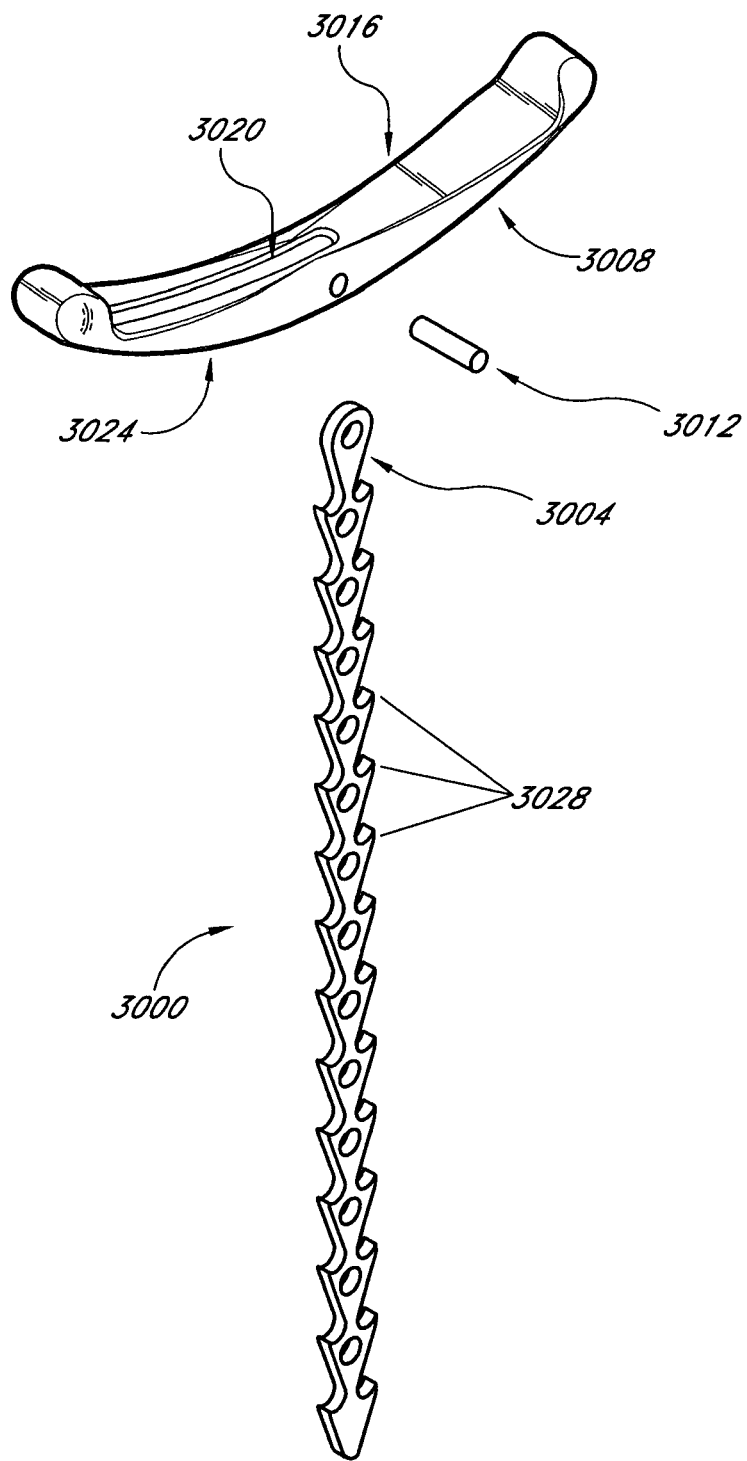
FIG. 33 illustrates a mechanical cuff-link anchor assembly.

As depicted in FIG. 33, a preferred embodiment 3000 of the invention comprises an external curved, banana-shaped anchor 3016 about 10 mm long by about 1.5 mm wide and 1 mm tall, with an elliptical cross-section for a high surface area to delivery needle diameter ratio. In this embodiment 3000, the anchor 3008 is comprised of high-strength, flexible material such as PEEK. The anchor 3008 may also have a slot 3020 through half of its length to receive a connection strut 3004. The anchor 3008 can be delivered as shown in FIGS. 32A-32B via a small delivery needle 4000 from the internal surface to the external surface of the soft-tissue. After being delivered, the anchor 3008 flips to resist pull-out. A connection strut 3004 with slot or teeth features 3028 to engage the internal anchor 3024 is rotatably pinned to the banana-shaped anchor 3016. The strut 3004 is also delivered via the delivery needle 4000 of FIGS. 32A-32B. The internal anchor 3024 of this embodiment may be comprised of components, such as pins 3012 that elastically flex to engage the teeth 3028 of the connection strut 3004, that enable a quick and secure connection to the connection strut 3004, such that the installed anchor 3000 is effectively a one-piece assembly.

Alternate embodiments of the anchor include:

a monolithic external anchor and strut with a living hinge about which to rotate the anchor and that connects quickly and securely to the internal anchor, an internal anchor that includes a mount ring or feature that may be utilized to connect the device being anchored in soft-tissue, a connection strut that also includes a mount ring or feature that may be utilized to connect to the device being anchored in soft-tissue, an internal anchor that is a monolithic anchor that can elastically deform to accommodate the strut engagement features; and a fixed length connection strut between 2 mm and 25 mm in length which positions the internal anchor at the pre-defined distance away from the external anchor.

In one embodiment, delivery of the mechanical cuff-link anchor is achieved with the aid of a pushrod 4012 shown in FIG. 32A. The push rod 4012 is advanced within the delivery needle 4000 behind the anchor 4004 such that the anchor 4004 is pushed to the tip of needle 4000 and is delivered through the slot 4020 at the tip of the needle 4000. In this embodiment, the strut 4008 remains outside of the needle 4000 and only the anchor or T-tag component 4004 is advanced by the push rod 4012 within the needle 4000.

In another embodiment, a pushrod 4012 has a well 4024 that bypasses the strut component 4008 of the mechanical cuff-link anchor such that pushrod 4012 pushes only the anchor or T-tag component 4004 as shown in FIG. 32B. In this embodiment, the entire mechanical cuff-link anchor, including the strut 4008 and T-tag 4004, are within the delivery needle 4000. The pushrod 4012 is then advanced within the needle 4000 such that the well 4024 is advanced over the strut 4008 and the pushrod 4012 pushes the T-tag component 4004 until it is delivered through the slot 4020 at the tip of the needle 4000.

FIG. 34 shows a Molly anchor or radially expandable anchor embodiment 2000, with a suture 2012 extending behind anchor 2000, deployed within a delivery needle 2004. A hollow pushrod 2008 advances behind the anchor 2000 and pushes the anchor 2000 out of the tip of the needle 2004. Once the anchor 2000 exits the needle 2004 it expands and locks into configuration. The expansion of the Molly anchor may be either passive or active, depending on the preferences of the surgeon or clinical requirements. A passive expansion would be one in which the anchor is pre-formed into its expanded state and returns to the expanded state when deployed from the needle. An active expansion would be one in which the surgeon applies a force, such as a tensile force, to expand the anchor to an expanded state. The anchor may be locked in this expanded state through plastic deformation of the bent ribs or through locking elements such that it does not return to the retracted state.

Figure 35:
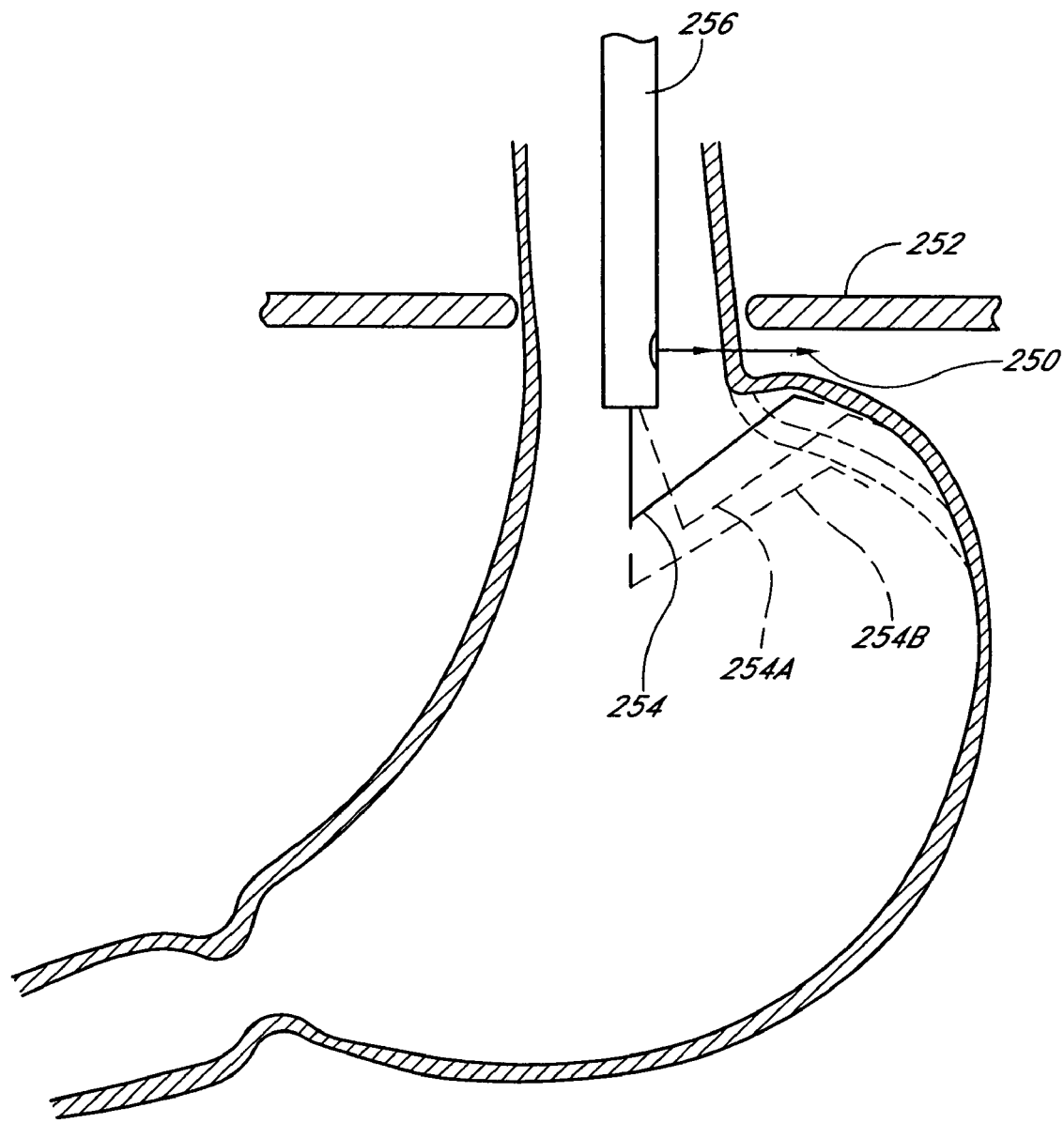
FIG. 35 illustrates a method and apparatus for placing T-tag fasteners at the gastroesophageal junction (GEJ).

When placing T-tag fasteners or other fasteners in the region of the GEJ, it is important to avoid other anatomical structures in the vicinity of the stomach and esophagus. One method for this is to create a safe space behind the GEJ for deploying the fasteners. One method to accomplish this is described in the parent application Ser. No. 10/698,148. Alternatively, one can take advantage of the fact that the proximal stomach generally lies just below the diaphragm when the patient is in a head-up position. Space will be created between the stomach and diaphragm into which transmural fasteners can be safely placed. This safe space can be increased by having the patient inhale deeply while in a head-up position to push the stomach down with the diaphragm, then exhale to lift the diaphragm up off of the stomach. Preferably, the fasteners 250 will be delivered parallel to the diaphragm 252, as shown in FIG. 35, though other orientations are possible. FIG. 35 also shows an optional stomach traction device 254 deployed through the working channel of an endoscope 256 that helps to facilitate safe deployment of the fasteners 250 in the GEJ region. The traction device 254 can be used to retract the gastric wall laterally 254A and/or distally 254B to create a safe place for deployment of the fasteners 250. Due to anatomic variations and pathology, the position of the diaphragm relative to the stomach and GEJ should be confirmed prior to using this technique.

Alternatively or in addition, pneumoperitoneum can be used to create a safe space around the stomach and esophagus. Pneumoperitoneal pressure will tend to collapse the stomach away from other surrounding organs and would be balanced by the pressure used to endoscopically insufflate the stomach for improved visualization and access.

Other tactics to avoid other anatomical structures in the vicinity of the stomach and esophagus include the use of imaging techniques such as fluoroscopy, esophageal ultrasound imaging, external ultrasound imaging and/or Doppler imaging when placing fasteners. Alternatively or in addition an "endoscopic compass" can be used to provide a reference for orienting the endoscope when using fastening devices. A small magnetized needle (i.e. a compass needle) is placed near the distal end of the endoscope where it can be viewed by the operator through the endoscope. A magnet is placed on the patient to provide a reference point for the compass, for example the reference magnet can be placed on the patient's back directly over the spine. The compass needle will point toward the reference magnet on the spine. Using the compass needle as a reference, the operator will be able to avoid inadvertently puncturing the aorta, which lies directly posterior to the esophagus.

The concept of the Veress needle can be adapted for avoiding puncturing other anatomical structures in the vicinity of the stomach and esophagus during endoscopic attachment of devices near the GEJ. A Veress needle is a needle equipped with a spring-loaded obturator that is often used for insufflation of the abdomen in laparoscopic surgery. A long, flexible device with a needle at the distal end and a spring-loaded obturator within the needle would be used to safely puncture the gastric or esophageal wall. Once the needle has passed through the wall, the spring-loaded obturator advances automatically to avoid damage to any surrounding tissues. A delivery cannula can be advanced over the needle and the needle can be exchanged with a fastener delivery device. Alternatively, this concept can be adapted directly into the fastener delivery device. A T-tag fastener or the like would be spring-loaded into the lumen of a delivery cannula so that it would be ejected out of the lumen immediately after the cannula has traversed the gastric or esophageal wall.

Another method for avoiding deploying fasteners into the aorta would involve a small diameter needle with a flow detector (e.g. a Doppler flow sensor) or pressure detector for detecting blood flow or blood pressure. Alternatively, a flow detector or pressure detector can be mounted on a separate guidewire inserted through the needle. The flow detector can be used to detect blood flow before the wall of the aorta is punctured. Alternatively, if backflow of blood or blood pressure is detected, indicating that the needle has punctured the aorta, the needle will be withdrawn and a fastener will not be delivered at that site. The small diameter puncture in the aorta should heal without complications.

Alternatively or in addition, the organs and other anatomical structures in the vicinity of the stomach and esophagus can be protected during endoscopic attachment techniques by using a depth stop on the needle or delivery cannula to prevent it from penetrating farther than necessary to traverse the gastric or esophageal wall. Examples of fastener delivery devices with a depth stop to protect nearby organs and structures are described in U.S. provisional patent application 60/569,442.

One method for placing an implantable device within a patient's body has been described as a "parachuting" technique. In this technique, multiple elongated sutures are sewn through the tissue where the device is to be implanted with the ends of the sutures extending out of the patient's body. The ends of the sutures are passed through a sewing ring or similar structure on the device while the device is still outside of the patient's body, then the device is parachuted or slid into place along the sutures. The device is typically secured in place by knotting the elongated sutures with the help of a knot pusher or similar device and then the sutures are cut off close to the knots. U.S. provisional patent application 60/534,056 describes a variation of this method for implanting a device within a patient's digestive tract using T-tag fasteners. Alternatively, suture locks such as those described in U.S. Pat. No. 4,235,238 or those used in the BARD Endocinch system can be used to secure the suture prior to cutting.

When parachuted into place along the sutures, the device may be folded or compressed to pass through the esophagus or through a delivery tube placed in the esophagus. When using this parachuting technique it is desirable to minimize the friction between the device and the sutures. This can be done by using a low friction material or a low friction coating on the sutures and/or the device. This is also done by dimensioning and/or orienting structures, e.g. holes, to guide the parachuted device to reduce friction.

Figure 36:
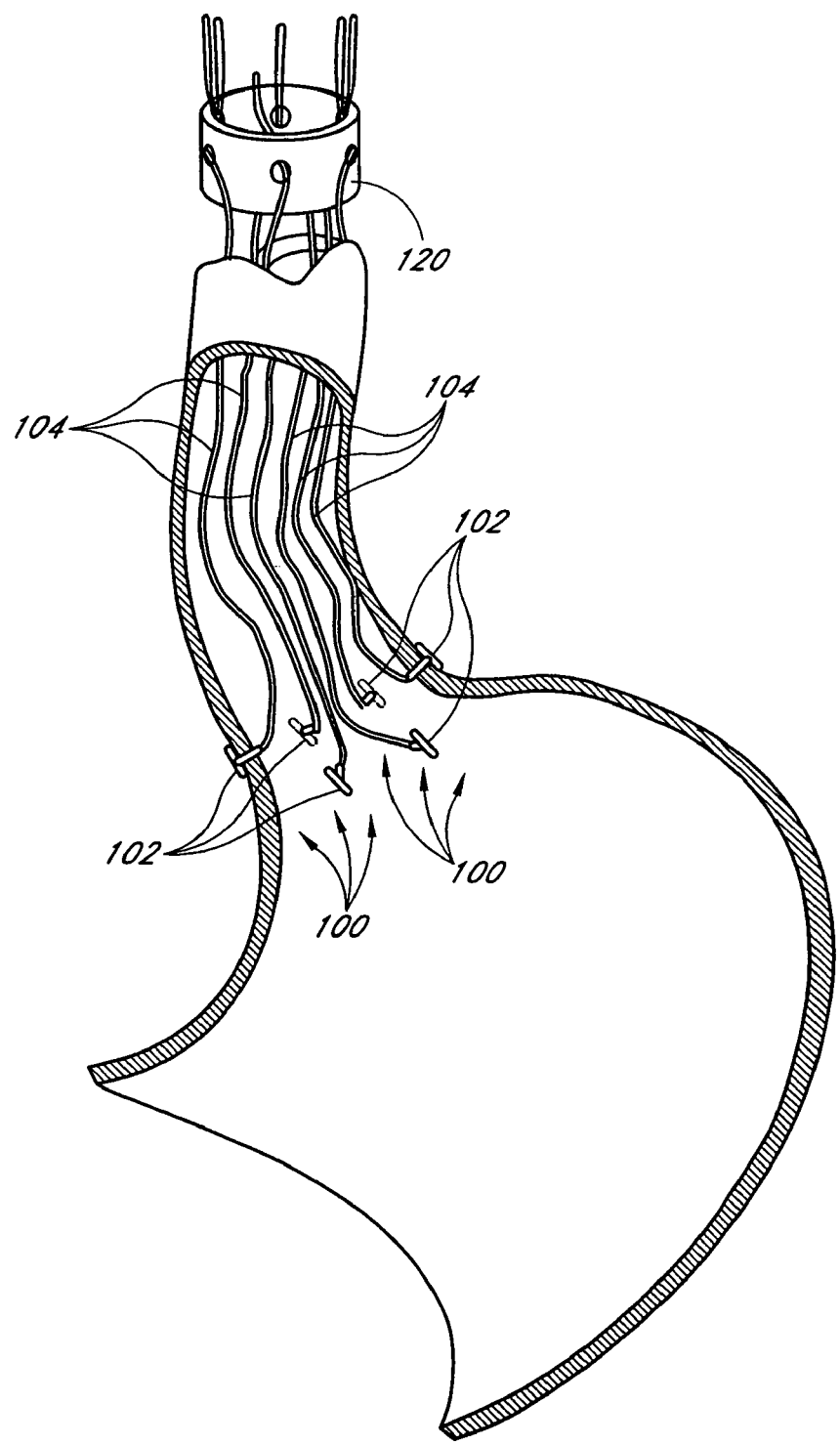
FIG. 36 shows a device being parachuted into place along a plurality of suture tails.

FIG. 36 shows an implantable device 120 being implanted at the GEJ using a parachuting technique. One method of using a fastener delivery device 150 for placement of an implantable device 120 by the parachuting technique is disclosed in U.S. utility patent application Ser. No. 11/025,364, previously incorporated by reference herein.

Alternatively, the device 120 may be partially parachuted into place, meaning that 2-4 parachute sutures are used to slide the device 120 into position with the proper orientation. Then additional fasteners, for example T-tag fasteners, are delivered to complete the attachment of the device 120 to the tissue.

If suture tails are delivered through a closed lumen (e.g. in or attached to an endoscope), the lumen must be removed from around the suture tails before a device can be parachuted over the sutures if the device is too large to pass through the lumen. This can present a challenge related to maintaining the organization of the suture tails and preventing contusion, crossing, winding and/or tangling of the suture tails. If T-tag fasteners and their suture tails are passed externally e.g. through an external lumen with a longitudinal slot or in a non-enclosed rail type system, the suture tails can be managed external to the lumen used to place the T-tag fasteners and external to the scope. This facilitates manipulation of the scope, simplifies scope exchanges and simplifies suture tail management.

Suture tail management external to the scope or an enclosed lumen can be combined with suture holders external to the patient, similar to those used for parachuting replacement heart valves into place. Snugging the sutures as described above is simpler when the suture tails are external to the scope, as is avoidance of crossing, winding and/or tangling of the suture tails. Suture holders, such as slots, clamps or clips, can be combined with a mouth guard for organizing the sutures during a peroral parachuting procedure.

One aspect of suture tail management is that it must happen from one end of the system to the other. Therefore, the method and apparatus must address this issue. For example, after placement of a T-tag fastener, a slight tension on the suture tail can hold the suture against the wall of the lumen or in a straight position where it is less likely to tangle. Apparatus can include means to maintain tension while allowing scope movement and manipulation, e.g. tension from a long soft spring, an elastic band or a spring-loaded reel.

Sometimes, when performing an endoscopic procedure, an overtube is used to line the esophagus and protect it from damage due to insertion and manipulation of the endoscope and related tools and devices. Other practitioners prefer to avoid the use of an overtube. In either case, it may be desirable to secure an implant being parachuted down the esophagus in a collapsed, folded or otherwise reduced configuration. A major issue when parachuting a device into place is friction between the device and the sutures, and collapsing or folding the device may exacerbate the problems with friction.

The following method is intended to reduce the problems with friction between the device and the sutures when parachuting a device through the esophagus. The method allows the device to be parachuted through the esophagus in a folded configuration, while it also allows the sutures to pass through the device while it is in an unfolded position. In addition, the method allows the sutures to be pulled through the device one at a time, which further reduces the problems with friction. This method can be used, for example, with the t-tag and/or t-tag delivery systems described herein.

1) Place fasteners (e.g. 6-10) in or through gastric wall with suture tails extending out through the patient's mouth; the sutures should have a length that is about 100-140 cm longer than required to exit the mouth;

2) thread suture tails through the device to be parachuted into place, e.g. an implant mounting ring;

3) slide the device down the sutures until it is just outside of the patient's mouth, with 100-140 cm of suture extending beyond the device;

4) fold or collapse the device and secure it in the collapsed position, e.g. with a removable sack or tied with a suture;

5) slide the device through the esophagus or the scope overtube (the device is not slid down the sutures, but instead the sutures are allowed to move with the device into the esophagus with the ends of the sutures remaining outside the patient);

6) once the device is through the esophagus and inside the patient's stomach, the device is release from its collapse position, and any restraining device that was used is removed perorally;

7) while controlling the device (e.g. with a grasper), and preferably under direct vision, pull each suture through the device until all the slack is removed and the device is at or near its intended position in the stomach;

8) position and secure the device in its intended position in the stomach.

FIGS. 37A-37G illustrate a dual-headed T-tag fastener 100 that is especially adapted for attaching devices that are parachuted into place within a patient's digestive tract. Alternatively, the dual-headed T-tag fastener 100 can also be used to attach cuffs, bypass tubes or other devices that are not parachuted into place as well as attaching tissue to tissue. The T-tag fastener 100, which is shown being deployed in FIG.

37G, has a primary T member 102 that is pivotally attached near its center to the end of an elongated suture 104. The primary T member 102 has an undeployed position wherein the primary T member 102 is approximately parallel to the body of the elongated suture 104 and a deployed position wherein the primary T member 102 is approximately perpendicular to the body of the elongated suture 104. A secondary T member 106 is pivotally attached near its center to the body of the elongated suture 104 at a position spaced apart from the primary T member 102. The secondary T member 106 has an undeployed position wherein the secondary T member 106 is approximately parallel to the body of the elongated suture 104 so that it presents a low profile so that a device can be slid in place along the elongated suture 104 and over the secondary T member 106 and a deployed position wherein the secondary T member 106 is approximately perpendicular to the body of the elongated suture 104. The fastening gap, that is distance between the primary T member 102 and the secondary T member 106, may be fixed or, optionally, the secondary T member 106 may be slidable along the body of the elongated suture 104 to adjust the fastening gap.

FIGS. 37A-37F are detail drawings of the secondary T member 106 of the T-tag fastener 100 of FIG. 37G. FIGS. 37A-37B show two variations of the secondary T member 106 alone. FIG. 37C-37E show three variations of the secondary T member 106 in the undeployed position wherein the secondary T member 106 is approximately parallel to the body of the elongated suture 104 so that it presents a low profile so that a device can be slid in place along the elongated suture 104 and over the secondary T member 106. Various securing members, including a stopper member 107 (FIG. 37D), knot 109 (FIG. 37C), crimp 111 (FIG. 37E) are shown. FIG. 37F shows the secondary T member 106 in the deployed position wherein the secondary T member 106 is approximately perpendicular to the body of the elongated suture 104. In the embodiment shown, the secondary T member 106 is preferably constructed from a polymer, a rigid tubular material, for example NiTi, Ti or stainless steel tubing. A first end 108 of the secondary T member 106 is tubular in configuration and the body of the elongated suture 104 passes through the lumen 112 of the tube. A second end 110 of the secondary T member 106 is cut away around approximately 60-180 degrees of its perimeter along one side to allow the secondary T member 106 to pivot or swivel relative to the body of the elongated suture 104 as shown in FIG. 37F. The secondary T member 106 is pivotally attached to the body of the elongated suture 104, for example by a stopper structure, a knot in the suture 104, crimping, adhesive or other attachment means. Attachment of the T member 106 to the suture will optionally prevent motion of the T member in either direction. Restriction of motion in the proximal direction will enable the T member to function to hold a structure in place, as shown in FIG. 37G, while restriction of motion in the distal direction will facilitate passage of the T member 106 through a structure as shown in FIG. 37G.

Figure 39:
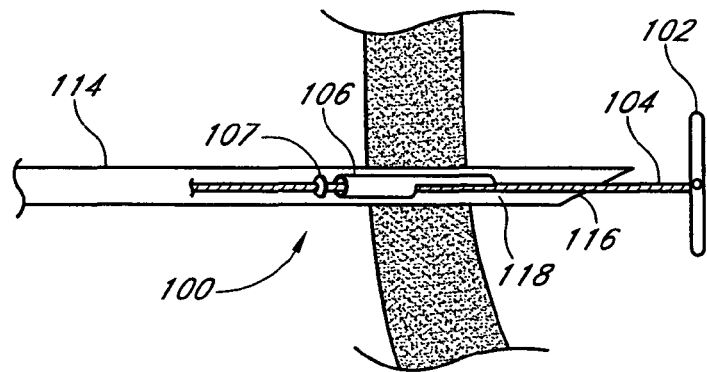

In some embodiments, a stopper member 107, or other securing means such as an adhesive, crimp or knot may be used alone or in combination to create a tapered or gradual proximal transition, which may facilitate passage of the secondary T member 106 through other structures as shown in FIG. 39. Optionally, the secondary T member 106 may be slidable along the body of the elongated suture 104 in order to adjust the fastening distance. In this case, a secondary securing means would be applied to the T member 106 once it is in place. This could be a knot, crimp, adhesive, stopper member 107, or other securing means known in the art. In some embodiments more than one stopper will be appropriate, e.g. one to prevent distal motion and one to prevent proximal motion.

Figure 38:
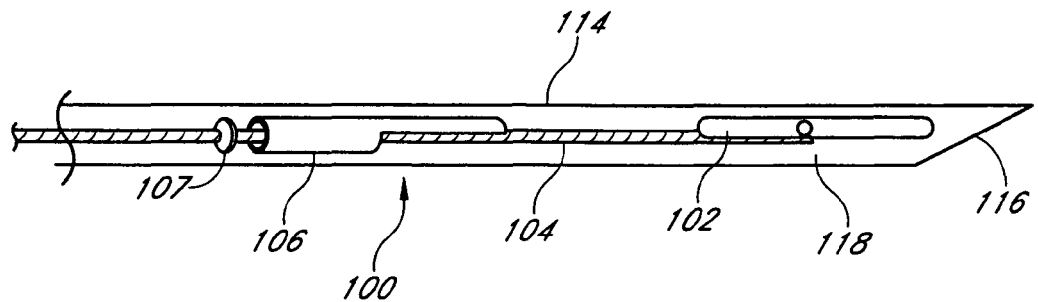
FIGS. 38-43 show the steps for deploying a dual-headed T-tag fastener.

FIGS. 38-43 show the steps for deploying a dual-headed T-tag fastener 100 of the type shown in FIGS. 37A-37G. FIG. 38 shows the T-tag fastener 100 positioned within the lumen 118 of a delivery cannula 114 with the primary T member 102 and secondary T member 106 in the undeployed position. The elongated suture 104 extends through the lumen 118 and out the proximal end of the delivery cannula 114. The delivery cannula 114 can be part of a fastener delivery device, which is explained in more detail below. The delivery cannula 114 has a sharpened distal end 116 that is used to penetrate the tissue that is to be fastened, for example the gastric or esophageal wall in the vicinity of the GEJ. The primary T member 102 is ejected from the delivery cannula 114 and deployed behind the tissue.

FIG. 39 shows the T-tag fastener 100 with the primary T member 102 deployed. The delivery cannula 114 is removed by withdrawing it with the enclosed secondary T member 106 through the tissue and then further withdrawing the cannula 114 from the proximal end of the suture 104. Then the primary T member 102 is snugged against the tissue with a little tension on the suture 104 in preparation for parachuting or otherwise attaching a device into place. Alternatively, the delivery cannula 114 can be passed through two or more layers of tissue, two or more devices or a combination of layers of device and tissue to achieve the configuration similar to that shown in FIG. 41.

Figure 40:
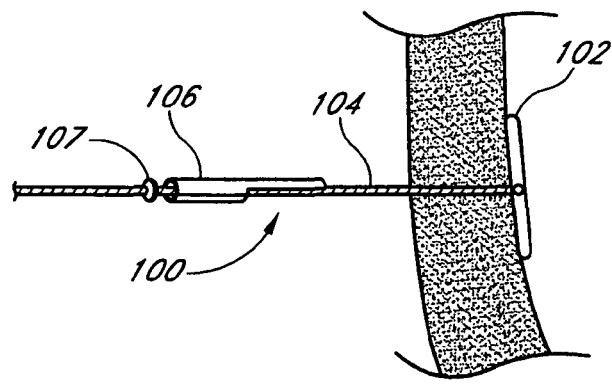

FIG. 40 shows the T-tag fastener 100 after the delivery cannula 114 has been removed. After a sufficient number of fasteners have been placed in the tissue, the device to be implanted can be parachuted or otherwise deployed into place by passing the sutures 104 through the device and sliding the device down the sutures 104 until it is in contact with the tissue. The device is slid over the secondary T member 106, which is still in its undeployed position.

Figure 41:
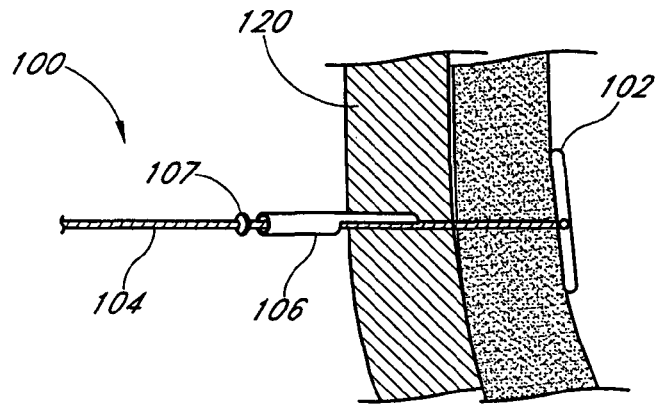
Figure 42:
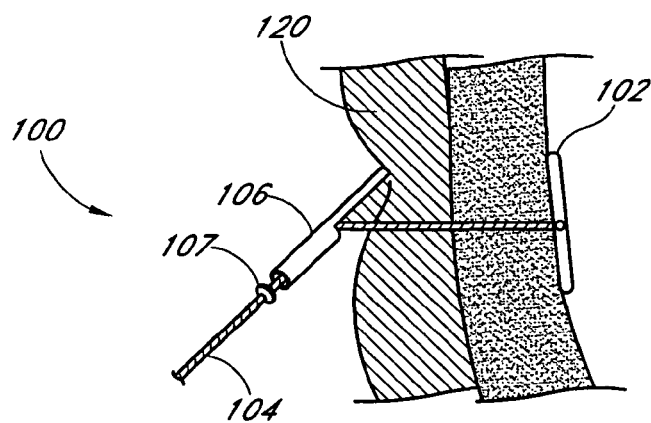
Figure 43:
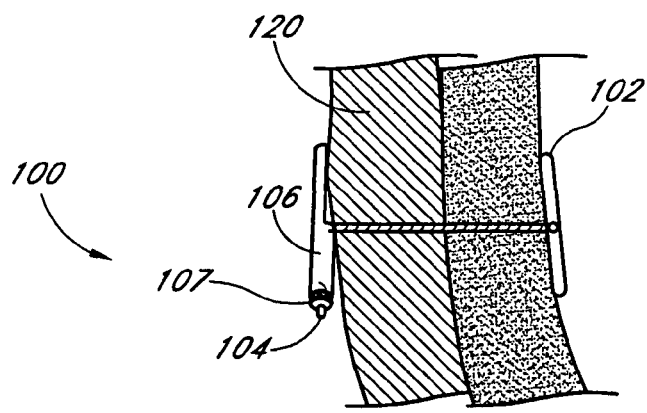
Figure 44A:
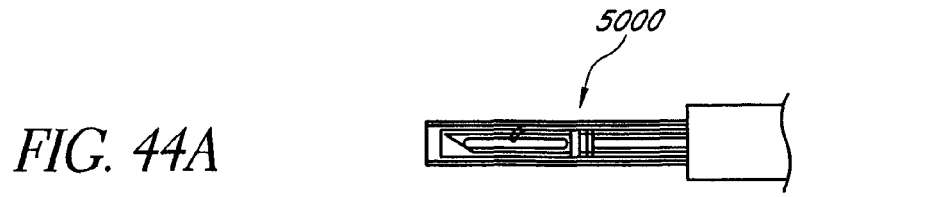
FIG. 44A-44E shows a sewing method of delivering a T-tag.
Figure 44B:
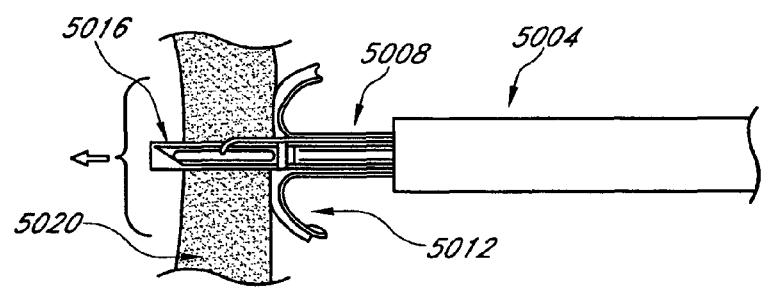
Figure 44C:
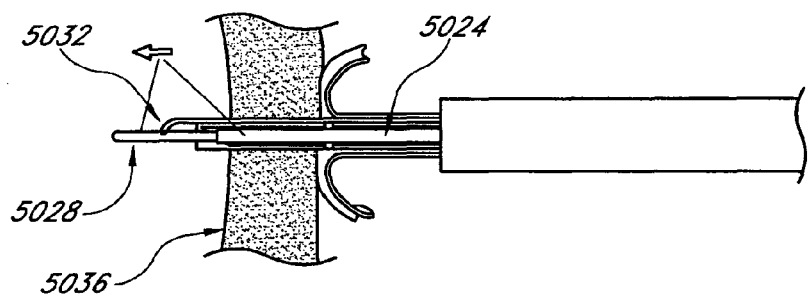
Figure 44D:
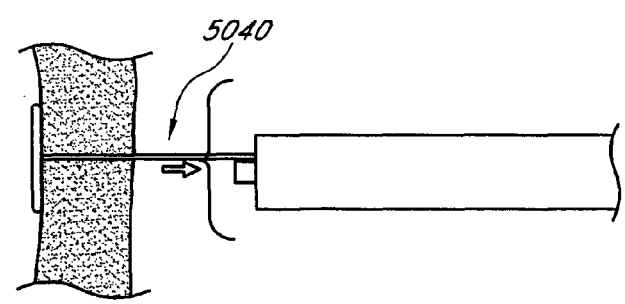
Figure 44E:
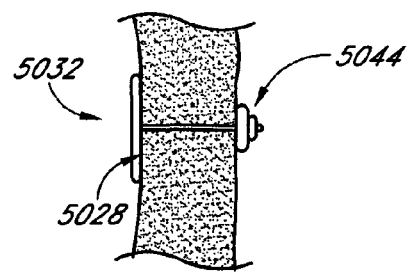

FIG. 41 shows the T-tag fastener 100 after a device has been deployed, for example by being parachuted into place. Tension is applied to the elongated suture 104 (and, optionally, a pushing force is applied to the device) to provide clearance for the secondary T member 106 to rotate or swivel to the deployed position. FIG. 42 shows the T-tag fastener 100 with the secondary T member 106 being deployed. The tension of the suture 104 is released to allow the secondary T member 106 to fully deploy and the suture 104 is trimmed proximal to the secondary T member 106. FIG. 43 shows the T-tag fastener 100 fully deployed. Optionally, a lateral force may be applied to the secondary T member 106 to assist deployment.

The fastening gap determines the tension on the suture 104 and hence the pressure on the tissue exerted by the primary T member 102 and the implanted device 120. Optionally, this gap can be variable and or changeable as described herein.

Other configurations of fasteners and fastener delivery devices known in the art can be used in conjunction with the present invention. For example, U.S. Pat. No. 4,235,238 describes various fasteners and endoscopic fastener delivery devices for use in the gastrointestinal system. Other attachment and/or parachuting approaches can be used with these dual t-tag fasteners to secure devices, for example, to plications.

Another method for deploying a T-tag is shown in FIG. 44A-44E and is referred to herein as the Sewing Method.

By way of example, the sewing method is described below using the embodiment of the sewing device shown in FIGS. 44A-44E.

Method Steps:

The flexible endoscope 5004 is maneuvered to the target tissue.

The needle catheter 5008 is advanced through the biopsy channel of the scope 5004.

The split protective needle sheath 5012 opens as the needle 5016 emerges from the tip of the scope 5004.

The needle 5016 is plunged into the gastric tissue 5020 to a depth of 2-3 mm, with the open protective needle sheath 5012 acting as a stop to control the depth of needle 5016 penetration.

The pusher 5024 is advanced to eject the T member 5028 of the T-tag fastener 5032 from the distal end of the needle 5016 just beyond the serosal surface 5036.

The needle catheter 5008 is withdrawn into the biopsy channel of the scope 5004 and the split protective needle sheath 5012 closes.

The suture 5040 is secured by tying or by pushing a suture lock 5044 onto the suture 5040.

Optionally, the device may be configured to perform the sewing, locking and cutting of the suture in a single action. If the suture is passed through an open locking mechanism over the needle, the suture could be locked by pushing the catheter, sheath and lock forward.

Delivery cannula devices/systems (hereinafter delivery cannula) can be configured for the delivery of multiple T-tag or other fasteners. In particular these delivery cannulae allow placement of multiple T-tags (or in the case of a dual-headed T-tag fastener, primary T members) through a layer of tissue and/or a device while facilitating the management of multiple fastener suture tails.

A delivery cannula can include some or all of the following components, which will be described in more detail below in relation to specific embodiments of delivery cannulas:

penetrating cannula to penetrate the tissue and deliver the T member of the T-tag;

transit cannula to delivery the T-member of the T-tag to and into the proximal end of the penetrating cannula;

loading cannula to load or position the T member of the T-tag at and into the proximal end of the transit cannula;

garage or protective cannula to provide a shield into and out of which the penetrating cannula can be advanced and retracted when appropriate;

pusher to perform any or all of the functions related to advancing a T-tag through the loading cannula, through the transit cannula, through the penetrating cannula and expelling the T-tag out of the penetrating cannula.

In a basic delivery cannula embodiment, the first components are a single elongated hypodermic tube with a sharpened distal tip as the penetrating cannula and a wire or rod as the pusher. This type of device generally delivers a single fastener before being withdrawn to clear the suture tail from the tube. A more complicated delivery cannula is similar to the above, but incorporating a longitudinally slotted hypotube. This allows the tail/suture of the T-tag fastener to be external to the hypotube and allows a smaller diameter hypotube as well as other suture/tail handling advantages. In this case the above-mentioned penetrating, transit and loading cannulas are embodied in the single cannula.

In all the delivery cannulas, the penetrating cannula must be movable relative to the tissue through which it penetrates for T-tag fastener delivery. In a basic delivery cannula, the penetrating cannula will move in conjunction with the transit cannula and loading cannula. In more complex delivery cannulas, the penetrating cannula will move relative to the transit cannula and/or loading cannula.

The delivery cannula can be configured to be used:
1) within the biopsy channel of an endoscope;
2) attached to the exterior of an endoscope;
3) as a stand alone device with a separate means of aiming/visualization.

The delivery cannula should include means to keep the penetrating cannula point from inadvertently damaging tissue or the device through which it is delivered. For example, a Varess needle style obturator or other obturator can be used. The obturator must be removed to deliver the T-tag fastener through the lumen of the penetrating cannula. An external needle protector, or garage, may also be used, which has the advantage that it would not have to be removed for T-tag fastener delivery. A slotted garage could have additional advantages for T-tag fastener delivery. A penetrating cannula that is spring loaded within a garage where it only exits the garage under the impetus of a pusher in preparation to penetrating tissue would also have certain advantages.

Retracting the penetrating cannula into the biopsy or instrument channel of the endoscope will protect the tissue from inadvertent damage, but not the lining of the instrument channel. To protect the biopsy channel, the penetrating cannula could be retracted within the transit cannula or into a structure (garage) located at the juncture of the penetrating cannula and the transit cannula.

Figure 45A:
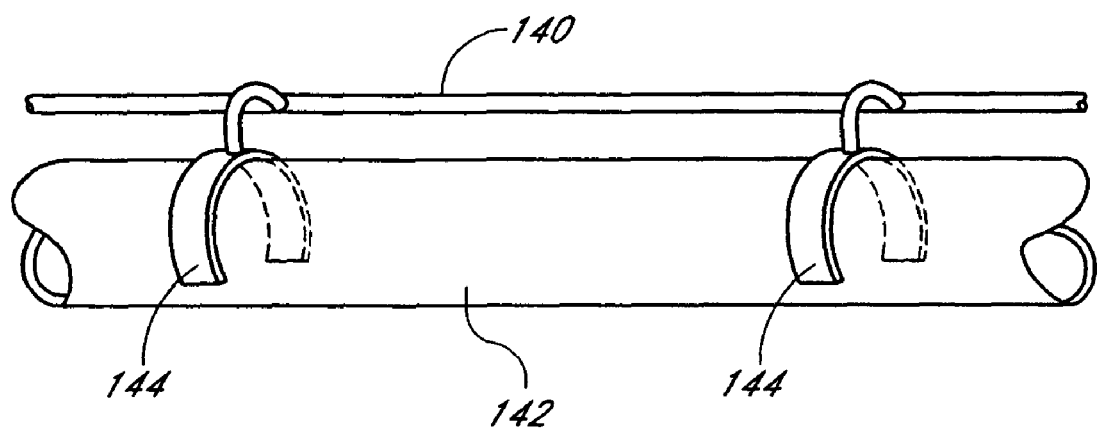
FIGS. 45A-45C show variations of a rail-mounted delivery device for deploying a T-tag fastener mounted on the exterior of a flexible endoscope.
Figure 45C:
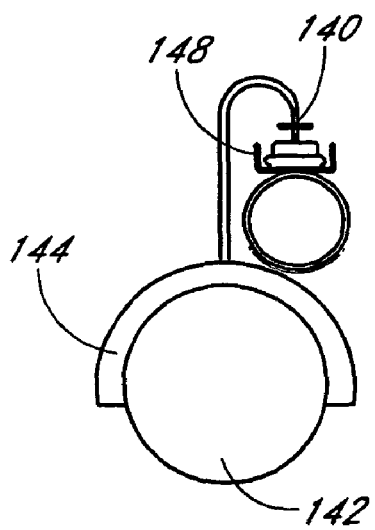
Figure 45B:
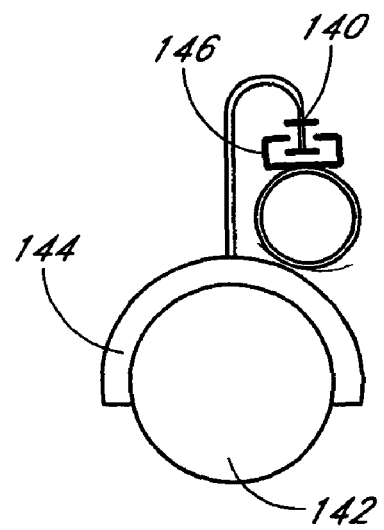

As an alternative to the slotted hypotube previously mentioned, a magnetic or mechanical rail system can be used in place of or in combination with the transit cannula. In this case, the pusher captures the primary T member 102 for delivery to the penetrating cannula. The pusher is magnetically or mechanically coupled to the transit cannula. FIGS. 45A-45C show possible configurations for a rail-mounted delivery device for deploying a T-tag fastener mounted on the exterior of a flexible endoscope. FIG. 45A shows a rail 140 mounted to the exterior of a flexible endoscope 142 using a plurality of mounting clamps 144. In one embodiment, the rail 140 may be configured as a slotted tube. Alternatively, the rail 140 of FIG. 45A could incorporate a mechanical coupling 146 as shown in FIG. 45B or magnetic coupling 148 as shown in FIG. 45C. A delivery cannula, such as described below, will be slidingly mounted to the rail 140 using one of the coupling mechanisms described.

Similarly, a smaller diameter, short length slotted hypotube transit cannula can be used with a monorail T capturing pusher as a means to transfer the T-tag fastener to the penetrating cannula. In this context "monorail" refers to a short distal coupling section such as those used to couple a monorail or rapid exchange catheter to a guidewire. In this case, the monorail transit cannula, such as shown in FIGS. 45B-45C, could be coupled to a rail 140 as in FIGS. 45A-45C. With this configuration, the transit cannula, rather than extending the full length of the delivery cannula, would be a short length and would move from a position at the distal end of the loading cannula to a position at the proximal end of the penetrating cannula. This short length transit cannula length could be approximately half to two or three times the length of the T member. The term monorail T capturing pusher refers to a pusher alone or in combination with the transit cannula.

Having elongated suture tails extending out of a patient's mouth (or other orifice) with an associated need to pass devices over the suture tails can be cumbersome if standard "exchange length" techniques are applied. A monorail style device could be used through an internal or external endoscope lumen or independent of the endoscope. This type of design allows control of the T member in a short slotted cannula while the majority of the length of the suture tail would be external to an elongated transit cannula. This may also provide an easier path for the long suture tail as when an elongated slotted cannula might not maintain a slot free of obstruction when the endoscope was subjected to flexion.

If the monorail portion of the device extends out of the lumen of the endoscope, the monorail portion can optionally be of sufficient length to partially remain within the endoscope lumen to provide improved support and manipulation capability.

A two-channel endoscope can be used to deploy a series of T-tag fasteners. In one method of using such a 2-channel endoscope the T-tag fasteners are delivered through the first channel of the scope. The distal T members of the fasteners, individually or collectively, are placed outside the distal end of the scope. A delivery device is placed in the second channel and positioned near the distal tip of the scope. A capture/pusher device is passed through the first delivery cannula and a single distal T member is captured and drawn into the delivery cannula. The penetrating cannula of the delivery device is preferably slotted. The delivery device is used to deploy a series of T-tag fasteners into the tissue in the manner described above. The steps of T member capture by the pusher, drawing into the delivery cannula and deployment are repeated for each T fastener. As the endoscope is removed from the patient, the multiple suture tails of the T-tag fasteners are drawn out of the distal end of the first channel of the endoscope. The suture tails should be long enough to extend out of the patient's body, for example out through the patient's mouth. Labeling, color-coding or other means may be used to help organize the suture tails. A device can be threaded onto the proximal ends of the sutures and parachuted into place. Optionally, the ends of the suture tails may have needles attached to facilitate passing the sutures through preformed holes or a sewing ring on the device.

Figure 46B:
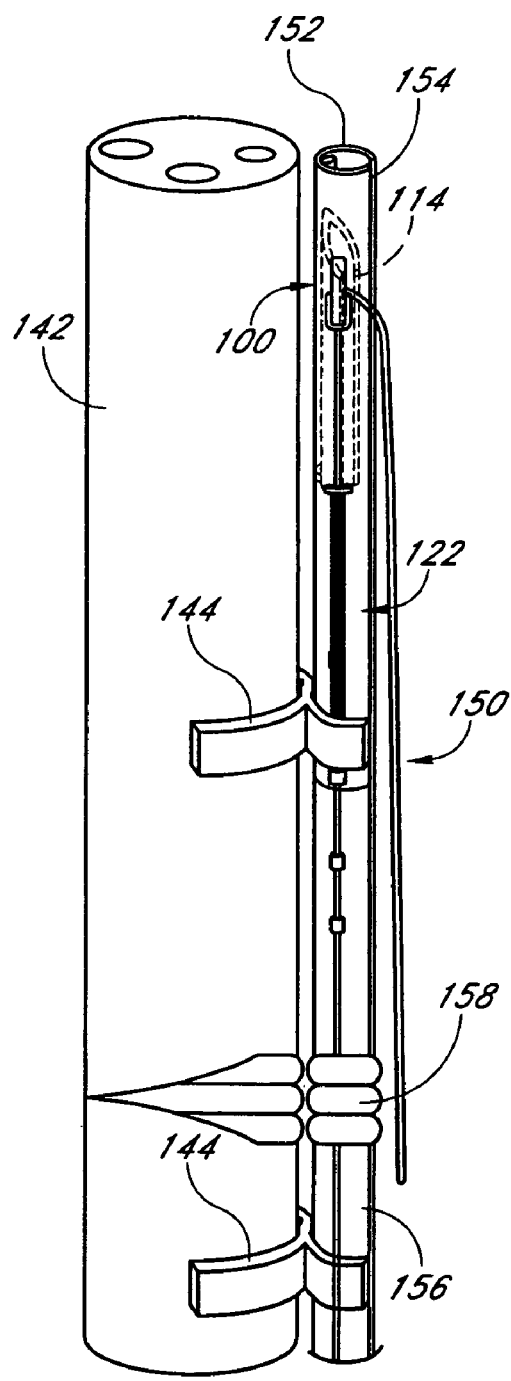
FIG. 46A-46B shows another embodiment of a delivery device for deploying a T-tag fastener mounted on the exterior of a flexible endoscope.
Figure 46A:
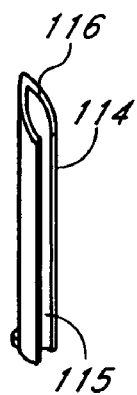

FIG. 46 show another embodiment of a delivery device 150 for deploying a T-tag fastener 100 mounted on the exterior of a flexible endoscope 142. FIG. 46 shows a penetrating cannula 114, which may be made of hypotube, 17-20 gauge, regular, thin or extra thin wall, 304 stainless steel or NiTi. The penetrating cannula 114 has a sharpened distal tip 116, which may be a short or standard hypodermic needle bevel, and a longitudinal slot 115, which is preferably 0.008-0.020 inch wide and around 0.5-1.5 inches in length.

A tubular member that functions as a garage or protective shield 152 for the penetrating cannula 114 may be mounted externally on the endoscope 142, e.g. with one or more interference fit mounting clips 144. The garage 152 has an ID larger than the penetrating cannula OD to allow sliding of the penetrating cannula 114 relative to the garage 152 with clearance and/or a slot 154 for the suture tail. The penetrating cannula 114 may be spring mounted in the garage 152, so that the penetrating cannula 114 retracts into garage 152 automatically or upon withdrawal from tissue.

The distal end of the transit cannula 156 connects to the proximal end of the garage 152. The garage 152 and the transit cannula 156 may be constructed of separate pieces of tubing as shown or, alternatively, they may be constructed of one continuous piece of tubing. The transit cannula 156 has a diameter the same or slightly larger than the penetrating cannula 114, optionally slotted, mounted externally on endoscope 142, e.g. with one or more interference fit mounting clips 144. In conjunction with the pusher 122, it delivers the T-tag fastener 100 to the penetrating cannula 114 while it is positioned in the garage 152. Preferably, it is designed to prevent binding when the endoscope 142 is deflected, including retroflexed, e.g. with a bellows or other flexible structure 158 at major flex points. The transit cannula 156 may be ferrous/magnetic for magnetic coupling between the transit cannula 156 and pusher 122. Alternatively, it could be a mechanical coupling or alternatively could use a monorail configuration.

A loading cannula or other fastener loading mechanism attaches to the scope biopsy port or scope handle. The loading cannula may load the pusher with T-tag fasteners individually or may feed T-tag fasteners from a magazine to pusher for delivery of multiple tags.

Figure 47:
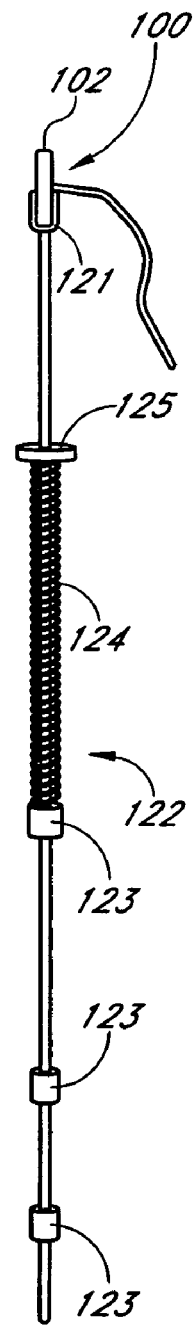
FIG. 47 is a detail drawing of a pusher for use with a T-tag fastener delivery device.

FIG. 47 is a detail drawing of a pusher 122 for use with a T-tag fastener delivery device 150. The pusher 122 sequentially advances the penetrating cannula 114, then deploys the T-tag fastener 100. The pusher 122 is preferably a stainless steel or NiTi wire, 0.008-0.025 inch diameter. Interface knobs 123 of diameter slightly smaller than the ID of transit cannula 156 are placed at intervals along the pusher 122 to allow free movement when the transit cannula 156 is flexed. Optionally, they can be magnets to assist coupling with the transit cannula. This embodiment shows a distal socket 121 to capture the T member of the T-tag fastener 100. In some embodiments a loose fit for easy release may be desired, while in others a press fit for retention and a secondary means to assist in release may be indicated. The distal socket 121 may have an optional slot for the suture tail. A spring loaded interface 125 engages the proximal end of the penetrating cannula 114 when the distal end of T-tag fastener 100 reaches the proximal end of the penetrating cannula bevel 116. The pusher 122 then advances the penetrating cannula 114 until it is fully extended and reaches a stop, the spring 124 then compresses and distal T member 102 is advanced out of penetrating cannula 114, pusher 122 is retracted leaving the T-tag fastener 100 attached to the tissue. The pusher 122 is then retracted and the penetrating cannula 114 then retracts. The pusher 122 may wind up onto a reel or drum attached to the loading cannula.

Figure 48:
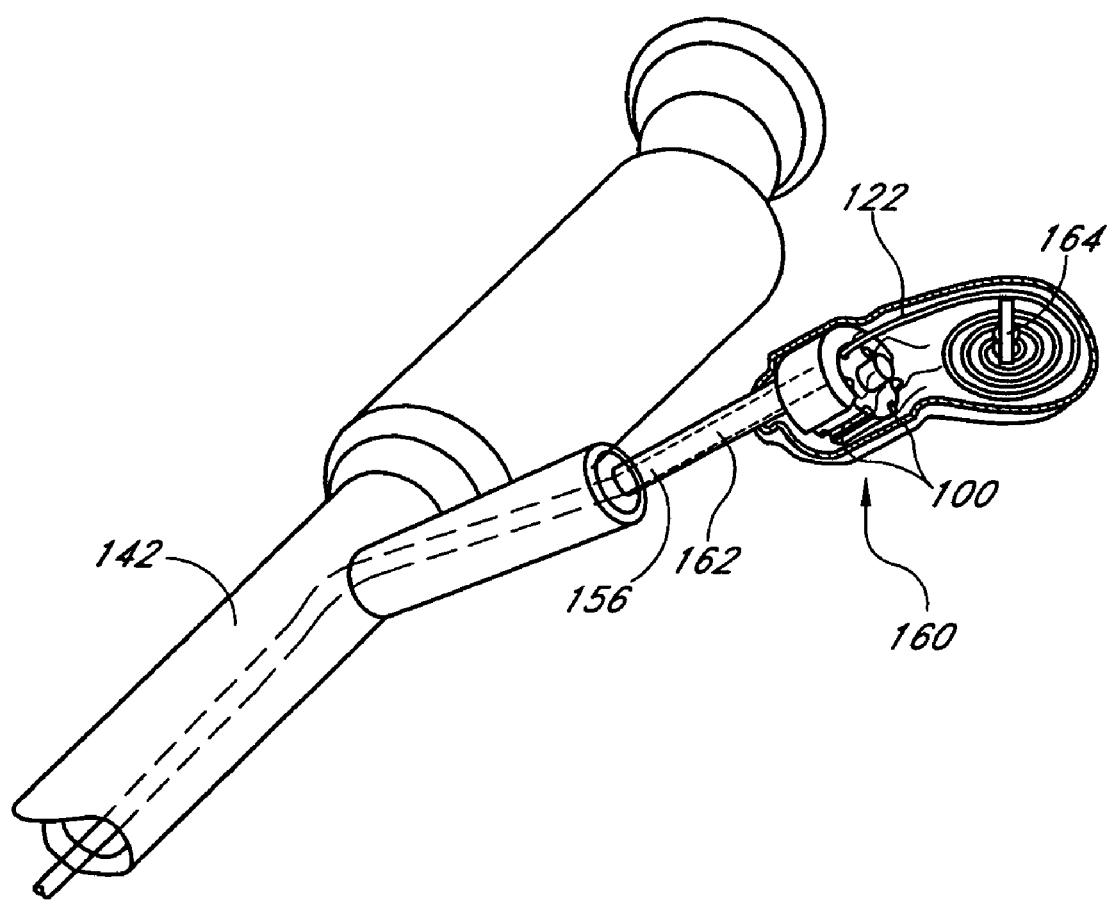
FIG. 48 shows a proximal end of a delivery device with a magazine for sequentially delivering multiple T-tag fasteners.

FIG. 48 shows a proximal end of a delivery device with a magazine 160 for sequentially delivering multiple T-tag fasteners 100. In this embodiment the transit cannula 156 passes through the biopsy channel of the endoscope 142. The proximal end of the transit cannula is near the biopsy port of the scope where a loading cannula 162 is attached with a rotating magazine 160 to feed T-tags 100 one at a time into the loading cannula 162. The loading cannula will have a slot to receive the T member and a coaxial narrower slot to allow passage of the suture tail of the T-tag. At the proximal end of the loading cannula 162 is shown a retractable pusher 122 configured to be coiled by a reel mechanism 164 to control pusher advancement and retraction. In this embodiment, the distal socket 121 on pusher 122 is retracted proximal to the magazine 160, the magazine is then rotated to position the next T-tag at the loading cannula 162 and then the pusher and attached socket are advanced.

The T-tag fastener delivery device could use any long tail T-tag fastener, including the dual headed T-tag fastener described herein and in the prior application.

Other aspects of T-tag fastener delivery devices 150 include:

1) ease of use related to exchange of devices;

2) management of the tails 104 of previously inserted T-tag fasteners 100.

If used through an endoscope lumen or external to the endoscope, the delivery cannula or its components would be flexible to accommodate the flexing and articulations of the endoscope. Flexibility can be provided, for example, by the following features singly or in combination, over the full length of the device/component or at selected locations:

1) flexible and/or elastic polymeric material (e.g. PU, PE, PEBAX);

2) a superelastic metal material (e.g. NiTi);

3) a coiled or braided material (e.g. 304 stainless steel with or without a polymer coating);

4) a radially slotted material (e.g. 304 SS or NiTi);

5) a bellows (e.g. 304 SS or NiTi).

Longitudinally slotted cannulas have advantages related to cannula sizing and also for delivering multiple T-tag fasteners. The suture tails of each T-tag fastener can exit the cannula through the slot after the fastener is deployed so that they will not damage or interfere with subsequently deployed fasteners. A parachute T-tag fastener or a snap T-tag fastener, described below, can have particular advantages in this regard.

Figure 49A:
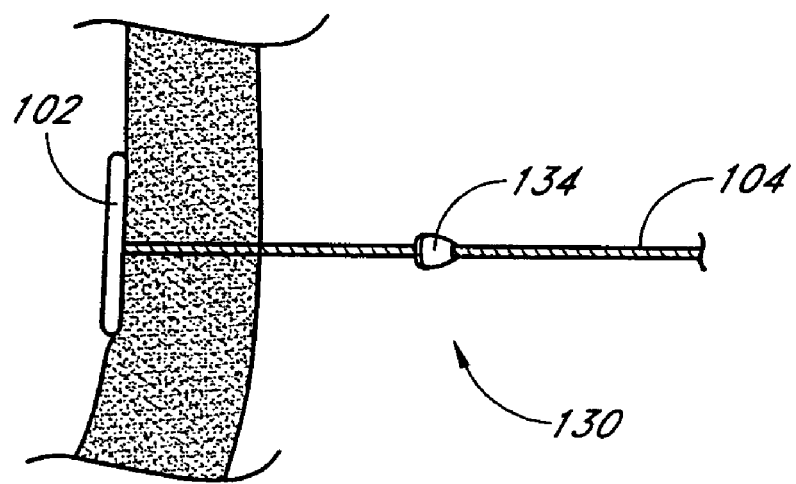
FIG. 49A shows a snap T-tag fastener.
Figure 49B:
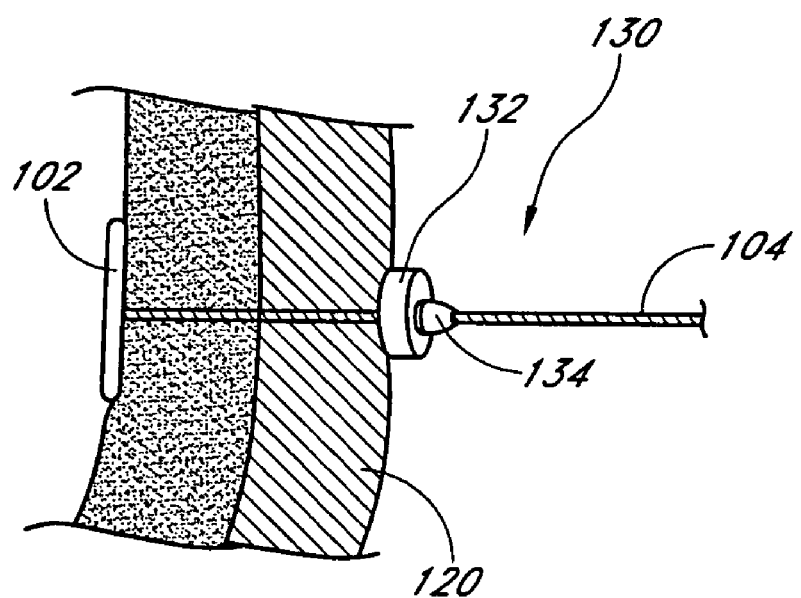
FIG. 49B shows the snap T-tag fastener of FIG. 49A with the cap in place.
Figure 50A:
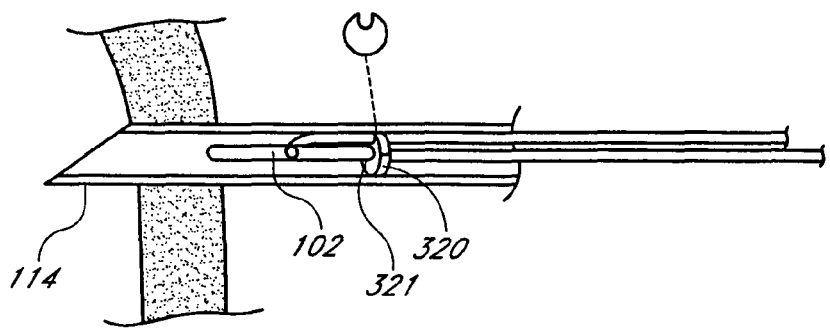
FIGS. 50A-50D show a method of T-tag fastener delivery with the suture tail inside of the penetrating cannula.
Figure 50B:
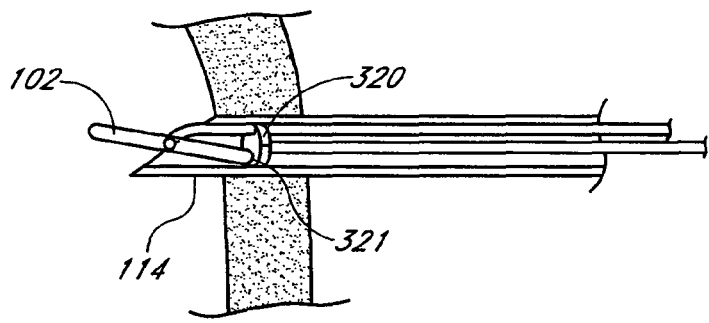
Figure 50C:
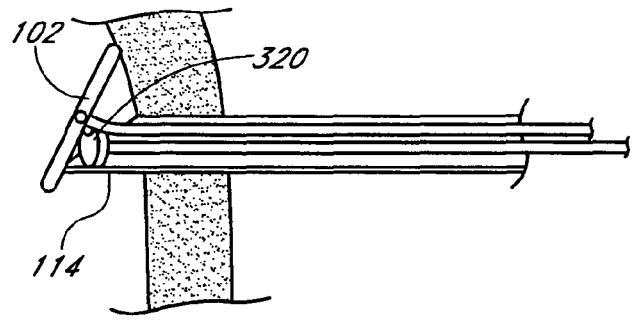
Figure 50D:
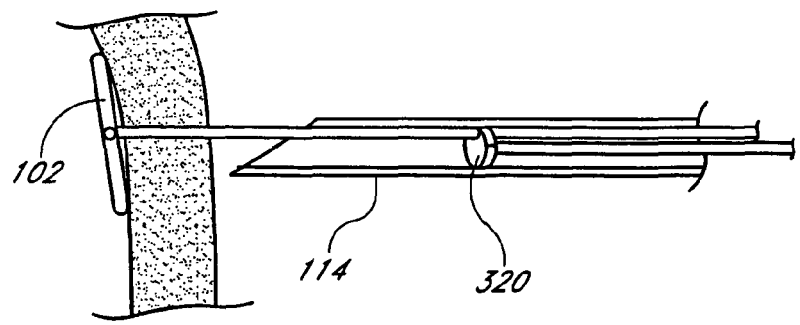

FIG. 49A shows a snap T-tag fastener 130 with a T member 102, a suture tail 104 attached to the T 102, and a snap member 134 attached to the suture tail 104. FIG. 49B shows the snap T-tag fastener 130 of FIG. 49A with the cap 132 in place. Materials and dimensions of the snap 134 and cap 132 are optimized for ease of snapping (i.e. pushing cap 132 over snap 134) while maintaining sufficient retention force with the fastener 130. Snap force should be less than 1 kg and preferably less than 200 gm. Retention force should be greater than the snap force and preferably greater than 2.0 kg. The cap 132 is not threaded onto the suture tail 104 until after the suture tail 104 has been threaded through the device 120 to be parachuted or otherwise deployed. The features and properties of the snap T-tag fastener 130 can be combined with the features and properties of other T-tag fasteners described herein.

One aspect in common between the parachute T-tag fastener 100 and the snap T-tag fastener 130 is the presence of a relatively large retention element (i.e. the proximal T member 106 or the snap 132) on the suture tail 104 in proximity to the distal T member 102. With appropriate dimensioning, the proximal T member 106 of a parachute T-tag fastener 100 or the snap 132 of a snap T-tag fastener 130 remains outside the slotted penetrating cannula 114 and facilitates positioning the suture 104 outside of the cannula 114, as shown in FIGS. 51B-51D. Use of a delivery cannula system where all components (penetrating cannula, transit cannula, loading cannula) are similarly slotted allows multiple T-tag fasteners to be placed without interfering with the suture tails of previously placed fasteners. Also, a rail system as described herein can be combined with a slotted penetrating cannula to accomplish a similar result.

The interface between the proximal end of the keyed wire 174, the T-tag fastener cartridge magazine and the pusher assembly 182 can all be combined in a deployment handle assembly similar to the one shown in FIG. 48, which could optionally deploy both the keyed wire and the pusher wire assembly, or the pusher wire assembly alone, from one or more reels. The deployment handle could be secured to the proximal end of an endoscope lumen or external to the endoscope control handle if the garage assembly is secured externally to the scope on its distal end. If through the endoscope lumen, the keyed wire would then be extended through the scope (optionally, before being placed into the patient.) The magazine could then be attached to the handle and a single cartridge advanced into a loading area where the pusher wire would be engage, then the cartridge and pusher wire, mated together, could be advanced onto the proximal end of the keyed wire.

In this embodiment, once the loading cannula and cartridge are mated, further advance of the mated cartridge and pusher rod would result in:

1) transit of the T-tag fastener in its cartridge to the distal end of the endoscope;

2) penetrating cannula extension;

3) holding and/or advancing the penetrating cannula when tissue is pierced (could be simultaneous with step (1)

4) holding penetrating cannula extended when T-tag fastener is deployed.

Retraction of the pusher rod would:

1) allow retraction of the penetrating cannula through the tissue;

2) pull the cartridge in a proximal direction to the proximal end of the endoscope (an interface e.g. mechanical or magnetic would be required);

3) position the cartridge for being expelled into a storage chamber.

When placing T-tag fasteners it can be beneficial to orient the T members in a specific direction relative to the anatomy. Two approaches are discussed:

1) orientation by delivery cannula;

2) orientation by pusher.

If a non-slotted penetrating cannula is used, then an oriented pusher or keyed cannula or keyed pusher and keyed T member can be used to control the orientation of the T member as it exits the delivery cannula. FIGS. 50A-50D show an example of a method of delivery orientation control that involves a keyed pusher 320 with a mating keyed portion 321 on the proximal end of the T member 102. In this case the pusher key 320 can also have a keyed delivery cannula 114 so the directional orientation is based upon the delivery cannula orientation. If the pusher 320 is not keyed to the delivery cannula 114, rotation of the pusher 320 may be sufficient to determine the directional orientation of the T member delivery. A lubricious coating on the pusher shaft may facilitate rotational control.

Use of a slotted delivery cannula with the suture tail of the T-tag fastener positioned through the slot can maintain orientation of the T member as it passes through the delivery cannula. This may be sufficient to orient the T member, but the suture tail will generally exit the slot before the T member is fully deployed. Keying the proximal portion of the T member to the slot can improved control of orientation during deployment.

FIGS. 50A-50D illustrate a simplified view of delivery of a T-tag fastener showing only the T member 102 of the T-tag fastener and the delivery cannula 114 with pusher 320 therein. In actual application, the entire delivery assembly would include an endoscopic delivery device (not shown), with the delivery cannula 114 deployed through the working channel of the endoscopic delivery channel. Also, in actual application the T-tag fastener would attach an attachment device such as a cuff to a gastrointestinal sleeve device through a grommet or hole in the cuff and/or sleeve device.

As shown in FIGS. 51A-51D, this can be accomplished by using a flattened portion 103 extending from the proximal end of the T member 102 that can serve as a key that engages the slot 115 and maintains the orientation of the T member 102 as it rotates during deployment. To deploy this T-tag fastener, it is helpful to apply tension to the suture tail 104 while slowly advancing the pusher 136 to cause the T member to rotate and lay against the tissue before the pusher 136 ejects the flat portion 103 from the delivery cannula. To help orient the T member 102, the pusher 136 can be configured with an interface knob head 138 having a slot 137 that engages the flat portion 103 of the T member 102 and holds it aligned with the slot 115 in the penetrating cannula 114.

Figure 51A:
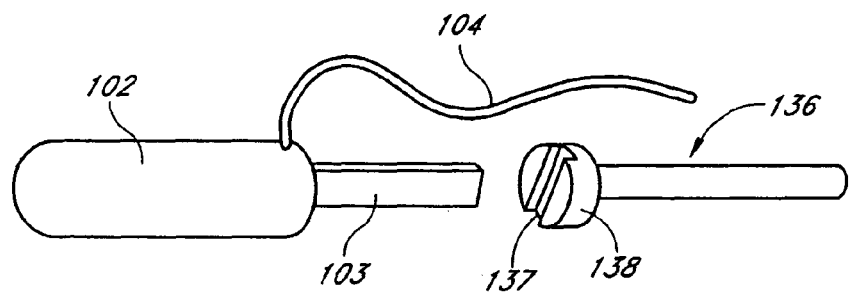
FIGS. 51A-51D show a slotted penetrating cannula with a pusher configured to exclude the suture tail of the T-tag fastener from the slot.
Figure 51B:
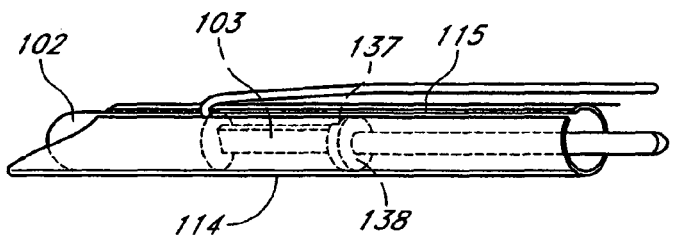
Figure 51C:
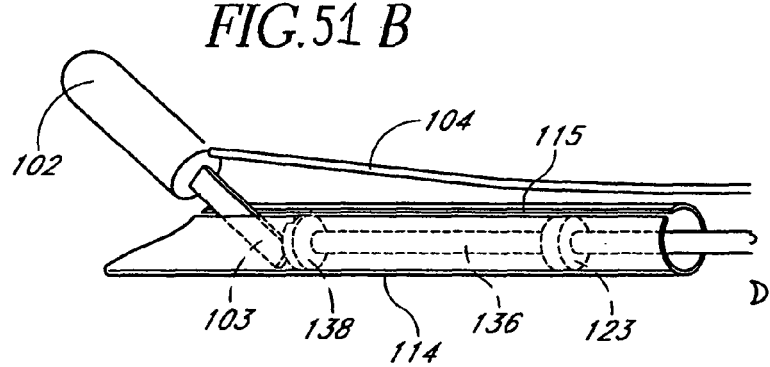
Figure 51D:
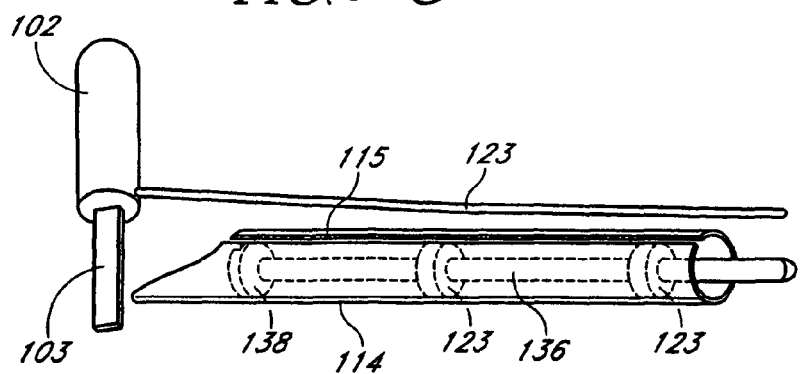

Another aspect of the T-tag fastener delivery device shown in FIGS. 51A-51B is that is shows another means to force or maintain the suture tail 104 external to the slotted penetrating cannula 114. The pusher assembly is configured to exclude the suture tail 104 of the T-tag fastener from the slot 115 of the slotted penetrating cannula 114 by the sizing of interface knob head 138 and, optionally, one or more other interface knobs 123 positioned along the pusher rod 136.

The T-tag fastener delivery device may have a fixed orientation with respect to the endoscope. Preferably, a visual indication of the delivery device orientation is provided for the endoscope operator. Alternatively, the delivery device may be rotatable with respect to the endoscope. This will require a mechanism for controlled rotation of the delivery device, e.g. a rotating shaft with gears to transmit the rotation to the delivery cannula, and a visual indication that changes to indicate the rotational orientation of the delivery cannula. With a video endoscope, this can be done electronically and indicated on the viewing monitor.

It is also possible to orient a T member 102 of a fastener after insertion. As shown in FIG. 52A, an attachment spacer or standoff 322 that is part of the fastener could be configured to transmit rotation from the delivery device or another tool 324 to the T member 102. Coupling structures 326, 328 can be incorporated on the distal and proximal ends of the standoff 322. The coupling structure 326 at the distal end of the standoff 322 would be configured to engage the deployed T member 102 and the coupling structure at the proximal end 328 of the standoff would be configured to mate with the delivery device 324, which will have a rotational drive mechanism. The standoff 322 would transmit rotation from the drive mechanism to the T member 102 as shown in FIG. 52B and after the delivery device 324 is removed the standoff 322 will serve as a spacer between the T member 102 and the attached device.

Similarly, the T member can be oriented directly by a rotational drive tool 330 that is passed over the suture tails and through the tissue, where it engages the side of the T member 102 to transmit rotation to the deployed T member 102 as shown in FIG. 53. The tool 330 is removed once the T member 102 has been rotated to the desired orientation.

Rollers, a low friction coating or other material or structure on the T member of the fastener would allow the fastener to slide on the serosa and thereby direct itself to a desired orientation. A roller or low friction material on the T member would also facilitate reorienting the T member to a desired orientation using a rotational drive tool as described above.

One other aspect of T-tag fastener delivery is the potential for a T member to pass proximally through the track formed by the penetrating cannula rather than rotating to be parallel to the tissue surface as desired. In many cases the connection of the T member and the stem can induce rotation of the T member. If the T member is attached to a suture tail, for example as shown in FIG. 51A, other means may be desirable to induce T member rotation. The structures shown in FIGS. 50A-50D and 51A-51D can be used, with or without orientation control, to induce T member rotation and avoid inadvertent retraction of the T member through the tissue track.

One of the challenges when performing endoscopic suturing, stapling or other types of attachment, e.g. with T-tag fasteners, is that the tissue tends to move away from the attachment device. A separate grasper can be inserted through an instrument lumen in the endoscope for holding the tissue, but this approach has its drawbacks because it is very difficult to achieve a good cooperation between the two instruments. To facilitate endoscopic attachment methods, a better cooperation can be achieved when an attachment device is combined with or otherwise mechanically linked to a grasper.

In one embodiment shown in FIG. 54A, the combined instrument 400 includes a flexible grasping forceps 416, for example a rat-tooth grasper, with an opening 402 through the jaws 404 of the grasper. Coaxial with the jaws 404 of the grasper 416 is a lumen 406 for passing an attachment device 408 (shown extended) through the opening 402 in the jaws 404. The grasper operating mechanism must be modified to accommodate the coaxial instrument lumen 406. The attachment device 408 may be an endoscopic suturing device, a stapler, a T-tag fastener delivery device or other known endoscopic attachment device. Alternatively, the lumen 406 for passing the attachment device may exit the shaft beside the jaws 404 of the grasper, potentially simplifying the construction of the grasper operating mechanism and obviating the need for an opening in the jaws. In another alternative configuration, the attachment device may be integrated into the combined instrument.

In another embodiment shown in FIG. 54B, the combined instrument 400 includes a corkscrew-type grasper 410 with a lumen 406 for passing an attachment device 408 (shown extended) coaxial with the opening 412 through the center of the corkscrew grasper 410.

In another embodiment shown in FIG. 54C, the combined instrument 400 includes a grasper 416 with multiple curved needles 414 that penetrate the tissue in opposing directions to grasp the tissue. Coaxial with the grasper 416 is a lumen 406 for passing an attachment device 408 (shown extended) between the curved grasping needles 414.

The combined instrument 400 is introduced endoscopically and the distal end is maneuvered into contact with the tissue to be attached. The grasper 416 is actuated to hold the tissue and the attachment device 408 is passed through the lumen to deliver a suture needle or fastener into or through the tissue. Because the grasper 416 and the attachment device 408 are so closely linked, the tissue cannot move out of the way of the attachment device 408, allowing the suture or fastener to be delivered through the tissue reliably and efficiently.

Alternatively or in addition, a vacuum coupling cuff on the distal tip of the endoscope including at least one radially outwardly directed cavity in communication via a vacuum lumen with a vacuum source can be used to allow vacuum holding of the tissue during attachment.

Figure 55A:
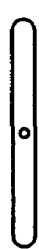
FIGS. 55A-55H show different possible configurations of T members.
Figure 55B:
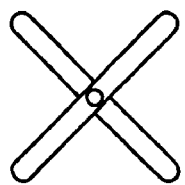
Figure 55C:
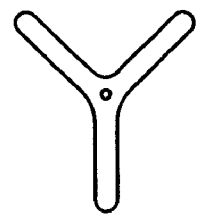
Figure 55D:
Figure 55E:
Figure 55H:
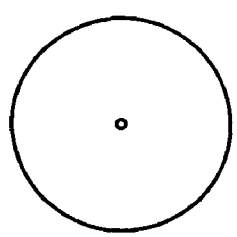
Figure 55F:
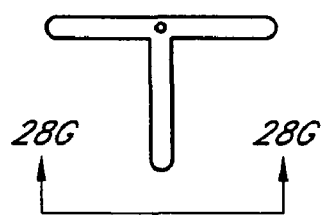
Figure 55G:
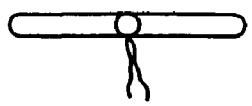

In some applications of the T-tag fastener, it will be advantageous to provide different configurations for the T member (s). FIGS. 55A-55H show top views of some possible T member configurations. FIG. 55A shows a straight bar-shaped T member. FIG. 55B shows an X-shaped T member. FIG. 55C shows a Y-shaped T member. FIG. 55D shows a V-shaped T member. FIG. 55E shows an A-shaped T member. FIG. 55F shows a T-shaped T member. FIG. 55H shows a circular or disc-shaped T member. The X, Y, V, A and T-shaped members may optionally be elastically deformable or pivotable at the center to provide a low insertion profile. FIG. 55B shows an example of such a pivot. These configurations of T member will provide greater anchoring force and/or reduced pressure on the tissues where they are attached. Although these T members have different configurations in the top view, they will still have an approximately T-shaped configuration in the side view, as shown in FIG. 55G, which is a side view of the T-shaped T member in FIG. 55F.

Expandable or swellable T members also have advantages for greater anchoring force and/or reduced pressure on the tissues where they are attached. A T member could be configured of a material that is initially small and/or soft for insertion of the T members. After insertion, the T member would expand or swell and then harden in the expanded configuration. This could result from a chemical reaction that is initiated by absorption of water or another reactant. A reagent in the material of the T member or added to it after insertion could initiate or catalyze the reaction of a hardenable material, e.g. a cyanoacrylate adhesive. Various materials and configurations for this function are described in the parent application Ser. No. 10/698,148.

Other enhancements can be applied to the T-tag fasteners described herein and those described in the parent application Ser. No. 10/698,148 and provisional 60/613,917. For example, the T member of the T-tag fastener can be configured to minimize pressure concentrations on the tissue. When applied by direct insertion, the T member of the T-tag fastener can be configured to distribute forces over a larger surface area. For example, the T member can be configured as a disk, square, rectangle or other shape with a large surface area. For blind insertion, the T member of the T-tag fastener can be configured to expand after insertion through the tissue to distribute forces over a larger area. For example, the T member can expand to form a disk, square, rectangle, I, X, Y or other configuration with a large surface area, as described herein (e.g. FIG. 55A-55H) and in the prior application. Alternatively or in addition, to reduce the potential for erosion at the end of the T in some clinical situations it could be beneficial for the ends of the T to have increased dimensions or configurations (for example a round ball shape) to reduce pressure at the end of the T and/or increased flexibility which will result in a reduction of the angle between the gastric wall and the ends of the T. This would reduce the forces between the T and the gastric wall and therefore reduce the potential for erosion at the ends. Structures that could accomplish this could include tapered thickness or cross section to reduce the bending moment. Alternatively or in addition, changes in material properties such as hardness, bending modulus and/or elongation can accomplish the same result. For example the T near the stem could be of a material of a durometer such as Shore 65D or higher the material may change as one moves out along the arms of the T transitioning through 55D/100 A to 90 A durometer or lower. Rounding, smoothing and structures that otherwise distribute forces over a larger area will also serve to reduce erosion at the ends of the T. A circular shaped T may be particularly desirable to reduce erosion.

All or a portion of the fastener can be coated and/or made with a material that will encourage tissue ingrowth to create a seal and to promote a strong and durable attachment. All or a portion of the fastener can be coated and/or made with a swellable material to create a seal and/or to spread out the force of attachment over a greater surface area, thereby reducing the pressure on the tissue. All or a portion of the fastener can be coated and/or made with a material that is biodegradable or bioresorbable. Examples of such coatings materials are described in the parent application Ser. No. 10/698,148.

In some of the examples herein and in the prior application, the T-tag fasteners are placed transmurally or through a full thickness plication. In an alternate method, an intramural T-tag can be placed submucosally, preferably in the serosa, where the T member would anchor the suture. The T would have a structure that is all or partly biodegradable. In this way, for those applications in which the sleeve device is intended to be removed after a sufficient amount of time depending on the needs of a particular patient, all or part of the T would degrade after removal of the sleeve device. Alternatively, the tension elements of the T-tags can be clipped off.

Following are descriptions of attachment devices and other means for securing an implantable device within the gastrointestinal system. The implantable devices and/or attachment means can be configured to avoid causing excessive pressure within the tissue by having compliance that is compatible with the gastrointestinal tissues where it is attached. Device compliance can also be important for providing a leak free seal between an implanted device and the tissue at the attachment point. Compliance can be provided in the radial or circumferential direction and/or in the vertical, axial or longitudinal direction. The device may have different compliance in different regions to be compatible with the tissue at the attachment point and at other portions of the gastrointestinal tract through which it runs. The device may have different compliance in different directions to be compatible with the tissue at the attachment point while simultaneously achieving other goals of the device. Compliance can be provided in a number of different ways. One way is by elastic or plastic deformation of the device and/or the attachment means. Another way is by a mechanical decoupling that allows relative movement between the device and the attachment points, and/or between the attachment points themselves, without transmitting excessive force or pressure to the tissue.

In some clinical situations, it will be desirable to match compliance between the device and the tissue to which it is attached. In other situations, based upon the clinical situations, it will be desirable to provide a device with higher or lower compliance than the tissue to achieve certain objectives. For example, maintaining the position of the proximal end of an attached sleeve device will require a device that is relatively noncompliant in at least the axial direction.

The implantable devices and/or attachment means described herein can utilize one or more of the following features to modify the compliance:

1) Highly-elastic materials (large amounts of stretch with low forces)
   a) Composite structures with elastic or super-elastic portions
2) Pleated materials (minimal force until pleats straighten)
   a) Similarly, other types of loose (gathered) or hanging (e.g. dangling sutures) connections
3) Fenestrated structures (e.g. cuts or slits)
   a) Can optionally use slidable overlapping elements to reduce/eliminate leaks at the slits
4) Stretchable weaves or knits
   a) Cylindrical and/or flat (e.g. an expandable or self-expanding stent or fabric)
5) Elastic, hinged and/or slotted structures that allow relative motion of components
   a) Can also use overlapping for leak control
6) Isolated or independent attachments
   a) Attachments to the GI tissue that are not connected
      i) They can initially be isolated and later connected
      ii) They could be interfaced with another device in a manner that does not restrict their relative motion (e.g. long hanging tethers)
7) Combinations of the above Other features may be incorporated in such structures such as:

1) Reinforcement at attachment points
   a) e.g. incorporation of fabric in a molded elastic structure
2) Clips, hangers or other means for sleeve interface at individual points
   a) For both isolated coupled and decoupled interfaces
3) Materials that encourage ingrowth and/or overgrowth
4) Separation of the functions of attachment and sealing
   a) To allow greater compliance at the attachment without increasing leakage
5) Means to maintain a substantially constant restricted volume within and between the device and stomach.
6) Through control of the degree and direction of device compliance.

Certain methods for the use of such structures include:
1) Treating the tissue at the GEJ to eliminate or minimize distention
   a) Creation of fibrotic or scar tissue
      i) Chemical, RF or other energy
      ii) Permanent or temporary to allow healing/seasoning of the attachment
   b) Thereby reducing the requirement for a compliant cuff or other attachment
2) Treating the tissue at the GEJ to increase tissue strength
   a) Creation of fibrotic or scar tissue
3) Allowing time for a primary attachment to heal before implantation and attachment of one or more secondary devices e.g. a sleeve.

Preferably, the attachment cuff 260 is compliant in the radial direction so that expansion and contraction of the stomach and esophagus due to contents and/or muscular action will not place additional, or actually reduce, stress on the attachment points. An elastomeric material, such as silicone or polyurethane that provides approximately 150% or more stretch in the radial direction is preferred. At the same time, the attachment ring can have enough lateral rigidity to act as a mounting platform for the gastrointestinal sleeve device and to resist downward movement due to the weight of the gastrointestinal sleeve device and its contents and peristaltic traction on the sleeve. The lateral rigidity of the attachment ring can be enhanced with radially oriented bending reinforcements, such as ribs or embedded reinforcement members. Alternatively, the attachment cuff can be flexible and compliant and other means such as hooks, sutures staples, etc., can be used for sleeve attachment.

Another strategy for avoiding excessive pressure on the gastric wall at the attachment points is to reduce the weight that the device attachment must support. This can be accomplished with spiral or longitudinal reinforcement members and/or inflatable balloons for structural support, particularly in the gastric portion of the gastrointestinal sleeve device, as described in the prior application. These features will help to transfer some of the weight to other structures of the stomach such as the antrum or the pylorus and will reduce the tension on the attachment at the GEJ. Likewise, additional attachments points at other points in the stomach will help to reduce the tension on the attachment at the GEJ. Attachment at the pylorus or other points in the stomach will also provide an added measure of safety. If the primary attachment at the proximal end of a sleeve device ever came unfastened, these additional attachment points would prevent the sleeve device from passing through the pylorus and becoming lodged in the intestine.

Figure 56A:
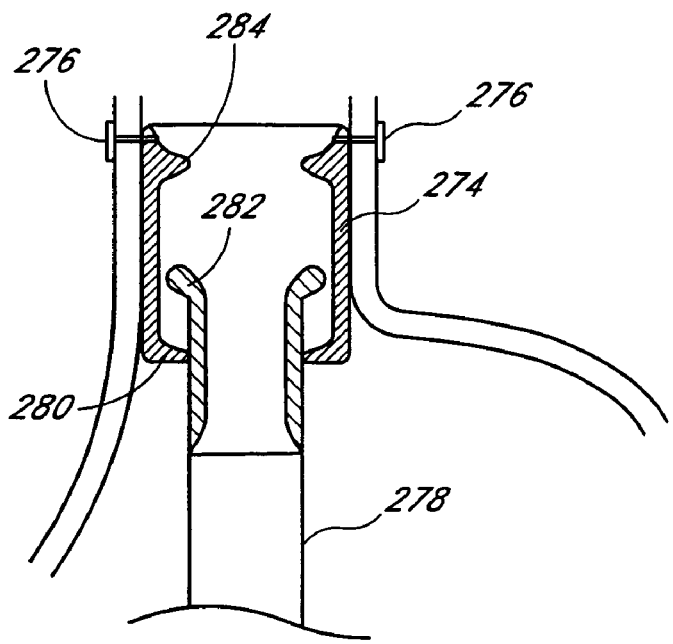
FIGS. 56A-56B illustrate another means for removably attaching a gastrointestinal sleeve device.
Figure 56B:
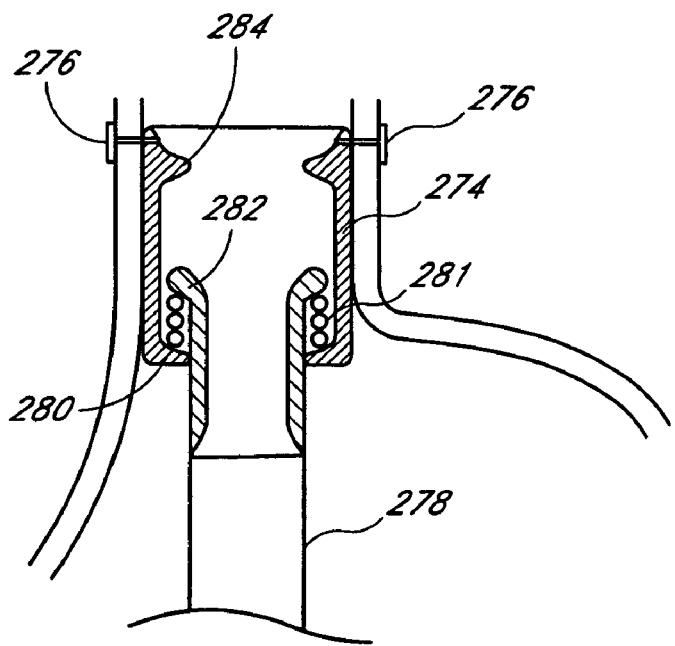

Another strategy for avoiding excessive pressure on the gastric wall at the attachment points is to provide an axially "floating" attachment for the gastrointestinal sleeve device so that stress transferred to the esophageal or gastric walls can be minimized or controlled. For example, FIG. 56A illustrates another means for attaching a gastrointestinal sleeve device that uses a compliant expandable or self-expanding cuff or stent 274 within the patient's esophagus. The gentle expansion of the cuff 274 anchors it in the esophagus without placing undue pressure on the tissues. One or more T-tag fasteners 276 or other fasteners may be used as an additional attachment means. Rather than being solidly attached to the cuff 274, the proximal end of the gastrointestinal sleeve device 278 has a floating attachment so that that expansion and contraction of the stomach and esophagus due to contents and/or muscular action will not place additional stress on the attachment points. One example of a floating attachment is to have an annular ridge 280 on the inside of the cuff 274 and a ring 282 on the proximal end of the gastrointestinal sleeve device 278. The ring 282 is sized so that it merely rests on top of the annular ridge 280, but cannot be pulled through it. The annular ridge 280 supports the gastrointestinal sleeve device, but it does not transfer any radial force from the gastrointestinal sleeve device to the esophageal or gastric walls. Optionally, a metal coil or other type of spring 281 can be used to couple the ring 282 and annular ridge 280, as shown in FIG. 56B. If desired, the floating attachment can also be combined with other features to allow the gastrointestinal sleeve attachment to float or expand and contract in the radial direction, as well as in the longitudinal direction. Optionally, a proximal annular ridge 284 may be formed near the proximal end of the expandable cuff 274 to limit longitudinal motion of the floating attachment in the proximal direction. Other means, such as the fasteners described herein and those described in the prior patent application can be used in place of the cuff to fasten a floating attachment of this type at the GEJ. Furthermore, the connections depicted in FIGS. 56A-56B, regardless of the "floating" feature described above, illustrate attachments that can be detached with minimal trauma to the surrounding tissue.

An alternate means of implementing an axial floating attachment uses vertically mounted isolated sliding attachment members can be used as an attachment structure for an implanted device. FIGS. 57A and 58A-58C show an example of vertically mounted isolated sliding attachment members 340 in a patient's stomach. This allows a maximum of relative motion between attachments with a minimum of force resisting that motion. The sliding vertical attachment allows vertical motion similar to that achieved with the floating attachment shown in FIGS. 56A-56B. Each of the isolated attachment members 340 is attached to the wall with one or more T-tag fasteners 130 or other types of fasteners. Although FIG. 57A shows an attachment member 340 attached with two T-tag fasteners 130, attachment of the attachment member 340 using one T-tag fastener 130 is also contemplated. Typically, 4-16 attachment members will be fastened around the periphery of the esophagus or stomach in the vicinity of the GEJ. The length of the attachment members helps to distribute the attachment force or pressure exerted on the tissue. The attachment members could be completely separate or they may linked to one another by high compliance members or a membrane that would help to position and orient the members for attachment, but that would allow the members to float like separate attachment points. The linking members or membrane may be configured to encourage ingrowth/overgrowth for attachment and sealing. Alternatively, the device that is mounted on the attachment members may provide a seal against the gastric mucosa.

Once the attachment members 340 have been fastened to the stomach wall, the implantable device 120 is connected to them using a like number of sliding connectors 341 attached to the implantable device 120. The sliding connectors 341 are configured to allow vertical movement of the implantable device 120 with respect to the attachment members 340 and the stomach wall. Stops or detents may be included to limit the vertical movement of the implantable device 120. In the example shown, the sliding connectors 341 are configured as channels that are slidably connected to rail-shaped attachment members 340. Other configurations of attachment members 340 and sliding connectors 341 are also possible.

FIG. 57B shows an example of a vertically mounted isolated hook attachment member 440 in a patient's stomach. The hook attachment member 440 is adapted to be attached to the stomach wall using T-tag fasteners 130 or other fasteners discussed herein. The hook attachment member 440 is adapted to engage complementary latching structures 450, such as loops or recesses, attached to or formed in the proximal end of the sleeve device 460. The hook attachment member 440 may be constructed so that it can be releasably secured to the complementary latching structure 450 such as the loop shown in FIG. 57B, for example by constructing the distal tip of the hook 440 so that it curves around the latching structure 450 such that the hook 440 will not disengage from the latching structure 450 during normal movement of the stomach. The hook attachment member 440 and complementary latching structure 450 may also be constructed to be releasable with minimal trauma to surrounding tissues when desired. Alternate embodiments of releasable connections comprising locking or securable attachment members or surfaces attached to the stomach wall and complementary engaging structures attached to the sleeve device are also contemplated. Alternatively, the attachment members or surfaces, such as hooks, may be attached to the sleeve device, while the complementary engaging structures are attached to the stomach wall.

The use of isolated attachments to attach a sleeve within the GI tract has been previously disclosed herein and in parent application Ser. No. 10/698,148. Isolated attachment allows a maximum of relative motion between attachments with a minimum of force resisting that motion. As has been discussed, the attachments can be left in place for a time to heal and become secure prior to the attachment of a sleeve. This concept can be extended to the use of a cuff, which interfaces a replaceable sleeve with GI tissue. Isolated attachments can be placed in the GI tissue, a period of time can allow healing of these attachment points and then the reusable cuff can be fastened to the GI tissue using the previously placed isolated attachments.

Figure 59:
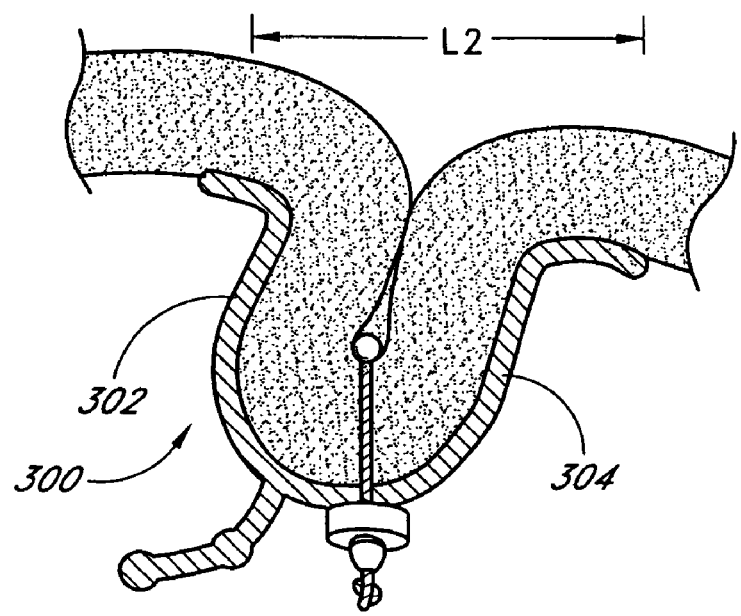
FIGS. 59-60 show a compliant fastener that can accommodate large gastric wall motions.
Figure 60:
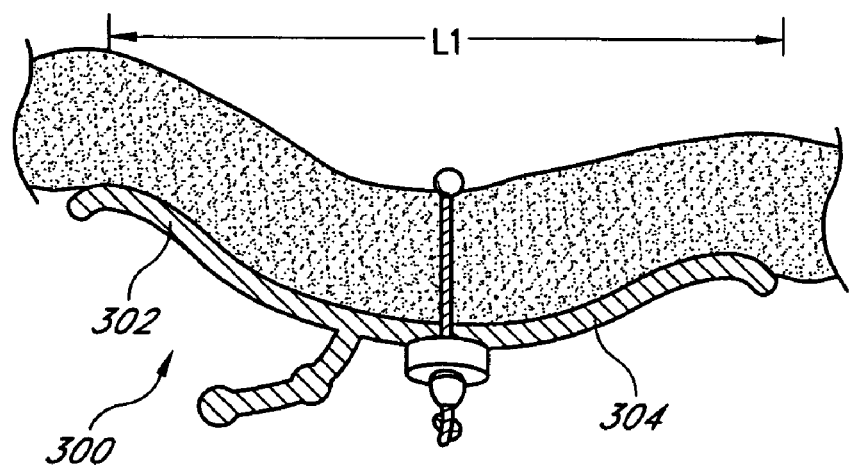

FIGS. 59 and 60 show one manner by which larger gastric wall motion can be accommodated by forming the device/gastric wall interface in a compliant manner. This can be a compliant device or a means by which the device can move to minimize motion relative to the tissue. Specifically, as tissue moves, the device would move with the tissue rather than resist the motion, which could lead to mucosa/device separation. However, device motion could be limited to the ability of the mucosa to maintain its integrity.

FIG. 59 shows a compliant attachment ring device 300 for use with T-tag fasteners or other types of fasteners. The attachment ring device 300 creates a plication (fold) and then controls the force to maintain the plication against the forces in the plicated tissue that would tend to straighten the fold. In FIG. 59 the attachment ring device 300 is shown in a normal resting position, flexible or compliant upper 302 and lower 304 flanges on the ring help maintain the shape of the plication. FIG. 60 shows the compliant attachment ring device 300 with tension exerted on the tissue at the tissue/device interface. The flexible or compliant upper 302 and lower 304 flanges on the ring open up to compensate for the tension, which reduces the force seen at the attachment points. When the tension is reduced, the compliant attachment ring device 300 will return to its normal resting position.

FIGS. 61A-61B show another embodiment of a flexible attachment cuff device 450. The attachment device 450 has a generally cylindrical outer wall 452 with an inward-facing lower flange or ridge 454, and the upstream end of the gastrointestinal sleeve device 458 has a corresponding outward-facing upper flange or ridge 456. This embodiment of the attachment device is preferably formed of a flexible biocompatible polymer such as silicone or polyurethane, which may optionally be reinforced with Dacron or other fabric. The material is optionally coated as described herein for encouraging ingrowth and/or resisting the attack of gastric secretions. All or a portion of the tissue contacting surfaces may be made from or covered with a material that encourages tissue ingrowth.

The attachment device 450 is passed through the esophagus and attached to the stomach wall, preferably near the GEJ. The attachment device may include a sewing ring or other features, such as those described herein, to facilitate attachment to a plication or directly to the unplicated stomach wall. The gastrointestinal sleeve device 458 is then passed through the esophagus and into the stomach and intestine. The upper flange 456 on the sleeve device 458 is held by the lower flange 454 of the attachment device 450. Optionally, the upper flange 456 on the sleeve device 458 may have a sliding fit with the cylindrical outer wall 452 to allow for relative motion between the sleeve device 458 and the attachment device 450, with the lower flange 454 on the attachment device 450 serving to limit the downward motion of the sleeve device 458. The sliding fit will help to reduce the tension transferred to the gastric wall from the sleeve device 458 and the weight of its contents.

In general, a first retention surface such as an upwardly facing surface on a radially inwardly facing flange or plurality of tabs on the attachment device (cuff) 450 limits distal movement of the sleeve by contacting a second retention surface on the sleeve. The second retention surface may be a downwardly (distally) facing surface such as the distal surface of a radially outwardly facing annular flange or plurality of tabs on the proximal end of the sleeve. In this configuration, the sleeve may be passed through the cuff and simply "dropped" into place and the first and second retention surfaces limit further distal travel of the sleeve relative to the cuff.

Alternatively, the attachment device may include an interlock or snap fit structure for capturing the upper flange of the sleeve device to reduce or eliminate relative motion between the sleeve device and the attachment device in either the proximal or distal direction. FIGS. 62A-62B show an embodiment of the attachment device 460 with an inward-facing lip 462 above the lower flange 464 to releasably capture the upper flange 456 of the sleeve device 458. Preferably, the inward-facing lip 462 has a sloped or tapered upper surface to create a smooth transition between the diameter of the attachment device 460 and the sleeve device 458 and to avoid creating an inner shelf that could catch food before it enters the sleeve device 458. The attachment device 460 may include an attachment ring or other features, such as those described herein, the referenced provisionals, and the parent applications, to facilitate attachment to a plication or directly to the unplicated stomach wall.

FIGS. 63A-63B show another embodiment of the attachment device 470 with an annular groove 472 above the lower flange 474 for capturing the upper flange 456 of the sleeve device 458. This geometry allows the inner diameter of the attachment device 470 to be matched to the inner diameter of the sleeve device 458, with no internal steps. The attachment device 470 may include a attachment ring or other features, such as those described herein, the referenced provisionals, and the parent application to facilitate attachment to a plication or directly to the unplicated stomach wall.

In other variations of these embodiments, the cylindrical walls can taper inward for attaching an implant device with a smaller diameter than the attachment device or they can taper outward for attaching an implant device with a larger diameter than the attachment device.

Each of these embodiments permits the sleeve to be dropped into place or snap fit into place by elastic or other deformation of the interlocking retention surfaces. The attachment can be made more secure by the addition of one or two or more staples, stitches of suture or t-tags. Removal can be accomplished using a removal tool with a stop surface for placing against a surface on the cuff to prevent proximal movement of the cuff, and a grasper for grasping the proximal end of the sleeve and pulling the sleeve to release it from the cuff without straining the connection between the cuff and the tissue. Any additional sutures can be snipped using conventional endoscopic cutting tools. The cuff may also be removed if desired, or a different sleeve may be introduced and secured to the cuff.

Figure 64:
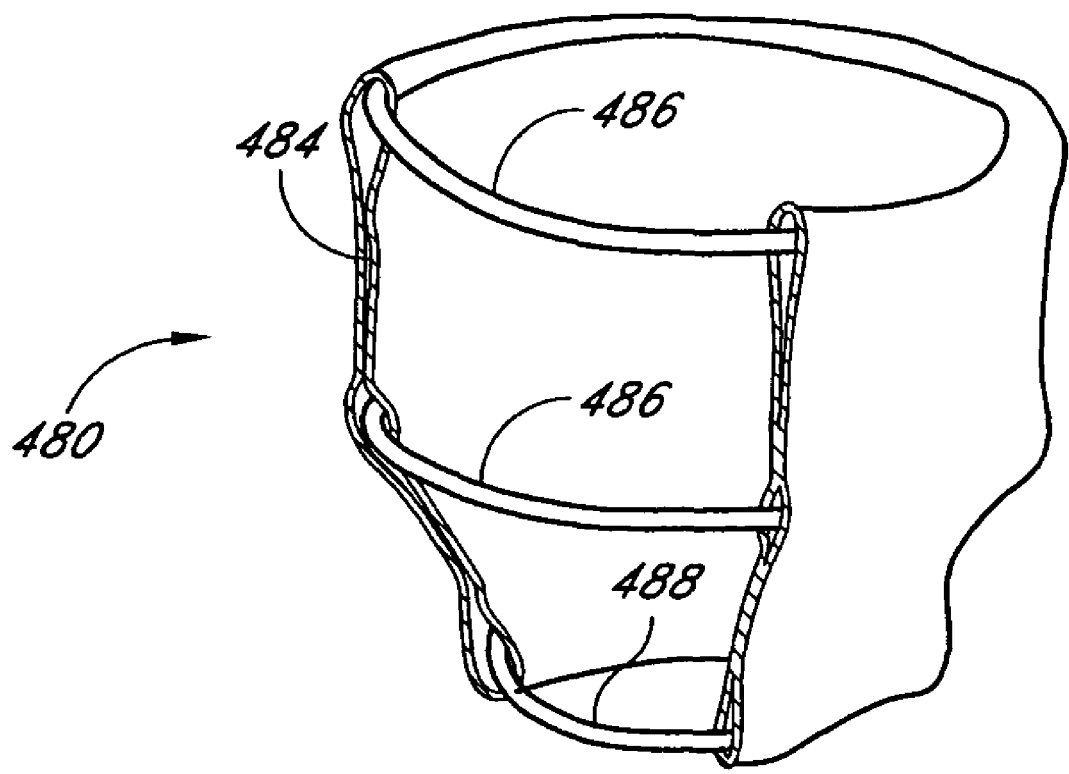
FIG. 64 is a cutaway drawing showing the internal construction of an embodiment of a flexible attachment device.

The flexible cylindrical attachment device 480 can be constructed from a number of materials and methods. By way of example, FIG. 64 is a cutaway drawing showing the internal construction of a cylindrical attachment device 480 made from woven or knitted material. The cylindrical wall 484 can be woven or knitted in the round or it can be sewn into a cylindrical configuration from one or more pieces of material. The cylindrical wall 484 is preferably supported with a resilient wire-reinforced or elastic filamentous ring 486 at the upper and/or lower ends. The upper edge 482 of the cylindrical wall 484 is optionally rounded or flared outward to minimize contact pressure on the gastric wall as described in the examples above above. A third wire-reinforced ring 488 may be provided at the lower end for attachment of a gastrointestinal sleeve device or other implanted device. Alternatively, a molded upper and/or lower flange or other features can be attached to the lower support ring for attaching a gastrointestinal sleeve device in the manner described above.

Figure 65:
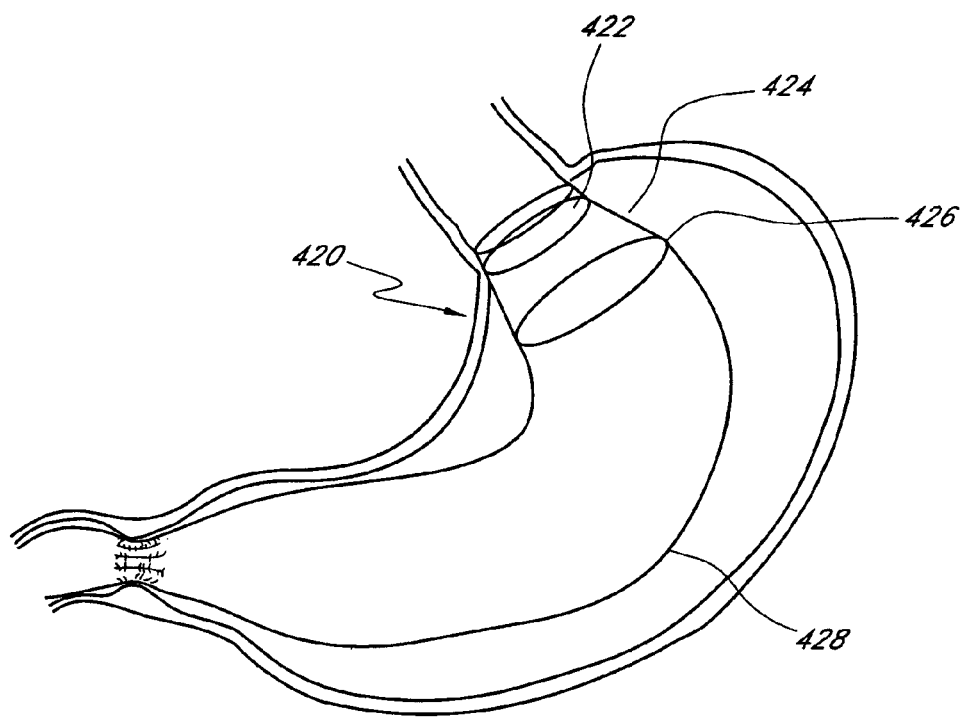
FIG. 65 shows an attachment device for attaching a treatment device that is larger in diameter than the attachment device.

In some clinical circumstances, it may be desirable to implant a treatment device that is larger than the attachment means. FIG. 65 shows an attachment device 420 fastened in the vicinity of the GEJ. At the upstream end of the attachment device 420 is an attachment ring 422 that fastens to the gastric and/or esophageal wall, for example using the apparatus and methods described herein. Suspended below the attachment ring 422 is a gastrointestinal sleeve device 428 for treatment of obesity. The entry of the gastrointestinal sleeve device 428 has a larger diameter than the attachment at the GEJ. To accommodate this, the attachment device 420 has an outward-tapering skirt 424 extending downward from the attachment ring 422. At the bottom edge of the outward-tapering skirt 424 is a device attachment ring 426 or other attachment means for fastening the upstream end of the gastrointestinal sleeve device 428 to the attachment device 420. Preferably, the outward-tapering skirt 424 is made of an impermeable material so that the attachment device provides a fluid-tight seal between the attachment point to the patient and the gastrointestinal sleeve device 428.

Alternatively, the attachment device can provide only a mechanical attachment and the gastrointestinal sleeve device can provide a seal against the gastric wall or a separate sealing device may be provided. In this case, instead of an impermeable skirt, the attachment device may have a suspension frame that provides a mechanical attachment between the attachment ring and the gastrointestinal sleeve device. The suspension frame may be made, for example, from wires or mesh or filaments that provide the necessary mechanical strength, but do not provide a seal. The skirt portion of the attachment device may also be constructed with an impermeable membrane over a suspension frame of this type. Optionally, the suspension frame may include adjustable length tethers for adjusting the distance between the attachment ring and the gastrointestinal sleeve device.

Preferably, the entire structure of the attachment device 420 is collapsible and expandable so that it can be easily passed through the esophagus in a folded, compressed or collapsed state and re-expanded once it is in the patient's stomach. Optionally, the final expanded diameter may be adjustable. Optionally the device 420 may be highly compliant and stretchable where it is attached to the gastric wall.

Although this example shows the implanted device mounted downstream or below the attachment device, in some clinical situations it may be desirable to mount an implant device so that it protrudes above the attachment device.

External Sleeve Interface

With (1) a device system where a primary attachment such as a cuff is placed in a tubular duct, e.g. at the GEJ, and a secondary device such as a gastrointestinal sleeve is removably attached to the primary attachment device and (2) placement of the system with a coaxial procedure, e.g. an endoscope passed down the esophagus, placement of the secondary device within the lumen of the primary device can be a simpler approach. However, certain advantages could be obtained if the secondary device were mounted on the exterior of the primary device. Various sleeve geometries with the sleeve portion of the interface being smaller diameter and internally coaxial to the cuff have been previously described.

Figure 66:
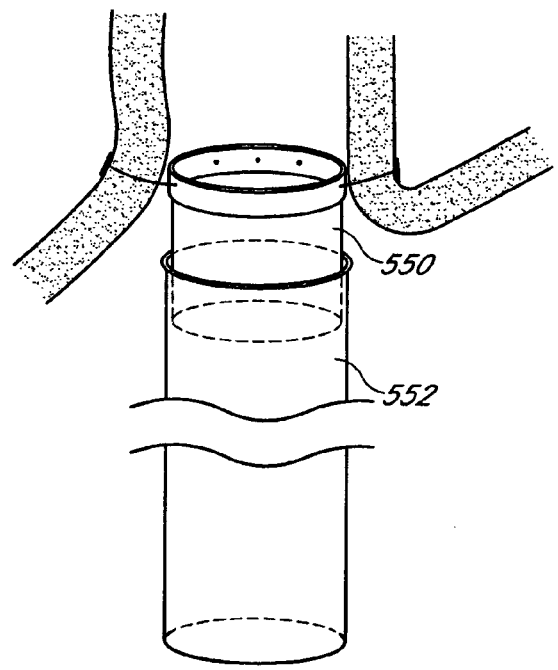
FIG. 66 illustrates an attachment cuff with an external sleeve attachment interface.

All of the configurations can be inverted such that the sleeve is of larger diameter and external to the cuff. Similarly, other interface designs such as hooks and eyes disclosed herein can be configured with the sleeve of a larger diameter than the primary mounting cuff. FIG. 66 illustrates an attachment cuff 550 with an external sleeve attachment interface. One of the potential advantages of mounting the sleeve 552 external to the cuff 550 is that such a configuration could be designed to be robust in resisting leaks.

If the proximal portion of the sleeve 552 were less compliant than the distal portion of the cuff 550, internal pressure would press the wall of the cuff 550 into sealing contact with the sleeve 552. In this situation, the seal will be maintained so long as the sleeve 552 stretches less than the cuff 550 as internal pressure increases. Also the distance the cuff 550 and the sleeve 552 overlap can be adjusted to improve interface performance related to leak resistance and/or retention strength. This system can also allow holes or perforations in either the cuff or sleeve in the region of overlap of an unperforated surface without allowing leaks. These holes or perforations may be used to attach the components. The sleeve 552 is removably connected to the cuff 550. Alternate removable connections between the sleeve 552 and the cuff 550, such as stitching, stapling, T-tags, hooks and loops including Velcro, magnetic interfacing structures, adhesives, friction interfitting structures, and various other complementary interfitting structures, depending on the desired performance, are contemplated.

Separation of Attachment and Sealing

The functions of attachment and sealing can be separated, for example highly compliant attachment can be placed at the GEJ and a sealing connection can be placed upstream towards the esophagus. The compliant attachment can be accomplished with gathered or pleated stretchable material. The sealing connection can be configured similar to a covered expandable or self-expanding stent. These separate structures can be improved by structure (e.g. one or more vertical bellows-like pleats) that would allow relative vertical displacement of the sealing and attachment zones.

Figure 67:
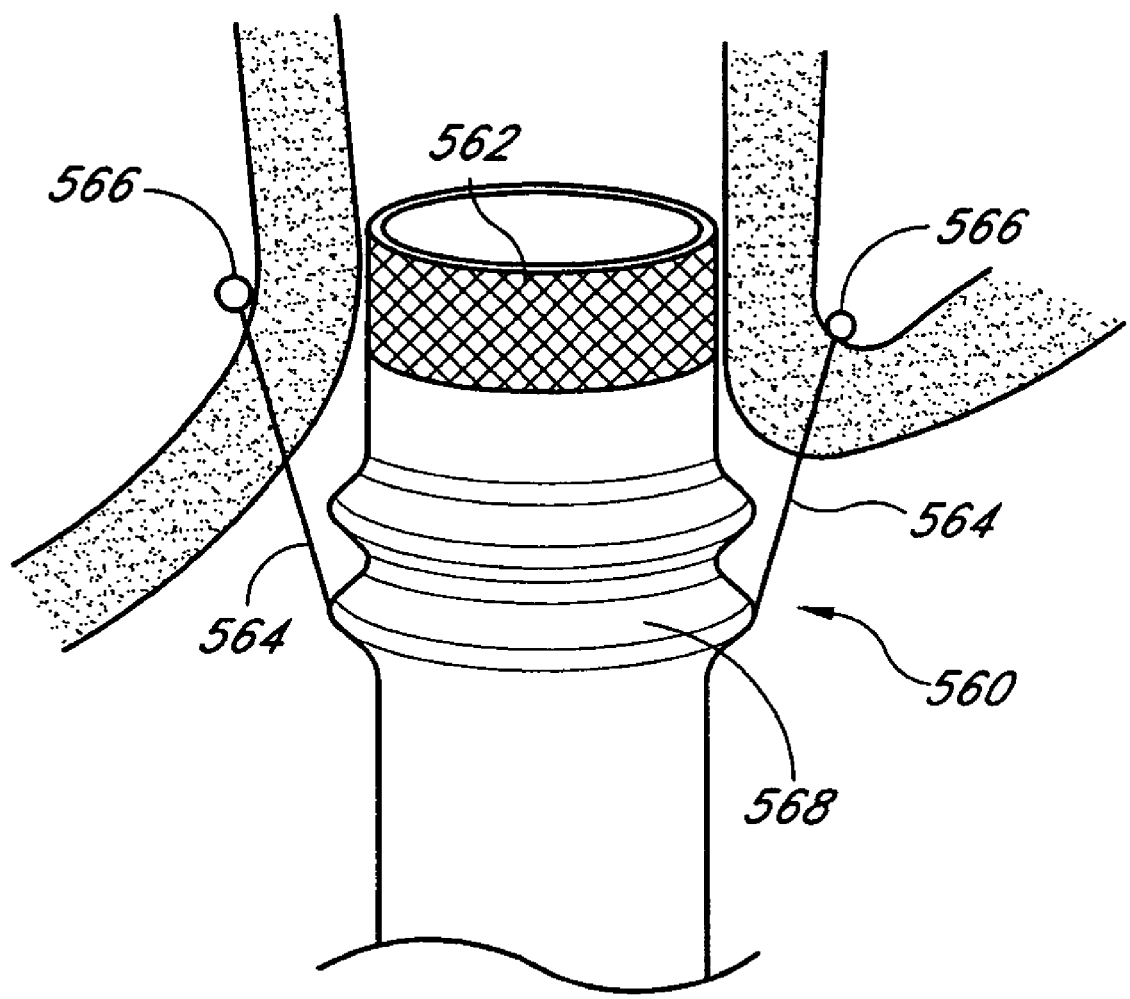
FIG. 67 illustrates an attachment cuff with separation of the attachment and sealing functions.
Figure 74A:
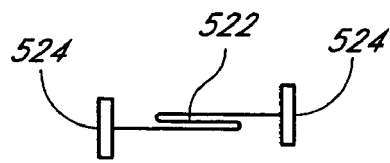
FIGS. 74A-74E illustrate an embodiment of a fastener with controlled suture lengthening to compensate for tissue thickening.
Figure 74B:
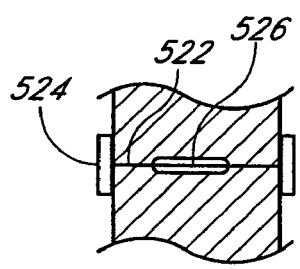
Figure 74C:
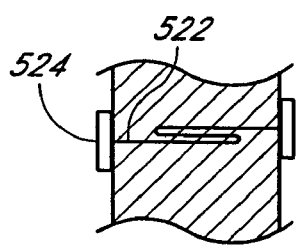
Figure 74D:
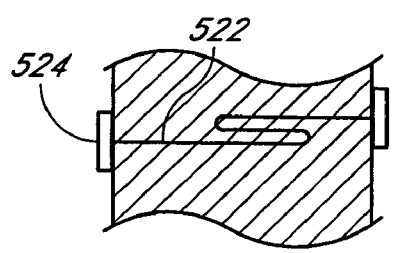
Figure 74E:
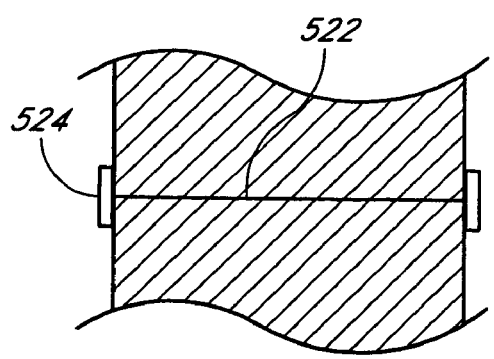

FIG. 67 illustrates an attachment cuff or gastrointestinal sleeve 560 with separation of the attachment and sealing functions. A sealing zone is created, for example using an expandable or self-expanding stent 562 or a compliant material cuff attached with T-tag fasteners. The attachment cuff or gastrointestinal sleeve 560 is attached to the gastric wall downstream of the sealing zone, for example using elongated tethers 564 with transmural T-tags 566. Preferably, the attachment cuff or gastrointestinal sleeve 560 is configured to allow some longitudinal compliance between the sealing zone and the attachment zone. In the example shown, one or more accordion folds 568 create a zone of longitudinal compliance between the sealing zone and the attachment zone.

Distal Compliance

Similarly, the restrictive component of a morbid obesity treatment system has usually been depicted as being at or distal to the attachment point of the device. Since restrictions may be most effective when coupled with a constant or restricted volume proximal to the restriction this suggests that little or no compliance would be preferred at the attachment. Alternatively, the compliance of the attachment can be factored into the definition of the restricted volume. In some clinical situations where high compliance is desirable it could be preferable for the restricted outlet of the restricted volume be placed proximal to a compliant attachment e.g. attachment 562 in FIG. 67. This can allow significant displacement of the compliant attachment without changing (increasing) the restricted volume proximal to the restricted outlet.

Compliant attachment means can be used at or near the GEJ or cardia of the stomach. These attachments can be connected to a restrictive component, which is maintained in a sealing connection with the walls of the GI tract proximal to the attachment. The means used to connect the restrictive component (a device that has a restrictive opening and seals with the walls of the GI tract) do not need to be impervious to masticated food. Sealing means can be passive (for example, an oversized device in a relatively smaller tubular duct) or active (for example, suture, anchor, staple, etc.) However, this sealing is not the primary attachment. It is merely to maintain a seal while the primary compliant attachment resists other forces.

Tissue Prestrengthening

In some clinical situations the gastroesophageal junction, or GEJ, is a preferred attachment point for a gastroesophageal sleeve device or attachment device as discussed above. Attachment at the GEJ excludes all gastric secretions from the interior of the gastrointestinal sleeve device to separate ingested food and liquids in the sleeve device from all digestive secretions. The gastroesophageal junction is one of the preferred attachment sites because the tissue wall is relatively thick at this location and it is relatively easy to access via a peroral route. More specifically, the non-glandular tissue directly above the squamo-columnar junction (a zone of tissue that is considered to be at the beginning of the GEJ) is the strongest tissue in this region and is currently thought to be the best place to attach a device, for example using T-tags, sutures or other fasteners.

In some clinical situations it may be beneficial to prestrengthen the tissue prior to implantation of a device such as a gastrointestinal sleeve device. For example, energy can be delivered in the form of RF, ultrasound or other known method to induce an inflammatory, coagulative or necrotic tissue strengthening reaction. Alternatively, placement of material in the serosal tissue of the stomach wall could generate a foreign body reaction that would progress from inflammation, to granulation of tissue and then to fibrosis. The tissue may initially weaken due to the inflammatory response, but the resulting fibrotic growth will strengthen the tissue. This effect could be enhanced by the choice of material an/or coatings, e.g. sclerosing agent, an acidic material or coating. The materials could be delivered endoscopically with a needle device through the biopsy channel of an endoscope. The needle delivery device could optionally also deliver an ink, dye or other marking means to facilitate location of the prestrengthened areas. Tissue reaction could take place in days, with 7-14 days being an approximate delay between prestrengthening and attachment procedures. FIGS. 68-69 show examples of tissue prestrengthening in the gastrointestinal system. In FIG. 68, the material 500 has been delivered into the gastric wall just under the mucosa 504. The granulation and fibrosis 502 start at this point and progress through the muscularis 506 to strengthen the tissue and prepare it for attachment of an implantable device. In FIG. 69, the material 500 has been delivered deeper into the gastric wall close to the serosa 508. The granulation and fibrosis 502 start at this point and progress through the muscularis 506 to strengthen the tissue and prepare it for attachment of an implantable device. Optionally, tissue prestrengthening can be accomplished by inserting a fibrosis inducing agent with a suture tail attached to it to allow it to be retrieved or used to guide a subsequent attachment to the prestrengthened location after it has had the desired affect on the tissue wall.

Material injectable to prestrengthen tissue could be: 1) liquid where natural processes would remove/break down or otherwise dispose of the liquid when it has completed its function; 2) biodegradable or dissolvable where natural processes would remove the material when it has completed its function; or 3) permanent where the material might be incorporated into the tissue to provide increased strength. All of the prestrengthening strategies described could be used at the time of the attachment procedure to enhance strength of the attachment.

The methods and apparatus described for tissue strengthening would be expected to result in some degree of tissue thickening as new collagen and fibrotic material will be deposited and/or generated at the location of the foreign body reaction. The duration of exposure can be controlled by use of timed release chemical stimulants and stimulants with known and potentially controllable half lives. Tissue thickening and tissue strength may be related and may facilitate durable attachment, however tissue thickening may be an inherently desirable result in some clinical situations. FIG. 70 shows an example of tissue thickening in the gastrointestinal system as a result of a material 500 injected or delivered into the gastric wall. Optionally, a suture or other filament 512 may be connected to the material to allow it to be retrieved or used to guide a subsequent attachment to the prestrengthened location after it has had the desired affect on the tissue wall and to halt additional tissue thickening.

Currently, tissue bulking agents are injected at or near the GEJ to treat GERD. Injection of non-bulking materials that initiate tissue thickening could accomplish the same end result. If the thickened tissue was, by itself or in conjunction with a supporting structure, to form a restrictive stoma, there could be specific advantages relative to a mechanical stoma. FIG. 71 shows an example of tissue thickening in the gastrointestinal system using a bulking material 510 injected or delivered into the gastric wall.

Tissue prestrengthening and/or thickening can be accomplished by inserting a fibrosis inducing agent with a suture tail attached to it. The fibrosis inducing agent will preferably also act as a scaffold for strength. The tail will allow easy identification of the location that has been strengthened for retrieval or guidance of follow on attachment procedures. Once tissue has strengthened, cuff and sleeve can be placed in a single combined procedure as the prestrengthened tissue will not require additional healing time to hold.

Other approaches to induce tissue prestrengthening and/or thickening include: Circumferential ablation (RF, microwave, ultrasound, etc); Over-dilation; Circumferential abrasion; and, Circumferential exposure to agent. An advantage of a circumferential area of tissue strengthening is that it only needs to be located along a vertical axis for subsequent attachment procedures.

Alternately or in addition to the above pre-strengthening of tissue, tissue can be treated to reduce its ability to move or stretch. This can be advantageous in that tissue that has limited stretch or motion may have less impediments to attachment. Tissue that has limited stretch or motion may impose fewer forces on an attached device and therefore impose less pressure that may lead to attachment failure. Furthermore, tissue that has limited stretch or motion may allow attachment of less compliant devices which can provide for advantages foe example simplified sealing.

Techniques described above to strengthen tissue can also help to limited GI tissue stretch and motion. Other methods that could be applied to reducing stretch and motion, and also for pre-strengthening, include the application of energy for example, by RF, ultrasound or laser. Means that include time release elements as well known in the art of drug eluting vascular stents and birth control devices can be used to provide and/or maintain a long lasting effect (reducing motion and stretch). Such time release means can optionally be combined with fasteners, permanent or replaceable attachment cuffs or proximal sleeve interfaces. Such time release means can optionally be combined with permanently implanted pre-strengthening materials where the material might be incorporated into the tissue to provide increased strength.

Suture Lengthening

In some clinical situations when using a transmural attachment, the wall of tissue may thicken after placement of the attaching device. FIGS. 72A-72C show schematically the effect of tissue thickening on a fixed length suture or fastener 520. In some cases this can progress to encapsulation. This thickening can result in increased tissue strength due to collagen deposition and/or fibrosis.

In some clinical situations it can be advantageous to maintain the attachment on the surface of the tissue to take advantage of the added strength of the thickened wall. FIGS. 73A-73C show controlled suture lengthening to compensate for tissue thickening. One manner in which this could be accomplished would be by using a suture 522 connecting the attachments 524 on either side of the tissue wall that would stretch as the tissue thickens.

One configuration of material that could have advantageous performance would: 1) not stretch for an initial period, for example 24-48 hours; 2) stretch at a relatively low force for the next period, for example 7-14 days; then 3) not stretch after the second period. This performance would be based upon a clinical situation where tissue proliferation (wall thickening) occurs between days 2 and 14. Alternatively, the material could: 1) not stretch for the initial period, for example 24-48 hours; 2) allow lengthening to 2× length at any time after the initial period, for example 48 hours; then 3) not stretch beyond 2× length.

FIGS. 74A-74E illustrate an embodiment of a fastener with controlled suture lengthening to compensate for tissue thickening. In this example, the fastener is configured to allow approximately 2× lengthening over a controlled time period and then to resist further lengthening. This can be accomplished as follows:

A portion of the suture 522 is folded at least about 2× or 3× as shown in FIG. 72A. A dissolvable or resorbable coating or adhesive 526 is added to the overlapping portion of the suture 522 to initially resist lengthening after implantation as shown in FIG. 72B. The coating 526 will dissolve or resorb after a predetermined period of time, releasing the folded portion of the suture 522 as shown in FIG. 72C. After dissolution of the coating 526, the suture 522 will lengthen without significant resistance as shown in FIG. 72D. FIG. 72E shows the suture 522 fully extended to its final length.

Figure 75A:
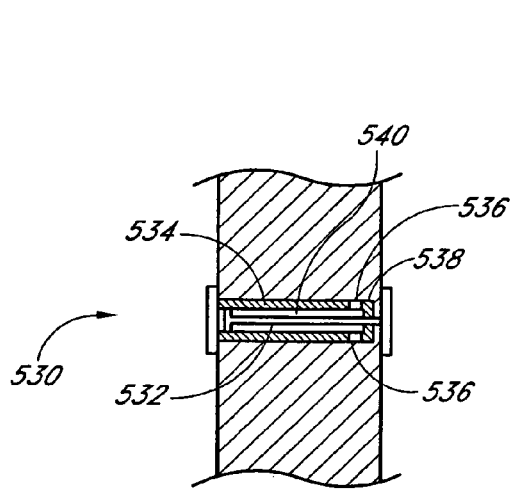
FIGS. 75A-75B illustrate another embodiment of a fastener with controlled suture lengthening to compensate for tissue thickening.
Figure 75B:
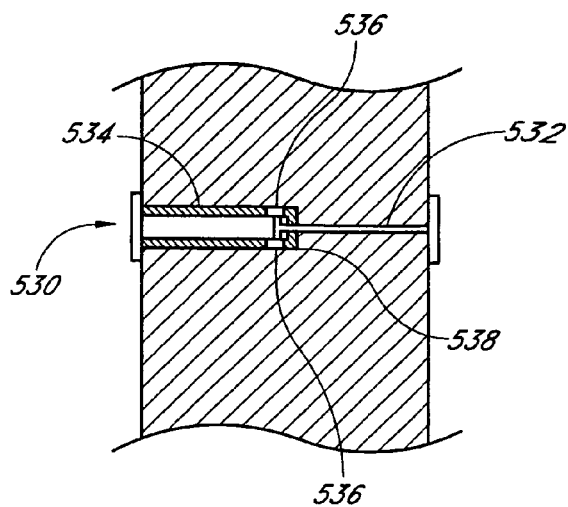

Lengthening could also be accomplished with a coaxial system. FIGS. 75A-75B illustrate another embodiment of a fastener 530 with a coaxial system for controlled suture lengthening to compensate for tissue thickening. The fastener 530 has a linear inner member 532 and a tubular outer member 534 in a telescoping coaxial arrangement. Ports 536 in the tubular outer 534 member allow fluid entry. A stop or detent 538 at the ends of the inner member 532 and outer member 534 prevent separation of the fastener 500. Similar to the system previously described, a dissolvable or degradable material 540 can be used to control lengthening. By restricting or controlling exposure of the biodegradable material to body fluids, the rate of lengthening can be optionally controlled.

Figure 76A:
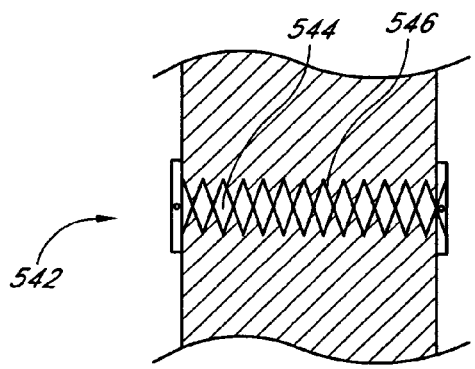
FIGS. 76A-76B illustrate another embodiment of a fastener with controlled suture lengthening to compensate for tissue thickening.
Figure 76B:
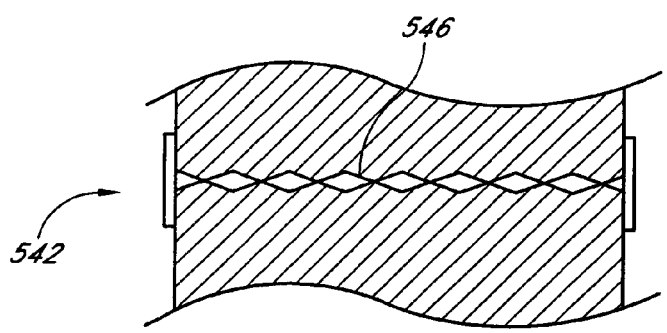

The principle of shortening/lengthening of a braided mesh can be applied to an automatically lengthening suture. FIGS. 76A-76B illustrate another embodiment of a fastener 542 using this principle for controlled suture lengthening to compensate for tissue thickening. A dissolvable inner core 544 holds the braided mesh suture 546 open, keeping the fastener 542 in a shortened configuration as shown in FIG. 76A. After the inner core 544 dissolves, the braided mesh suture 546 can lengthen as shown in FIG. 76B. Lengthening is accomplished by a change in angle of the braided fibers as the inner core dissolves, allowing the diameter to shrink.

An optimized yielding suture system for GI attachment could have differing responses to short impulse and long continuous loads. Viscoelastic polymer systems such as Tempurfoam resist short term impulse loads and yield to slow steady long term loads. Resistance to short term loads and yielding to long term loads could be advantageous in clinical situations where there can be temporary short term loading due to overeating while yielding to long term loads could relieve overpressurization of tissue to enable tissue perfusion to avoid tissue necrosis due to pressure and/or ischemia.

In other clinical situations yielding to short term transient loads may facilitate secure attachment when coughing, retching, swallowing etc. occur. Resistance and/or recovery in the face of lower and slower forces can return the suture to a normal length, facilitating leak free securing of an attachment.

Yield points and/or recovery points should be selected so attachment forces do not exceed the acute pull out force of a suture and/or T-tag. Acute pull out forces can be in the range of 3-9 pounds depending on the suture/T-tag configuration. This is of particular concern for short term impulse loads. Loads applied over longer periods should be selected to avoid ischemia and/or pressure necrosis. These forces can be very low and can be less than 1 pound.

In an ideal situation, a suture system will recover to a set length which results in no force applied to the tissue over extended periods of time. Attachment can resist forces between necrosis force/pressure if they are transient and allow tissue time for healing and/or recovery. A system whereby recovery after yielding occurs in a non-continuous manner thereby allowing tissue healing and/or recovery could be desirable in many clinical situations. This may be accomplished by materials that respond to outside stimulus (e.g. electrical, chemical, magnetic, etc.) that can be applied intermittently.

The length of the suture or other tension element which extends through the wall from the serosal surface to the mucosal surface, particularly when the tension element has a substantially fixed length under normal use conditions may also be important. The present inventors believe that the length of the tension element is in certain applications at least about 75%, often at least about 100%, and preferably at least about 120% and possibly at least about 130% of the thickness of the wall of the stomach through which the tension element is to be placed. Thus, for a patient having a wall thickness in the vicinity of the gastroesophageal junction of approximately 10-15 mm, suture lengths between the mucosal contacting surface of the implant and the serosal contacting surface of the retention element of at least about 10 mm, and often at least about 15 mm are contemplated.

The stomach appears to have unusual abilities to isolate foreign objects. Evidence of this is the lap band which can migrate from the serosal surface of the stomach into the lumen of the stomach without any immediate catastrophic event such as a leak of stomach contents into the body cavity which could be life threatening. The cause of such erosion is unclear but one theory suggests it is at least in part due to pressure.

The stomach is also a very active organ with an ability to stretch, compress, churn and move laterally relative to itself. This activity is normal in eating and digestion and can also function to isolate foreign objects.

These anatomical aspects make attachment of medical devices to the stomach quite challenging. A recent study at the Cleveland Clinic which sutured a prosthetic cuff to the GEJ showed that by 7 days 80% of the cuffs had become primarily detached. In one animal that was survived for two months, the device remained attached at 4 weeks but was only 25% attached by 60 days.

The present inventors have conducted a series of studies to explore the parameters of a successful attachment. Initial designs utilizing rigid rings lost attachment at a majority of points within four weeks.

Short term success at two weeks with a flexible cuff, with elastic ability, was achieved by using t-tags and placing them in the non-glandular tissue region of the GEJ.

However this same technique at five weeks did not maintain 100% attachment. One-Third of the attachment points migrated through the stomach, leaving no identified histological evidence of their path. The t-tags did not appear to be deformed.

The inventors then undertook a series of experiments at five weeks controlling for the amount of tension on the tension element, by placing serosal surface attachment devices having tension elements with a predetermined length relative to the thickness of the tissue wall. The thickness of the porcine stomach at the target site was measured, and the average of four tissue thickness measurements at the 3-6-9-12 o'clock positions was used as the nominal thickness. The absolute thickness was somewhat surprising at around 1 cm. This was perceived to be much thicker than what was thought. The reasons for this could be increased thickness in the area of interest of the GEJ, but it could also be due to the highly compressible nature of stomach tissue in that when it is held between the thumb and index finger it does feel 1 cm thick.

In three experiments conducted there was a clear trend that the looser the attachment (i.e., the longer the length of the tension element compared to the local wall thickness) the more attachment points held at five weeks. Results ranged from 10/12 migrations for the sutures sized at 50% of nominal thickness to 2/12 migrations for sutures sized at 100% of nominal thickness.

Another variable which was explored in the porcine model was the effect of changes in the surface area of the retention element. Silicone buttons having a 1 cm diameter were used instead of the t-tags. In one experiment conducted to date at a suture length of 75% of nominal thickness, 4/12 silicone buttons migrated through.

What seemed different about the silicone buttons is with two-thirds of the attachments in place it appeared upon gross inspection to be very strongly functionally attached, with high weight bearing abilities, perceptually greater than the t-tags.

From the experiments to date it appears that tension control is as important (if not more so) as the geometry of the serosal attachment device.

As discussed elsewhere herein, tension control could be addressed by using suture with limited elastic properties or other structural mechanism that would stretch or elongate and then return to their nominal length. Another way is to use an assumed thickness, based upon an average of actual measurements in humans, and preset the length of the tension element at a predetermined length (e.g., at least 115%, at least 130%) compared to the length of the average. The chances of success for this approach would likely be enhanced if the patient to patient variation is relatively small. A further approach would be to measure the thickness of the target tissue in each patient, and customize the length of the tension element at the clinical site, or provide kits with a cuff and an array of anchor assemblies with tension elements of different predetermined lengths from which the clinician can make a selection. Measurement could be accomplished, for example, with endoscopic ultrasound, like a device available from Boston Scientific.

Once the measurement is taken a variety of devices could be used to attach with a controlled length. Many of these devices have been previously described and include t-tags, inflatable silicone discs, molly type devices, radial spoke "umbrella" structures and others. They can be attached to suture with a fixed cuff to retention element length (or other means) or a strut member made of polymer or metal with a nub to fix the length. All of these devices are preferably configured to permit endoscopic delivery through a single fire device, or a multiple fire or rapid reloadable device could be used, to minimize the number of times the delivery device needs to removed from the endoscope to be reloaded.

In order to facilitate holding the cuff in place while attaching, the cuff could come preloaded on a radially expanding support structure that can be removed following implantation. Or it could be held in place by a deflectable alligator clip or other grasping device that would hold the cuff against the GEJ at the target site.

U.S. patent application Ser. No. 10/698,148 describes gastric and gastrointestinal sleeve devices that include inflatable balloons for structural support of the sleeve and/or for enhancing the patient's feeling of satiety. An enhanced method of using these devices is to inflate the balloons with a fluid containing a nontoxic detectable dye, such as methylene blue. If any of the inflatable balloon members should develop a leak, the methylene blue will be passed in the urine and be detectable by the patient. The patient should then contact a physician to determine whether repair or replacement of the device is indicated.

Another concept described in the Ser. No. 10/698,148 application involves the placement of a mounting ring or other attachment device within the gastrointestinal system and attaching various other devices or components to the attachment device. Enhancements to that concept for treating GERD, MO and other disorders of the gastrointestinal tract could include placing/attaching a nonrestrictive mounting ring at or near the GEJ and attaching/removing/replacing various therapeutic or diagnostic devices to the mounting ring, such as a valve to prevent reflux, a restriction to food intake, a sleeve, a telemetry or imaging capsule, etc.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A method of adjusting therapy in a patient, comprising the steps of:
    identifying a patient with an implanted first gastrointestinal bypass tube having a first length, the first bypass tube releasably connected to a support which is attached to tissue in the vicinity of the gastroesophageal junction;
    separating the first bypass tube from the support and removing the first bypass tube from the patient after separating the first bypass tube from the support;
    providing a second bypass tube, having a second length which is different than the first length; and
    attaching the second bypass tube to the support.

2. A method of adjusting therapy in a patient as in claim 1, wherein the second length is longer than the first length.

3. A method of adjusting therapy in a patient as in claim 1, wherein the second length is shorter than the first length.

4. A method of adjusting therapy in a patient as in claim 1, wherein the attaching step is accomplished endoscopically.

5. A method of adjusting therapy in a patient as in claim 1, wherein attaching the second bypass tube to the support comprises attaching the proximal end of the second bypass tube to the distal end of the support.

6. A method of adjusting therapy in a patient as in claim 1, wherein the support comprises an attachment cuff having a lumen therethrough for the passage of ingested contents from the cuff into the first bypass tube.

7. A method of adjusting therapy in a patient as in claim 6, wherein the attachment cuff is flexible.

8. A method of adjusting therapy in a patient as in claim 6, wherein the attachment cuff is configured to stretch by at least about 150% in the radial direction.

9. A method of adjusting therapy in a patient as in claim 1, wherein the first bypass tube has a length of at least about 50 cm.

10. A method of adjusting therapy in a patient as in claim 1, wherein the first bypass tube has a length of at least about 75 cm.

11. A method of adjusting therapy in a patient as in claim 1, wherein the first bypass tube has a length of at least about 100 cm.

12. A method of adjusting therapy in a patient as in claim 1, wherein attaching the second bypass tube to the support comprises suturing the second bypass tube to the support.

13. A method of adjusting therapy in a patient as in claim 1, wherein attaching the second bypass tube to the support comprises hooking the second bypass tube to the support.

14. A method of adjusting therapy in a patient as in claim 1, wherein attaching the second bypass tube to the support comprises stapling the second bypass tube to the support.

15. A method of adjusting therapy in a patient as in claim 1, wherein attaching the second bypass tube to the support comprises connecting a first attachment surface on the support to a second attachment surface on the second bypass tube.

16. A method of adjusting therapy in a patient as in claim 15, wherein the first attachment surface comprises an annular ridge.

17. A method of adjusting therapy in a patient as in claim 15, wherein the second attachment surface comprises a ring.

* * * * *